United States Patent
Fischer et al.

(10) Patent No.: US 9,375,428 B2
(45) Date of Patent: Jun. 28, 2016

(54) MORPHINE CONTROLLED RELEASE SYSTEM

(71) Applicant: Egalet Ltd., London (GB)

(72) Inventors: Gina Fischer, Vaerløse (DK); Daniel Bar-Shalom, Kokkedal (DK); Lillian Slot, Virum (DK); Christine Andersen, Vedbaek (DK)

(73) Assignee: EGALET LTD., London (GB)

( * ) Notice: Subject to any disclaimer, the term of this patent is extended or adjusted under 35 U.S.C. 154(b) by 0 days.

(21) Appl. No.: 14/496,561

(22) Filed: Sep. 25, 2014

(65) Prior Publication Data

US 2015/0079150 A1 Mar. 19, 2015

Related U.S. Application Data

(63) Continuation of application No. 10/550,453, filed as application No. PCT/DK2004/000215 on Mar. 26, 2004, now Pat. No. 8,877,241.

(30) Foreign Application Priority Data

Mar. 26, 2003 (DK) .................................. 2003 00463

(51) Int. Cl.
   A61K 9/00 (2006.01)
   A61K 9/70 (2006.01)
   A61K 31/485 (2006.01)
(52) U.S. Cl.
   CPC ............. *A61K 31/485* (2013.01); *A61K 9/0092* (2013.01); *A61K 9/70* (2013.01)
(58) Field of Classification Search
   CPC ...... A61K 31/485; A61K 9/0092; A61K 9/70
   See application file for complete search history.

(56) References Cited

U.S. PATENT DOCUMENTS

| 2,685,553 A | 3/1951 | Carroll et al. |
| 3,835,221 A | 9/1974 | Fulberth et al. |

(Continued)

FOREIGN PATENT DOCUMENTS

| DE | 2332484 | 6/1972 |
| DE | 2415490 | 4/1973 |

(Continued)

OTHER PUBLICATIONS

U.S. Appl. No. 13/803,132, filed Aug. 25, 2006, Purdue Pharma C.

(Continued)

*Primary Examiner* — Aradhana Sasan
(74) *Attorney, Agent, or Firm* — Foley & Lardner LLP

(57) ABSTRACT

Described are controlled release oral pharmaceutical composition comprising an erodible matrix composition comprising a polyethylene oxide, a therapeutically effective amount of an opioid or a pharmaceutically acceptable salt, complex, solvate or anhydrate thereof, or a mixture thereof and, optionally, one or more pharmaceutically acceptable excipients, and a coating on the matrix composition, wherein the coating has at least one opening exposing a surface of an end portion of the matrix composition, thereby allowing controlled release of the opioid by erosion of the matrix surface, wherein the composition exhibits zero order release of at least 80% of the opioid contained in the composition. The matrix may have a cylindrical shape having a long axis and a conus-shaped end portion having a largest diameter and a smallest diameter, such that the surface area exposed increases during erosion of the conus-shaped end portion.

24 Claims, 22 Drawing Sheets

(56) References Cited

U.S. PATENT DOCUMENTS

| | | | |
|---|---|---|---|
| 3,957,523 A | 5/1976 | Ohno et al. |
| 4,034,758 A | 7/1977 | Theeuwes |
| 4,330,338 A | 5/1982 | Banker |
| 4,389,393 A | 6/1983 | Schor et al. |
| 4,404,183 A | 9/1983 | Kawata et al. |
| 4,449,983 A | 5/1984 | Cortese et al. |
| 4,686,212 A | 8/1987 | Ducatman et al. |
| 4,824,675 A | 4/1989 | Wong et al. |
| 4,844,984 A | 7/1989 | Eckenhoff et al. |
| 4,873,080 A | 10/1989 | Brickl et al. |
| 4,892,742 A | 1/1990 | Shah |
| 4,898,733 A | 2/1990 | De Prince et al. |
| 5,019,396 A | 5/1991 | Ayer et al. |
| 5,068,112 A | 11/1991 | Samejima et al. |
| 5,102,668 A | 4/1992 | Eichel et al. |
| 5,213,808 A | 5/1993 | Bar-Shalom et al. |
| 5,266,331 A | 11/1993 | Oshlack et al. |
| 5,281,420 A | 1/1994 | Kelm et al. |
| 5,352,455 A | 10/1994 | Robertson |
| 5,411,745 A | 5/1995 | Oshlack et al. |
| 5,419,917 A | 5/1995 | Chen et al. |
| 5,422,123 A | 6/1995 | Conte et al. |
| 5,460,826 A | 10/1995 | Merrill et al. |
| 5,478,577 A | 12/1995 | Sackler et al. |
| 5,508,042 A | 4/1996 | Oshlack et al. |
| 5,520,931 A | 5/1996 | Persson et al. |
| 5,549,912 A | 8/1996 | Oshlack et al. |
| 5,593,695 A | 1/1997 | Merrill et al. |
| 5,609,885 A | 3/1997 | Rivera et al. |
| 5,614,218 A | 3/1997 | Olsson et al. |
| 5,618,560 A | 4/1997 | Bar-Shalom et al. |
| 5,656,291 A | 8/1997 | Olsson et al. |
| 5,656,295 A | 8/1997 | Oshlack et al. |
| 5,667,805 A | 9/1997 | Merrill et al. |
| 5,741,524 A | 4/1998 | Staniforth et al. |
| 5,866,161 A | 2/1999 | Childers et al. |
| 5,866,164 A | 2/1999 | Kuczynski et al. |
| 5,869,097 A | 2/1999 | Wong et al. |
| 5,879,705 A | 3/1999 | Heafield et al. |
| 5,882,682 A | 3/1999 | Rork et al. |
| 5,914,131 A | 6/1999 | Merrill et al. |
| 5,948,787 A | 9/1999 | Merrill et al. |
| 5,952,005 A | 9/1999 | Olsson et al. |
| 5,968,551 A | 10/1999 | Oshlack et al. |
| 6,046,177 A | 4/2000 | Stella et al. |
| 6,066,339 A | 5/2000 | Stark et al. |
| 6,077,533 A | 6/2000 | Oshlack et al. |
| 6,077,538 A | 6/2000 | Merrill et al. |
| 6,103,261 A | 8/2000 | Chasin et al. |
| 6,117,453 A | 9/2000 | Seth et al. |
| 6,143,328 A | 11/2000 | Heafield et al. |
| 6,183,778 B1 | 2/2001 | Conte et al. |
| 6,225,343 B1 | 5/2001 | Behl et al. |
| 6,245,351 B1 | 6/2001 | Nara et al. |
| 6,245,357 B1 | 6/2001 | Edgren et al. |
| 6,267,981 B1 | 7/2001 | Okamoto et al. |
| 6,267,985 B1 | 7/2001 | Chen et al. |
| 6,277,384 B1 | 8/2001 | Kaiko et al. |
| 6,284,274 B1 | 9/2001 | Merrill et al. |
| 6,294,195 B1 | 9/2001 | Oshlack et al. |
| 6,348,216 B1 | 2/2002 | Kushla et al. |
| 6,375,957 B1 | 4/2002 | Kaiko et al. |
| 6,383,471 B1 | 5/2002 | Chen et al. |
| 6,395,299 B1 | 5/2002 | Babich et al. |
| 6,399,096 B1 | 6/2002 | Miller et al. |
| 6,403,579 B1 | 6/2002 | Heller |
| 6,451,848 B1 | 9/2002 | Behl et al. |
| 6,458,772 B1 | 10/2002 | Zhou et al. |
| 6,458,824 B1 | 10/2002 | Iwata et al. |
| 6,475,494 B2 | 11/2002 | Kaiko et al. |
| 6,482,437 B2 | 11/2002 | Debregeas et al. |
| 6,488,962 B1 | 12/2002 | Berner et al. |
| 6,488,963 B1 | 12/2002 | McGinity et al. |
| 6,491,945 B1 | 12/2002 | Childers et al. |
| 6,517,866 B1 | 2/2003 | Am Ende et al. |
| 6,534,085 B1 | 3/2003 | Zeligs |
| 6,543,085 B2 | 4/2003 | Holsten et al. |
| 6,562,375 B1 | 5/2003 | Sako et al. |
| 6,572,885 B2 | 6/2003 | Oshlack et al. |
| 6,599,531 B2 | 7/2003 | Kushla et al. |
| 6,607,751 B1 | 8/2003 | Odidi et al. |
| 6,673,816 B1 | 1/2004 | Esswein et al. |
| 6,685,964 B1 | 2/2004 | Bartholomaeus et al. |
| 6,696,066 B2 | 2/2004 | Kaiko et al. |
| 6,709,678 B2 | 3/2004 | Gruber |
| 6,733,783 B2 | 5/2004 | Oshlack et al. |
| 6,757,558 B2 | 6/2004 | Lange et al. |
| 6,787,156 B1 | 9/2004 | Bar-Shalom |
| 6,800,668 B1 | 10/2004 | Odidi et al. |
| 6,852,337 B2 | 2/2005 | Gabel et al. |
| 7,060,293 B1 | 6/2006 | Oshlack et al. |
| 7,063,864 B1 | 6/2006 | Marechal et al. |
| 7,090,867 B2 | 8/2006 | Odidi et al. |
| 7,144,587 B2 | 12/2006 | Oshlack et al. |
| 7,172,767 B2 | 2/2007 | Kaiko et al. |
| 7,201,920 B2 | 4/2007 | Kumar et al. |
| 7,270,831 B2 | 9/2007 | Oshlack et al. |
| 7,332,182 B2 | 2/2008 | Sackler |
| 7,419,686 B2 | 9/2008 | Kaiko et al. |
| 7,476,402 B2 | 1/2009 | Kumar et al. |
| 7,510,726 B2 | 3/2009 | Kumar et al. |
| 7,510,727 B2 | 3/2009 | Oshlack et al. |
| 7,514,100 B2 | 4/2009 | Oshlack et al. |
| 7,666,337 B2 | 2/2010 | Yang et al. |
| 7,749,542 B2 | 7/2010 | Kaiko et al. |
| 7,771,707 B2 | 8/2010 | Hirsh et al. |
| 7,776,314 B2 | 8/2010 | Bartholomaus et al. |
| 7,790,215 B2 | 9/2010 | Sackler et al. |
| 7,842,307 B2 | 11/2010 | Oshlack et al. |
| 7,846,476 B2 | 12/2010 | Oshlack et al. |
| 7,883,722 B2 | 2/2011 | Bar-Shalom |
| 7,883,772 B2 | 2/2011 | Pourdeyhimi et al. |
| 7,897,080 B2 | 3/2011 | Yang et al. |
| 7,906,143 B1 | 3/2011 | Odidi et al. |
| 7,943,174 B2 | 5/2011 | Oshlack et al. |
| 7,968,120 B2 | 6/2011 | Li et al. |
| 7,981,439 B2 | 7/2011 | Kumar et al. |
| 8,017,148 B2 | 9/2011 | Sackler |
| 8,017,150 B2 | 9/2011 | Yang et al. |
| 8,029,822 B2 | 10/2011 | Faour et al. |
| 8,075,872 B2 | 12/2011 | Arkenau-Maric et al. |
| 8,101,630 B2 | 1/2012 | Kumar et al. |
| 8,105,631 B2 | 1/2012 | Kaiko et al. |
| 8,114,383 B2 | 2/2012 | Bartholomaus et al. |
| 8,114,384 B2 | 2/2012 | Arkenau et al. |
| 8,133,507 B2 | 3/2012 | Yum et al. |
| 8,142,811 B2 | 3/2012 | Oshlack et al. |
| 8,147,870 B2 | 4/2012 | Yum et al. |
| 8,153,152 B2 | 4/2012 | Yum et al. |
| 8,168,217 B2 | 5/2012 | Yum et al. |
| 8,173,152 B2 | 5/2012 | Crowley et al. |
| 8,182,836 B2 | 5/2012 | Mehta |
| 8,192,722 B2 | 6/2012 | Arkenau-Maric et al. |
| 8,231,898 B2 | 7/2012 | Oshlack et al. |
| 8,309,060 B2 | 11/2012 | Bartholomaus et al. |
| 8,323,889 B2 | 12/2012 | Arkenau-Maric et al. |
| 8,329,720 B1 | 12/2012 | King et al. |
| 8,337,888 B2 | 12/2012 | Wright et al. |
| 8,338,444 B1 | 12/2012 | King et al. |
| 8,354,124 B2 | 1/2013 | Yum et al. |
| 8,361,499 B2 | 1/2013 | Oshlack et al. |
| 8,367,693 B1 | 2/2013 | King et al. |
| 8,372,432 B2 | 2/2013 | Han et al. |
| 8,377,453 B2 | 2/2013 | Han et al. |
| 8,383,152 B2 | 2/2013 | Jans et al. |
| 8,383,154 B2 | 2/2013 | Bar-Shalom |
| 8,383,155 B2 | 2/2013 | Bar-Shalom |
| 8,389,007 B2 | 3/2013 | Wright et al. |
| 8,394,407 B2 | 3/2013 | Vergnault et al. |
| 8,394,408 B2 | 3/2013 | Han et al. |
| 8,409,616 B2 | 4/2013 | Kumar et al. |
| 8,415,401 B2 | 4/2013 | Yum et al. |
| 8,420,056 B2 | 4/2013 | Arkenau-Maric et al. |
| 8,420,120 B2 | 4/2013 | Yum et al. |

(56) References Cited

U.S. PATENT DOCUMENTS

| | | | |
|---|---|---|---|
| 8,425,933 B2 | 4/2013 | Mehta | |
| 8,445,018 B2 | 5/2013 | Habib et al. | |
| 8,449,909 B2 | 5/2013 | Hirsh et al. | |
| 8,460,640 B2 | 6/2013 | Vinson et al. | |
| 8,465,776 B2 | 6/2013 | Hoarau | |
| 8,470,361 B2 | 6/2013 | Pettersson | |
| 8,476,291 B1 | 7/2013 | King et al. | |
| 8,486,448 B2 | 7/2013 | Rahmouni et al. | |
| 8,486,449 B2 | 7/2013 | Rahmouni et al. | |
| 8,491,935 B2 | 7/2013 | Mehta et al. | |
| 8,501,160 B2 | 8/2013 | Cailly-Dufestel et al. | |
| 8,506,998 B2 | 8/2013 | Miller et al. | |
| 8,524,275 B2 | 9/2013 | Oshlack et al. | |
| 8,524,277 B2 | 9/2013 | Edgren et al. | |
| 8,529,848 B2 | 9/2013 | Danehy et al. | |
| 8,603,526 B2 | 12/2013 | Tygesen et al. | |
| 8,609,143 B2 | 12/2013 | Fischer et al. | |
| 8,609,683 B2 | 12/2013 | Wright et al. | |
| 8,617,605 B2 | 12/2013 | Fischer et al. | |
| 8,637,540 B2 | 1/2014 | Kumar et al. | |
| 8,808,745 B2 * | 8/2014 | Fischer et al. | 424/486 |
| 8,877,241 B2 | 11/2014 | Fischer et al. | |
| 9,005,660 B2 | 4/2015 | Tygesen et al. | |
| 9,023,394 B2 | 5/2015 | Andersen et al. | |
| 9,044,402 B2 | 6/2015 | Tygesen et al. | |
| 9,168,228 B2 | 10/2015 | Tygesen et al. | |
| 2001/0036959 A1 | 11/2001 | Gabel et al. | |
| 2001/0036960 A1 | 11/2001 | Decker et al. | |
| 2001/0053791 A1 | 12/2001 | Babcock et al. | |
| 2002/0054911 A1 | 5/2002 | Oh | |
| 2002/0107434 A1 | 8/2002 | Lange et al. | |
| 2003/0035836 A1 | 2/2003 | Shanghvi et al. | |
| 2003/0068375 A1 | 4/2003 | Wright et al. | |
| 2003/0077320 A1 | 4/2003 | Childers et al. | |
| 2003/0118641 A1 | 6/2003 | Maloney et al. | |
| 2003/0133976 A1 | 7/2003 | Pather et al. | |
| 2003/0203055 A1 | 10/2003 | Rao et al. | |
| 2003/0224051 A1 | 12/2003 | Fink et al. | |
| 2004/0010000 A1 | 1/2004 | Ayer et al. | |
| 2004/0028733 A1 | 2/2004 | Tracy et al. | |
| 2004/0091529 A1 | 5/2004 | Edgren et al. | |
| 2004/0102476 A1 | 5/2004 | Chan et al. | |
| 2004/0115262 A1 | 6/2004 | Jao et al. | |
| 2004/0151772 A1 | 8/2004 | Andersen et al. | |
| 2004/0202717 A1 | 10/2004 | Mehta | |
| 2004/0204474 A1 | 10/2004 | Decker et al. | |
| 2004/0213849 A1 | 10/2004 | Sowden et al. | |
| 2004/0220250 A1 | 11/2004 | Oh et al. | |
| 2004/0224020 A1 | 11/2004 | Schoenhard | |
| 2004/0234602 A1 | 11/2004 | Fischer et al. | |
| 2004/0253310 A1 | 12/2004 | Fischer et al. | |
| 2005/0019399 A1 | 1/2005 | Fischer et al. | |
| 2005/0019405 A1 | 1/2005 | Bar-Shalom | |
| 2005/0053655 A1 | 3/2005 | Yang et al. | |
| 2005/0074493 A1 | 4/2005 | Mehta et al. | |
| 2005/0089569 A1 | 4/2005 | Bar-Shalom | |
| 2005/0095295 A1 | 5/2005 | Maggi et al. | |
| 2005/0106249 A1 | 5/2005 | Hwang et al. | |
| 2005/0158382 A1 | 7/2005 | Cruz et al. | |
| 2005/0163837 A1 | 7/2005 | Boehm et al. | |
| 2005/0169992 A1 | 8/2005 | Jao et al. | |
| 2005/0236741 A1 | 10/2005 | Arkenau et al. | |
| 2006/0002860 A1 | 1/2006 | Bartholomaus et al. | |
| 2006/0039864 A1 | 2/2006 | Bartholomaus et al. | |
| 2006/0110327 A1 | 5/2006 | Emigh et al. | |
| 2006/0165790 A1 | 7/2006 | Walden et al. | |
| 2006/0177380 A1 | 8/2006 | Emigh et al. | |
| 2006/0177507 A1 | 8/2006 | Faour et al. | |
| 2006/0193782 A1 | 8/2006 | Bartholomaus et al. | |
| 2006/0193912 A1 | 8/2006 | Ketsela et al. | |
| 2006/0193914 A1 | 8/2006 | Ashworth et al. | |
| 2007/0003616 A1 | 1/2007 | Arkenau-Maric et al. | |
| 2007/0003620 A1 | 1/2007 | Marechal et al. | |
| 2007/0004797 A1 | 1/2007 | Weyers et al. | |
| 2007/0020331 A1 | 1/2007 | Gold et al. | |
| 2007/0042044 A1 | 2/2007 | Fischer et al. | |
| 2007/0048228 A1 | 3/2007 | Arkenau-Maric et al. | |
| 2007/0065364 A1 | 3/2007 | Oshlack et al. | |
| 2007/0065510 A1 | 3/2007 | Odidi et al. | |
| 2007/0122455 A1 | 5/2007 | Myers et al. | |
| 2007/0183980 A1 | 8/2007 | Arkenau-Maric et al. | |
| 2007/0190142 A1 | 8/2007 | Breitenbach et al. | |
| 2007/0224129 A1 | 9/2007 | Guimberteau et al. | |
| 2007/0231268 A1 | 10/2007 | Emigh et al. | |
| 2007/0264326 A1 | 11/2007 | Guimberteau et al. | |
| 2007/0281003 A1 | 12/2007 | Fuisz et al. | |
| 2007/0281007 A1 | 12/2007 | Jacob et al. | |
| 2008/0026052 A1 | 1/2008 | Schoenhard | |
| 2008/0044454 A1 | 2/2008 | Yang et al. | |
| 2008/0063725 A1 | 3/2008 | Guimberteau et al. | |
| 2008/0069891 A1 | 3/2008 | Habib et al. | |
| 2008/0102121 A1 | 5/2008 | Devane et al. | |
| 2008/0113025 A1 | 5/2008 | Devane et al. | |
| 2008/0152595 A1 | 6/2008 | Emigh et al. | |
| 2008/0166405 A1 | 7/2008 | Mehta | |
| 2008/0166407 A1 | 7/2008 | Shalaby et al. | |
| 2008/0234352 A1 | 9/2008 | Fischer et al. | |
| 2008/0247959 A1 | 10/2008 | Bartholomaus et al. | |
| 2008/0248110 A1 | 10/2008 | Pettersson et al. | |
| 2008/0248113 A1 | 10/2008 | Bartholomaus et al. | |
| 2008/0254122 A1 | 10/2008 | Fischer et al. | |
| 2008/0254123 A1 | 10/2008 | Fischer et al. | |
| 2008/0254124 A1 | 10/2008 | Bar-Shalom | |
| 2008/0268057 A1 | 10/2008 | Andersen et al. | |
| 2008/0311187 A1 | 12/2008 | Ashworth et al. | |
| 2008/0311205 A1 | 12/2008 | Habib et al. | |
| 2008/0317854 A1 | 12/2008 | Arkenau et al. | |
| 2009/0004267 A1 | 1/2009 | Arkenau-Maric et al. | |
| 2009/0005408 A1 | 1/2009 | Arkenau-Maric et al. | |
| 2009/0022790 A1 | 1/2009 | Flath et al. | |
| 2009/0022798 A1 | 1/2009 | Rosenberg et al. | |
| 2009/0041838 A1 | 2/2009 | Guimberteau et al. | |
| 2009/0081290 A1 | 3/2009 | McKenna et al. | |
| 2009/0123386 A1 | 5/2009 | Young | |
| 2009/0169631 A1 | 7/2009 | Zamloot et al. | |
| 2009/0202634 A1 | 8/2009 | Jans et al. | |
| 2009/0221621 A1 | 9/2009 | Sathyan et al. | |
| 2009/0232887 A1 | 9/2009 | Odidi et al. | |
| 2009/0274759 A1 | 11/2009 | Bar-Shalom et al. | |
| 2009/0298862 A1 | 12/2009 | Yum et al. | |
| 2009/0317355 A1 | 12/2009 | Roth et al. | |
| 2010/0151028 A1 | 6/2010 | Ashworth et al. | |
| 2010/0168148 A1 | 7/2010 | Wright et al. | |
| 2010/0172989 A1 | 7/2010 | Roth et al. | |
| 2010/0203129 A1 | 8/2010 | Andersen et al. | |
| 2010/0204259 A1 | 8/2010 | Tygesen et al. | |
| 2010/0239667 A1 | 9/2010 | Hemmingsen et al. | |
| 2010/0266701 A1 | 10/2010 | Guimberteau et al. | |
| 2010/0291205 A1 | 11/2010 | Downie et al. | |
| 2011/0008424 A1 | 1/2011 | Chang et al. | |
| 2011/0020451 A1 | 1/2011 | Bartholmaus et al. | |
| 2011/0038930 A1 | 2/2011 | Barnscheid et al. | |
| 2011/0077238 A1 | 3/2011 | Leech et al. | |
| 2011/0104214 A1 | 5/2011 | Oshlack et al. | |
| 2011/0136847 A1 | 6/2011 | Chan et al. | |
| 2011/0142905 A1 | 6/2011 | Naelapaa et al. | |
| 2011/0159100 A1 | 6/2011 | Andersen et al. | |
| 2011/0165248 A1 | 7/2011 | Machonis | |
| 2011/0195989 A1 | 8/2011 | Rudnic et al. | |
| 2011/0200681 A1 | 8/2011 | Habib et al. | |
| 2011/0200715 A1 | 8/2011 | Fuisz et al. | |
| 2011/0229526 A1 | 9/2011 | Rosenberg et al. | |
| 2011/0229533 A1 | 9/2011 | Edgren et al. | |
| 2011/0287093 A1 | 11/2011 | Schoenhard | |
| 2012/0009129 A1 | 1/2012 | Brzeczko | |
| 2012/0059065 A1 | 3/2012 | Barnscheid et al. | |
| 2012/0065220 A1 | 3/2012 | Barnscheid et al. | |
| 2012/0135075 A1 | 5/2012 | Mohammad | |
| 2012/0136021 A1 | 5/2012 | Barnscheid et al. | |
| 2012/0164220 A1 | 6/2012 | Huang | |
| 2012/0201761 A1 | 8/2012 | Sackler | |
| 2012/0202838 A1 | 8/2012 | Ghosh et al. | |
| 2012/0202839 A1 | 8/2012 | Emigh et al. | |
| 2012/0214777 A1 | 8/2012 | Crowley et al. | |

(56) References Cited

U.S. PATENT DOCUMENTS

| | | |
|---|---|---|
| 2012/0251637 A1 | 10/2012 | Bartholomaus et al. |
| 2012/0321674 A1 | 12/2012 | Vachon et al. |
| 2012/0321713 A1 | 12/2012 | Han et al. |
| 2012/0321716 A1 | 12/2012 | Vachon et al. |
| 2013/0005823 A1 | 1/2013 | Emigh et al. |
| 2013/0011479 A1 | 1/2013 | Angeli et al. |
| 2013/0022646 A1 | 1/2013 | Rudnic et al. |
| 2013/0028177 A1 | 1/2013 | Koskela et al. |
| 2013/0028970 A1 | 1/2013 | Schwier et al. |
| 2013/0028972 A1 | 1/2013 | Schwier et al. |
| 2013/0030561 A1 | 1/2013 | Imanari et al. |
| 2013/0084333 A1 | 4/2013 | Dick et al. |
| 2013/0090349 A1 | 4/2013 | Geibler et al. |
| 2013/0122087 A1 | 5/2013 | Habib et al. |
| 2013/0122101 A1 | 5/2013 | Habib et al. |
| 2013/0129826 A1 | 5/2013 | Geibler et al. |
| 2013/0171075 A1 | 7/2013 | Arkenau-Maric et al. |
| 2013/0171257 A1 | 7/2013 | Kumar et al. |
| 2013/0195981 A1 | 8/2013 | Pettersson |
| 2013/0195982 A1 | 8/2013 | Pettersson |
| 2013/0209557 A1 | 8/2013 | Barnscheid |
| 2013/0209560 A1 | 8/2013 | Hamed et al. |
| 2013/0217716 A1 | 8/2013 | Wright et al. |
| 2013/0225697 A1 | 8/2013 | Barnscheid et al. |
| 2013/0230596 A1 | 9/2013 | Mehta |
| 2013/0245055 A1 | 9/2013 | Wright et al. |
| 2013/0251759 A1 | 9/2013 | Jans et al. |
| 2013/0251796 A1 | 9/2013 | Mckenna et al. |
| 2013/0251797 A1 | 9/2013 | Mckenna et al. |
| 2013/0251798 A1 | 9/2013 | Mckenna et al. |
| 2013/0251799 A1 | 9/2013 | Mckenna et al. |
| 2013/0251801 A1 | 9/2013 | Mckenna et al. |
| 2013/0251802 A1 | 9/2013 | Mckenna et al. |
| 2013/0251806 A1 | 9/2013 | Andrade De Freitas et al. |
| 2013/0259939 A1 | 10/2013 | Mckenna et al. |
| 2013/0259940 A1 | 10/2013 | Mckenna et al. |
| 2013/0260015 A1 | 10/2013 | Mckenna et al. |
| 2013/0261143 A1 | 10/2013 | Wright et al. |
| 2013/0280176 A1 | 10/2013 | Diezi et al. |
| 2013/0281480 A1 | 10/2013 | Yum et al. |
| 2013/0287845 A1 | 10/2013 | Yum et al. |
| 2013/0287849 A1 | 10/2013 | Andersen et al. |
| 2013/0295168 A1 | 11/2013 | Yum et al. |
| 2013/0303494 A1 | 11/2013 | Wright et al. |
| 2013/0317049 A1 | 11/2013 | Yum et al. |
| 2013/0317051 A1 | 11/2013 | Oshlack et al. |
| 2013/0320592 A1 | 12/2013 | Arkenau-Maric et al. |
| 2013/0337059 A1 | 12/2013 | Yum et al. |
| 2013/0337060 A1 | 12/2013 | Yum et al. |
| 2013/0344142 A1 | 12/2013 | Rahmouni et al. |
| 2013/0344143 A1 | 12/2013 | Rosenberg et al. |
| 2014/0004191 A1 | 1/2014 | Rahmouni et al. |
| 2014/0030327 A1 | 1/2014 | McKenna et al. |
| 2014/0120164 A1 * | 5/2014 | Fischer et al. ............... 424/486 |
| 2014/0155388 A1 | 6/2014 | Brzeczko et al. |
| 2014/0221416 A1 | 8/2014 | Guido et al. |
| 2014/0271848 A1 | 9/2014 | Guido et al. |
| 2014/0271849 A1 | 9/2014 | Raman et al. |
| 2014/0271896 A1 | 9/2014 | Shmeis et al. |
| 2014/0275143 A1 | 9/2014 | Devarakonda et al. |
| 2014/0294947 A1 | 10/2014 | Reilly et al. |
| 2014/0356426 A1 | 12/2014 | Barnscheid et al. |
| 2014/0356428 A1 | 12/2014 | Barnscheid et al. |
| 2015/0024048 A1 | 1/2015 | Hemmingsen et al. |
| 2015/0037417 A1 * | 2/2015 | Fischer et al. ............... 424/486 |
| 2015/0079150 A1 | 3/2015 | Fischer et al. |
| 2015/0150812 A1 | 6/2015 | Andersen et al. |

FOREIGN PATENT DOCUMENTS

| | | | |
|---|---|---|---|
| EP | 0 435 726 A2 | 7/1991 | |
| EP | 0 908 181 | 4/1999 | |
| EP | 0 335 560 | 1/2002 | |
| EP | 1 213 014 A2 | 6/2002 | |
| EP | 1 371 360 | 5/2005 | |
| GB | GB 1430684 | 3/1976 | |
| GB | 2170104 | 7/1986 | |
| GB | 2182559 | 5/1987 | |
| JP | 60/255719 | 12/1985 | |
| JP | 07/100191 | 4/1995 | |
| WO | WO 86/04817 | 8/1986 | |
| WO | WO 89/09066 | 10/1989 | |
| WO | WO 90/08536 | 8/1990 | |
| WO | WO 91 04015 | 4/1991 | |
| WO | WO 92/09270 | 6/1992 | |
| WO | WO 93/10765 | 6/1993 | |
| WO | WO 95/22962 | 8/1995 | |
| WO | WO 96/00066 A1 | 1/1996 | |
| WO | WO 96/08253 A1 | 3/1996 | |
| WO | WO 97/33566 A2 | 9/1997 | |
| WO | WO 99/05105 | 2/1999 | |
| WO | WO 99/44591 | 9/1999 | |
| WO | WO 99/44591 A1 | 9/1999 | |
| WO | WO 99/51208 | 10/1999 | |
| WO | WO 01/35958 | 5/2001 | |
| WO | WO 01/51035 | 7/2001 | |
| WO | WO 01/51036 | 7/2001 | |
| WO | WO 01/74357 | 10/2001 | |
| WO | WO 02/056861 A2 | 7/2002 | |
| WO | WO 02/065834 | 8/2002 | |
| WO | WO 02/87512 A1 | 11/2002 | |
| WO | WO 02/092078 | 11/2002 | |
| WO | WO 03/024429 A1 * | 3/2003 | ............... A61K 9/22 |
| WO | WO 03/024430 A1 * | 3/2003 | ............... A61K 9/28 |
| WO | WO 03/092648 A1 | 11/2003 | |
| WO | WO 03/101384 A2 | 12/2003 | |
| WO | WO 2004/002447 A2 | 1/2004 | |
| WO | WO 2004/047839 A1 | 6/2004 | |
| WO | WO 2004/054542 A2 | 7/2004 | |
| WO | WO 2004/056337 A2 | 7/2004 | |
| WO | WO 2004/091512 A2 | 10/2004 | |
| WO | WO 2005/000310 A1 | 1/2005 | |
| WO | WO 2005/007074 | 1/2005 | |
| WO | WO 2005/016313 A1 | 2/2005 | |
| WO | WO 2005/016314 A1 | 2/2005 | |
| WO | WO 2005/027878 | 3/2005 | |
| WO | WO 2005/034859 A2 | 4/2005 | |
| WO | WO 2005/053587 A1 | 6/2005 | |
| WO | WO 2005/063206 A1 | 7/2005 | |
| WO | WO 2005/063214 A1 | 7/2005 | |
| WO | WO 2005/102286 A1 | 11/2005 | |
| WO | WO 2006/002883 A1 | 1/2006 | |
| WO | WO 2006/002884 A1 | 1/2006 | |
| WO | WO 2006/002886 A1 | 1/2006 | |
| WO | WO 2006/030402 A2 | 3/2006 | |
| WO | WO 2006/031209 A1 | 3/2006 | |
| WO | WO 2006/058249 A2 | 6/2006 | |
| WO | WO 2006/088305 A1 | 8/2006 | |
| WO | WO 2006/089843 A2 | 8/2006 | |
| WO | WO 2006/103418 A1 | 10/2006 | |
| WO | WO 2007/014061 A2 | 2/2007 | |
| WO | WO 2007/030754 A2 | 3/2007 | |
| WO | WO 2007/082757 A2 | 7/2007 | |
| WO | WO 2007/085024 A2 | 7/2007 | |
| WO | WO 2007/106550 A2 | 9/2007 | |
| WO | WO 2007/112285 A2 | 10/2007 | |
| WO | WO 2007/112286 A2 | 10/2007 | |
| WO | WO 2007/133583 A2 | 11/2007 | |
| WO | WO 2007/135193 A2 | 11/2007 | |
| WO | WO 2007/150074 A2 | 12/2007 | |
| WO | WO 2007/150075 A2 | 12/2007 | |
| WO | WO 2008/023261 A1 | 2/2008 | |
| WO | WO 2008/027442 A2 | 3/2008 | |
| WO | WO 2008/028047 A2 | 3/2008 | |
| WO | WO 2008/033523 A1 | 3/2008 | |
| WO | WO 2008/068471 A1 | 6/2008 | |
| WO | WO 2008/100375 A2 | 8/2008 | |
| WO | WO 2008/107149 A2 | 9/2008 | |
| WO | WO 2009/035474 A1 | 3/2009 | |
| WO | WO 2009/075782 A1 | 6/2009 | |
| WO | WO 2009/076236 A2 | 6/2009 | |
| WO | WO 2009/076764 A1 | 6/2009 | |
| WO | WO 2009/088414 A2 | 7/2009 | |

(56) References Cited

FOREIGN PATENT DOCUMENTS

| WO | WO 2009/092601 A1 | 7/2009 |
|---|---|---|
| WO | WO 2009/104838 A1 | 8/2009 |
| WO | WO 2009/114648 A1 | 9/2009 |
| WO | WO 2010/017821 A1 | 2/2010 |
| WO | WO 2010/032128 A1 | 3/2010 |
| WO | WO 2010/066034 A1 | 6/2010 |
| WO | WO 2010/069050 A1 | 6/2010 |
| WO | WO 2010/083894 A1 | 7/2010 |
| WO | WO 2010/140007 A2 | 12/2010 |
| WO | WO 2010/151741 A1 | 12/2010 |
| WO | WO 2011/009602 A1 | 1/2011 |
| WO | WO 2011/009603 A1 | 1/2011 |
| WO | WO 2011/009604 A | 1/2011 |
| WO | WO 2011/041414 A1 | 4/2011 |
| WO | WO 2011/068723 A1 | 6/2011 |
| WO | WO 2011/079248 A1 | 6/2011 |
| WO | WO 2011/106416 A2 | 9/2011 |
| WO | WO 2012/028317 A1 | 3/2012 |
| WO | WO 2012/028318 A1 | 3/2012 |
| WO | WO 2012/028319 A1 | 3/2012 |
| WO | WO 2012/040651 A1 | 3/2012 |
| WO | WO 2012/061779 A1 | 5/2012 |
| WO | WO 2012/076907 A2 | 6/2012 |
| WO | WO 2012/080833 A2 | 6/2012 |
| WO | WO 2012/085656 A2 | 6/2012 |
| WO | WO 2012/085657 A2 | 6/2012 |
| WO | WO 2012/112952 A1 | 8/2012 |
| WO | WO 2012/131463 A2 | 10/2012 |
| WO | WO 2013/017234 A1 | 2/2013 |
| WO | WO 2013/017242 A1 | 2/2013 |
| WO | WO 2013/030177 | 3/2013 |
| WO | WO 2013/038267 A1 | 3/2013 |
| WO | WO 2013/038268 A1 | 3/2013 |
| WO | WO 2013/050539 A2 | 4/2013 |
| WO | WO 2013/057570 A2 | 4/2013 |
| WO | WO 2013/072395 A1 | 5/2013 |
| WO | WO 2013/077851 A1 | 5/2013 |
| WO | WO 2013/084059 A1 | 6/2013 |
| WO | WO 2013/128276 | 9/2013 |
| WO | WO 2013/171146 | 11/2013 |
| WO | WO 2014/190440 | 2/2014 |
| WO | WO 2014/091437 | 6/2014 |

OTHER PUBLICATIONS

U.S. Appl. No. 13/900,933, filed Aug. 25, 2006, Purdue Pharma C.
U.S. Appl. No. 13/949,966, filed Dec. 18, 2002, Pain Therapeutics A.
International Search Report issued on Jul. 8, 2008 in application No. PCT/DK2008/000016 (corresponding to U.S. Pat. No. 8,603,526).
International Search Report issued on Oct. 20, 2009 in application No. PCT/DK2009/000192.
International Search Report issued on Apr. 21, 2010 in application No. PCT/EP2010/00728 (corresponding to US 2010/0204259).
International Search Report issued on May 18, 2010 in application No. PCT/DK2010/00019 (corresponding to U.S. Pat. No. 8,603,526).
International Search Report issued on Jun. 2, 2010 in application No. PCT/DK2010/050016 (corresponding to US 2010/203129).
International Search Report issued on Jan. 28, 2009 in application No. PCT/EP2008/056910 (corresponding to US 2010/239667).
MiraLAX®, "MiraLAX® Drug Description," Oct. 19, 2011.
Raehal et al, "Mu Opioid 'Receptor' Regulation and Opiate Responsiveness," The AAPS Journal, vol. 7, No. 3, pp. E587-E591, 2005.
Qiu et al., "Design of a core-shelled polymer cylinder for potential programmable drug delivery," International Journal of Pharmaceutics, vol. 219, pp. 151-160, 2001.
Haahr et al., "Drug abuse resistant, controlled release, using Egalet® dosage units," Proceedings of the 34th Annual Meeting Exposition of the Controlled Release Society, Poster, Jul. 7-11, 2007.
Meyer et al., "Awareness Topic: Mitigating the Risks of Ethanol Induced Dose Dumping from Oral Sustained/Controlled Release Dosage Forms," FDA's ACPS meeting, Oct. 2005.
Dahlstrom et al., "Patient-controlled Analgesic Therapy, Part IV: Pharmacokinectics and Analgesic Plasma Concentration of Morphine," Clinical Pharmacokinectics, vol. 7, pp. 266-279, 1982.
Fischer et al., "Nonmedical Use of Prescription Opioids: Furthering a Meaningful Research Agenda," The Journal of Pain, vol. 9, No. 6, pp. 490-493, Jun. 2008.
Camu et al, "Pharmacology of systemic analgesics," Best Practice & Research Clinical Anaesthesiology, vol. 16, No. 4, pp. 475-488, 2002.
Graves et al., "Relationship between plasma morphine concentrations and pharmacologic effects in postoperative patients using patient-controlled analgesia," Clinical Pharmacy, vol. 4, pp. 41-47, Jan.-Feb. 1985.
Roberts et al., "Enterohepatic Circulation: Physiological, Pharmacokinetic and Clinical Implications," Clin. Pharmacokinet., vol. 41, Issue 10, pp. 751-790, 2002.
"Ascorbic acid," Wikipedia, http://en.wikipedia.org/wiki/Ascorbic_acid, accessed Jan. 23, 2014.
National Institute on Drug Abuse, "Prescription Medications," http://www.nida.nih.gov/drugpages/prescription.html, accessed on Jul. 15, 2008.
Brannan et al., "Affine Geometry," Geometry, 2nd edition, p. 78, 2012.
Katikaneni et al., "Ethylcellulose matrix controlled release tablets of a water-soluble drug," International Journal of Pharmaceutics, vol. 123, pp. 119-125, 1995.
Wanka et al., "Phase Diagrams and Aggregation Behavior of Poly(oxyethylene)- Poly(oxypropylene)-Poly(oxyethylene) Triblock Copolymers in Aqueous Solutions," vol. 27, pp. 4145-4159, 1994.
National Institute on Drug Abuse, "Monitoring the Future: National Results on Adolescent Drug Use," http://www.samhsa.gov, May 2009.
Office Action issued on Feb. 24, 2012 in U.S. Appl. No. 12/701,248 (US 2010/0204259).
Office Action issued on Jul. 20, 2012 in U.S. Appl. No. 12/701,248 (US 2010/0204259).
Office Action issued on Sep. 9, 2013 in U.S. Appl. No. 12/523,045 (US 2010/0291205).
Office Action issued on May 24, 2012 in U.S. Appl. No. 12/523,045 (US 2010/0291205).
Office Action issued on Oct. 26, 2011 in U.S. Appl. No. 12/523,045 (US 2010/0291205).
Office Action issued on Sep. 14, 2012 in U.S. Appl. No. 12/694,197 (US 2010/0203129).
Office Action issued on Apr. 11, 2012 in U.S. Appl. No. 12/694,197 (US 2010/0203129).
Office Action issued on Dec. 19, 2013 in U.S. Appl. No. 12/602,953 (US 2010/0239667).
Office Action issued on Mar. 7, 2013 in U.S. Appl. No. 12/602,953 (US 2010/0239667).
Notice of Allowance issued on Jul. 24, 2013 in U.S. Appl. No. 12/701,429 (U.S. Pat. No. 8,603,526).
Office Action issued on Oct. 17, 2012 in U.S. Appl. No. 12/701,429 (U.S. Pat. No. 8,603,526).
Office Action issued on Sep. 9, 2013 in U.S. Appl. No. 12/823,067 (U.S. Pat. No. 8,563,038).
Notice of Allowance issued on Jun. 11, 2013 in U.S. Appl. No. 12/823,067 (U.S. Pat. No. 8,563,038).
Office Action issued on Nov. 14, 2011 in U.S. Appl. No. 12/823,067 (U.S. Pat. No. 8,563,038).
Office Action issued on Oct. 24, 2013 in U.S. Appl. No. 13/928,135 (US 2013/0287849).
Notice of Allowance issued on Aug. 1, 2013 in U.S. Appl. No. 12/078,312 (U.S. Pat. No. 8,609,143).
Office Action issued on May 13, 2013 in U.S. Appl. No. 12/078,312 (U.S. Pat. No. 8,609,143).
Notice of Allowance issued on Jun. 25, 2013 in U.S. Appl. No. 12/073,692 (U.S. Pat. No. 8,617,605).
European Search Report issued on Apr. 11, 2011 in application No. EP 10 18 1692 (corresponding to US 2007/003617).
Office Action issued on Aug. 27, 2013 in U.S. Appl. No. 11/915,655 (US 2009/0274759).

(56) References Cited

OTHER PUBLICATIONS

Kais Group, "Hydrogentated Palm Kernel Oil," http://kaisqroup.us/our-products/palm-oil-products/hydrogentated-palm-kernel-oil. Published 2011.

Soy Info Center, "A Special Report on the History of Soy Oil, Soybean Meal & Modern Soy Protein Products," http://soyinfocenter.com/HSS/hydrogenation2.php, published 2007.

Polysciences, Inc., "Monomers & Polymers," http://www.polysciences.com/Catalog/Department/Product/98/categoryid-298/productid--422/, published Apr. 3, 2004.

Office Action issued on Feb. 6, 2014 in U.S. Appl. No. 13/974,689 (US 2014/0120164).

Office Action issued on Jun. 9, 2011 by the Examiner in U.S. Appl. No. 12/073,691 (US 2008/0234352).

Office Action issued on Apr. 28, 2011 by the Examiner in U.S. Appl. No. 12/073,691 (US 2008/0234352).

Office Action issued on Mar. 31, 2011 by the Examiner in U.S. Appl. No. 12/073,692 (US 2008/0254122).

Office Action issued on Apr. 4, 2011 by the Examiner in U.S. Appl. No. 12/078,312 (US 2008/0254123).

Office Action issued on Feb. 18, 2011 by the Examiner in U.S. Appl. No. 12/076,105 (US 2008/0268057).

Office Action issued on Nov. 24, 2010 by the Examiner in U.S. Appl. No. 12/076,105 (US 2008/0268057).

Packer et al., "Molecular Aspects of α-Tocotrienol Antioxidant Action and Cell Signalling," Journal of Nutrition, vol. 131, No. 2, pp. 369S-373S, 2001.

Wanka et al., "Phase Diagrams and Aggregation Behavior of Poly(oxyethylene)- Poly(oxypropylene)-Poly(oxyethylene) Triblock Copolymers in Aqueous Solutions," Macromolecules, vol. 27, pp. 4145-4159, 1994.

Final Office Action U.S. Appl. No. 10/550,685 dated Feb. 1, 2012.

Notice of Allowance U.S. Appl. No. 10/550,685 dated Jun. 5, 2012.

http://en.wikipedia.org/wiki/Phosphoric_acid downloaded May 10, 2012.

Notice of Allowance issued on Oct. 6, 2010 by the Examiner in U.S. Appl. No. 10/845,522 (US 2008/0254124).

Office Action issued on Mar. 1, 2010 by the Examiner in U.S. Appl. No. 10/550,685 (US 2007/0042044).

Office Action issued on Jun. 18, 2010 by the Examiner in U.S. Appl. No. 12/076,105 (US 2008/0268057).

Office Action issued on Apr. 5, 2010 by the Examiner in U.S. Appl. No. 12/076,105 (US 2008/0268057).

Bravo et al., *J. Pharmaceutical Science*, 5(3) :213-219 (2002).

The Condensed Chemical Dictionary, 9th edition, p. 584 (1977).

Giunchedi et al., "Hydroppilic Matrices for the Extended Release of a Model Drug Exhibiting pH-dependent Solubility," *International Journal of Pharmaceutics*, 85:141-147 (1992).

Hoshi et al., Cellulose and its Derivatives, pp. 24-25 (1992).

Miyazaki et al., "In situ-gelling gellan formulations as vehicles for oral drug delivery," *J. Control Release*, vol. 60, pp. 287-295 (1999).

Rowe et al., *Handbook of Pharmaceutical Excipients*, Pharmaceutical Presse, 4th edition, pp. 257-258 (2003).

www.wikipedia.org, web page on phosphoric acid.

Yamakita et al., "In Vivo Evaluation of Two Series of TA-5707F Controlled Release Matrix Tablets Prepared with Hydroxypropyl Methyl Cellulose Derivatives with Enter0-Soluble or Gel Formation Properties," *Biological and Pharmaceutical Bulletin*, 18 10 ;1409-1416 (1995).

Office Action issued Oct. 24, 2006 by the Examiner in U.S. Appl. No. 10/703,084 (US 2004/0151772).

Office Action issued Jun. 14, 2007 by the Examiner in U.S. Appl. No. 10/703,084 (US 2004/0151772).

Office Action issued Aug. 03, 2006 by the Examiner in U.S. Appl. No. 10/490,169 (US 2004/0253310).

Office Action issued Mar. 2, 2007 by the Examiner in U.S. Appl. No. 10/490,169 (US 2004/0253310).

Office Action issued Dec. 20, 2007 by the Examiner in U.S. Appl. No. 10/827,521 (US 2005/0019405).

Office Action issued Jul. 25, 2006 by the Examiner in U.S. Appl. No. 10/490,308 (US 2004/0234602).

Office Action issued Mar. 9, 2007 by the Examiner in the U.S. Appl. No. 10/490,308 (US 2004/0234602).

Office Action issued Oct. 3, 2006 by the Examiner in U.S. Appl. No. 10/490,170 (US 2005/0019399).

Office Action issued May 9, 2007 by the Examiner in the U.S. Appl. No. 10/490,170 (US 2005/0019399).

Office Action issued Oct. 22, 2002 by the Examiner in U.S. Appl. No. 09/647,590.

Office Action issued May 11, 2001 by the Examiner in U.S. Appl. No. 09/647,590.

Office Action issued Jul. 14, 2003 by the Examiner in U.S. Appl. No. 09/647,590.

Office Action issued Jan. 30, 2002 by the Examiner in U.S. Appl. No. 09/647,590.

Office Action issued Jan. 13, 2009 by the Examiner in U.S. Appl. No. 10/845,522 (US 2007/0042044).

Office Action issued May 14, 2008 by the Examiner in U.S. Appl. 10/845,522 (US 2007/0042044).

Office Action issued Jun. 16, 2006 by the Examiner in U.S. Appl. No. 10/845,522 (US 2007/0042044).

Office Action issued Oct. 27, 2005 by the Examiner in U.S. Appl. No. 10/845,522 (US 2007/0042044).

Office Action issued Jul. 29, 2005 by the Examiner in U.S. Appl. No. 10/845,522 (US 2007/0042044).

Office Action issued Mar. 21, 2007 by the Examiner in U.S. Appl. No. 10/845,522 (US 2007/0042044).

Office Action issued Dec. 15, 2008 by the Examiner in U.S. Appl. No. 12/213,087 (US 2008/0254124).

Office Action issued Dec. 23, 2008 by the Examiner in U.S. Appl. No. 10/550,685 (US 2007/0042044).

Office Action issued Jun. 17, 2009 by the Examiner in U.S. Appl. No. 10/550,685 (US 2007/0042044).

Giunchedi et al., "Hydrophilic Matrices for the extended release of a model drug exhibiting pH-dependent solubility," *International Journal of Pharmaceutics*, vol. 85, pp. 141-147 (1992).

Office Action issued Jan. 13, 2009 by the Examiner in U.S. Appl. No. 10/845,522 (US 2005/0089569).

Office Action issued Jun. 17, 2009 by the Examiner in U.S. Appl. No. 10/550,453 (US 2007/0042044).

Office Action issued Nov. 4, 2009 by the Examiner in U.S. Appl. No. 10/845,522 (US 2005/0089569).

Office Action issued Apr. 29, 2009 by the Examiner in U.S. Appl. No. 12/076,105 (US 2008/0268057).

Office Action issued Sep. 29, 2009 by the Examiner in U.S. Appl. No. 12/076,105 (US 2008/0268057).

Marvola et al., "Enteric polymers as binders and coating materials in multiple-unit site-specific drug delivery systems," *European Journal of Pharmaceutical Sciences*, vol. 7, pp. 259-267, 1999.

Dubbs et al., "Solubility of Vitamin E (α-Tocopheral) and Vitamin $K_3$ (Menadione) in Ethanol-Water Mixture," *J. Chem. Eng. Data*, vol. 43, pp. 590-591, 1998.

Merck Index (9th edition), Entry No. 9681 for Vitamin E, p. 1290, 1976.

Office Action issued Jun. 16, 2009 in U.S. Appl. No. 10/550,453 (U.S. Pat. No. 8,877,241).

Office Action issued Nov. 10, 2009 in U.S. Appl. No. 10/550,453 (U.S. Pat. No. 8,877,241).

Office Action issued Apr. 13, 2010 in U.S. Appl. No. 10/550,453 (U.S. Pat. No. 8,877,241).

Office Action issued Aug. 5, 2010 in U.S. Appl. No. 10/550,453 (U.S. Pat. No. 8,877,241).

Office Action issued Jan. 20, 2011 in U.S. Appl. No. 10/550,453 (U.S. Pat. No. 8,877,241).

Office Action issued Mar. 18, 2014 in U.S. Appl. No. 10/550,453 (U.S. Pat. No. 8,877,241).

Notice of Allowance issued Jul. 3, 2014 in U.S. Appl. No. 10/550,453 (U.S. Pat. No. 8,877,241).

Braga et al., "Crystal Polymorphism and Multiple Crystal Forms," Struct. Bond., vol. 132, pp. 25-50, 2009.

Vippagunta et al., "Crystalline Solids," Advanced Drug Delivery and Reviews, vol. 48, pp. 3-26, 2001.

(56) References Cited

OTHER PUBLICATIONS

Muller, "Polymorphism," Inorganic Structural Chemistry, Chapter 3.1, pp. 14-15, John Wiley & Sons, Apr. 1993.
Office Action issued on Jun. 4, 2015 in U.S. Appl. No. 12/523,045 (US 2010/0291205).
Office Action issued on Dec. 3, 2014 in U.S. Appl. No. 12/523,045 (US 2010/0291205).
Office Action issued on Jan. 20, 2015 in U.S. Appl. No. 13/933,053 (US 2014/0010873).
Notice of Allowance issued on Jan. 23, 2015 in U.S. Appl. No. 12/701,248 (U.S. Pat. No. 9,005,660).
Office Action issued on Sep. 10, 2014 in U.S. Appl. No. 12/694,197 (US 2010/0203129).
Notice of Allowance issued on Jan. 20, 2015 in U.S. Appl. No. 13/928,135 (U.S. Pat. No. 9,023,394).
Notice of Allowance issued on Sep. 17, 2014 in U.S. Appl. No. 13/928,135 (U.S. Pat. No. 9,023,394).
Notice of Allowance issued on Apr. 6, 2015 in U.S. Appl. No. 14/249,965 (U.S. Pat. No. 9,044,402).
Office Action issued on Dec. 10, 2014 in U.S. Appl. No. 14/249,965 (U.S. Pat. No. 9,044,402).
Notice of Allowance issued on Jun. 23, 2015 in U.S. Appl. No. 14/062,719 (US 2014/0050787).
Office Action issued on Nov. 7, 2014 in U.S. Appl. No. 13/928,190 (US 2013/0287850).
Office Action issued on Mar. 6, 2015 in U.S. Appl. No. 14/331,833 (US 2015/0037417).
Office Action issued on Apr. 24, 2015 in U.S. Appl. No. 11/915,655 (US 2009/0274759).
Notice of Allowance issued on Jun. 23, 2015 in U.S. Appl. No. 14/062,719 (U.S. Pat. No. 9,168,228).
Office Action issued on Sep. 10, 2015 in U.S. Appl. No. 14/446,234 (US 2015/0024048).
Office Action issued on Feb. 25, 2015 in U.S. Appl. No. 13/974,689 (US 2014/0120164).

\* cited by examiner

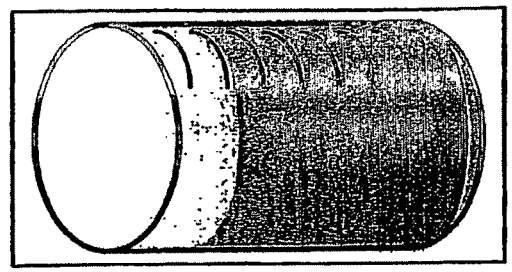
Fig. 1A
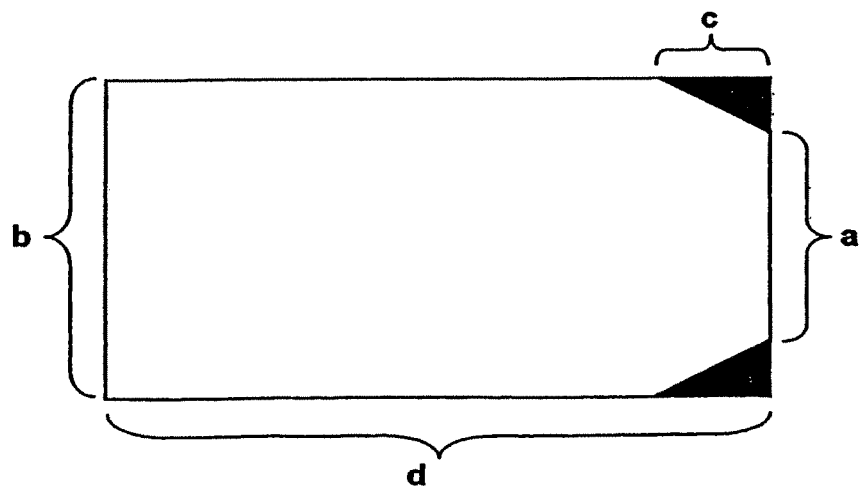
Fig. 1B
Fig. 1

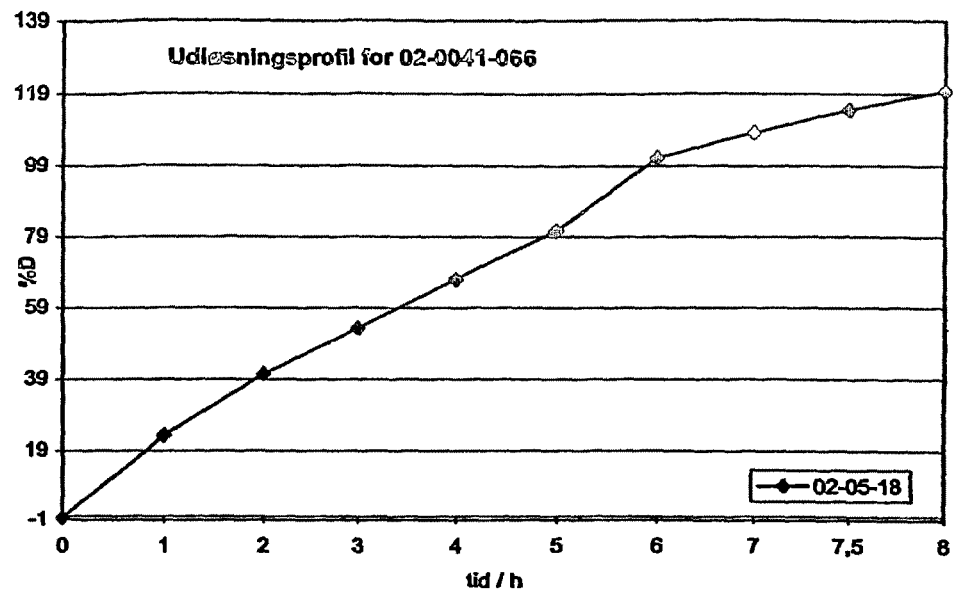
Fig 3-1A
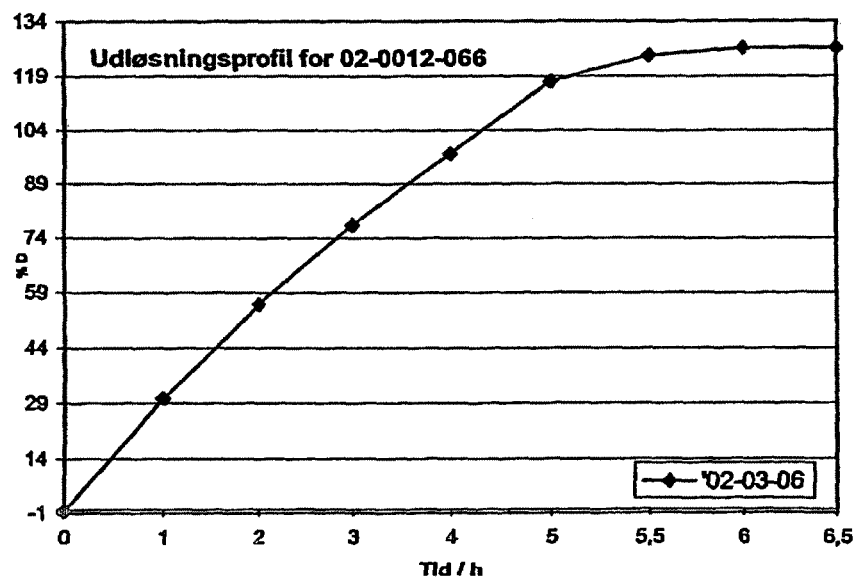
Fig 3-1B
Fig. 3

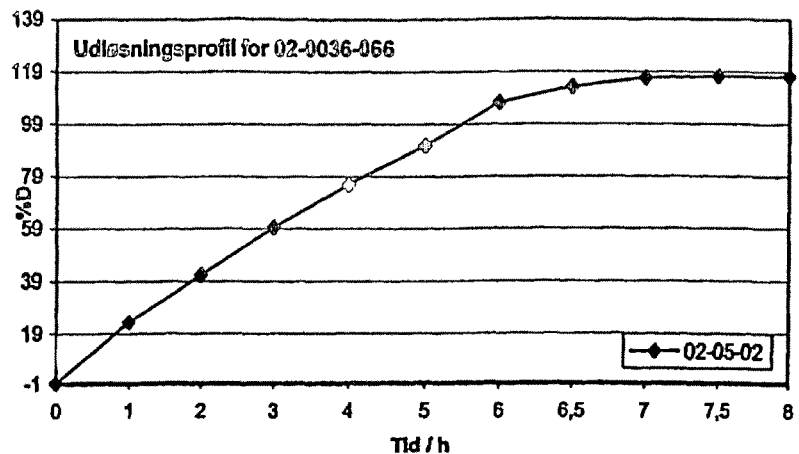
Fig 3-2A
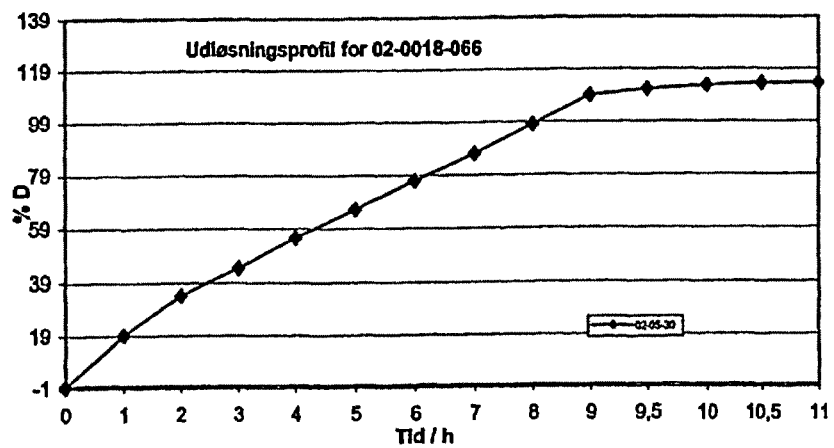
Fig 3-2B
Fig. 3

MORPHINE CONTROLLED RELEASE SYSTEM

FIELD OF THE INVENTION

The present invention relates to a novel pharmaceutical composition for controlled release of an opioid like e.g. morphine into an aqueous medium. The pharmaceutical composition is a coated matrix composition in which the matrix composition comprises a) a polymer or a mixture of polymers, b) an opioid like e.g. morphine and, optionally, c) one or more pharmaceutically acceptable excipients. The coating remains intact during the release phase and may thereafter crumble and/or erode. Furthermore, the coating covers the matrix composition in such a manner that only a specific surface area of the matrix composition is subject to erosion in an aqueous medium, i.e. the surface area from which the active substance is release is kept substantial constant during the time period.

The polymer mentioned under a) above may suitably be a substantially water soluble or crystalline polymer or a mixture of substantially water soluble and/or crystalline polymers The design of the pharmaceutical composition is based on the finding that it is possible to control the release from such a composition by ensuring that the release predominantly takes place by erosion. In order to ensure erosion based release a balance must be obtained between the diffusion rate of water into the matrix composition and the dissolution rate of the matrix composition.

Accordingly, the invention relates to an opioid containing pharmaceutical composition for oral use, which provides zero order release based on controlling the balance between matrix erosion rate and diffusion rate in the matrix.

The invention also provides various combinations of immediate release opioid compositions and controlled release opioid compositions.

DISCLOSURE OF THE INVENTION

The present invention relates to a controlled release composition comprising an opioid as a therapeutically, prophylactically and/or diagnostically active substance. The opioids are generally used in analgesic treatment and there is a need for developing compositions for oral use, which have a lower administration frequency. Thus once or twice daily administrations would be preferred. A controlled release composition according to the invention aims at a zero order release of the opioid in a predetermined pattern to reduce and/or delay the peak plasma concentration without affecting the extent of drug bioavailability. The frequency of undesirable side effects may be reduced and due to the delay in the time it may take to obtain the peak plasma concentration and the extension of the time at the therapeutically active plasma concentration, the frequency of the administration may be reduced to a dosage taken only twice or once daily. This also serves to improve patient compliance. A further advantage of the controlled release composition is that high local concentrations of the opioid in the gastrointestinal tract are avoided due to the erosion-based release mechanism.

Patients suffering from chronic pains very often require a high daily dosage of an analgesic. If such a high dosage of an opioid should be given only once or twice daily, the release from the composition must be safe. The composition should also be storage stable with respect to chemical and physical stability.

Morphine is probably one of the most commonly used analgesics in the control of severe pain. Due to the short half-life of morphine of approximately 2 hours, the analgesic must be administered frequently, e.g. every 3-4 hours to maintain a patient pain free. This regime may require a 2 a.m. dose to prevent early morning recurrence of pain.

To obtain therapeutic plasma concentrations with less frequent dosing, effective controlled release analgesics are under continuous development. An ideal controlled release analgesic should exhibit the following properties: prevent pain "break-through", eliminate major plasma concentration fluctuations, produce prolongation of effective drug levels, produce effective analgesia without unwanted side effects such as sedation.

In other words, in addition to a less frequent administration, the real challenge in controlled release delivery may be expressed by the goal of decreasing the incidence of adverse effects and at the same time increasing the effect of the treatment. This can only be obtained by an interaction between the specific pharmacological properties of the active ingredient and the composition.

Many controlled release products on the market suffers from the lack of a true controlled release. In fact, Dolcontin®, which covers most of the market for sustained morphine, results in a plasma profile rather similar with an immediate release dosage formulation only with a slight decrease in the initial burst. During the repeated administration, the plasma concentration with this product will necessarily exhibit the undesired peaks and troughs as is also shown in FIG. 18 comparing the commercial twice daily MS Contin with the commercial available Kadian multiple pellet formulation, both demonstrating a fluctuation during the day where the minimum concentration is less than half of the maximal concentration for each of the two formulations. Such degree of fluctuation in concentration during the dosing interval may be avoided with the opioid composition according to the present invention.

Controlled release is not only the effect of prolonging the release of active ingredient from the composition by increasing the dosage and decreasing the initial burst. The optimised effect is only obtained when the right balance is obtained between the maximum concentration, the duration of the time where the plasma concentration is above the minimum therapeutic level and the administered dosage.

High concentrations or a fast rise in the concentration of morphine is one important factor resulting in side effects including the risk of getting addicted to morphine. The fear of addiction is often a major obstacle for initiation of the otherwise effective pain treatment with morphine both in the view of the clinical personnel as well as in the view of the patients themselves.

High concentrations during longer periods induce resistance on receptor level and should also be avoided. By "high" is here meant any plasma concentration above the pain relieving level. Other important side effects of morphine are the respiratory depressing effect and sedation; both are highly correlated to the plasma concentration. In addition, memory and motor control, important aspects in relation with long term treatment, may already be present within the therapeutic level and accordingly, any unnecessary high concentration of morphine should be avoided.

According to the present invention it is possible to obtain a composition, which is effective in treating pain and at the same time have one or more of the following advantages: a relative low maximal serum concentration of the opioid and pain relieving effect, relative decreased average serum concentrations but still pain relieving effect, minimal concentrations of opioid but still pain relieving effect. Each of these factors may be associated with a minor risk of side effects. This conclusion is to be supported by less frequently reported side effects by the patients receiving such a composition in a clinical study comparing controlled release compositions having a non-zero order dissolution profile. Adverse events to be reported in such study include sedation, nausea, dizziness, vertigo, obstipation, urine retention, itching, perspiration, and dry mouth. It is generally acknowledged that the most of the broad variety of adverse effects of morphine correlate with the dosage.

Accordingly, a limitation of the maximal concentration as well as the duration of a sufficient concentration is of great benefit for every patient. On the other hand, in chronic pain treatment with morphine, too low concentrations will immediately result in the need for additional rescue medication leading to an increase in the overall dosage, and in the end, to a higher incident of dose dependent side effects. Also in this respect, a formulation according to the present invention is expected to result in the decrease in maximal concentration without a decrease in pain relieving effect. If the controlled release composition is not optimal, the final treatment regimen for the patient including the rescue medication may resemble an ordinary treatment and only few benefits are obtained.

With respect to safety and side effects, many controlled release formulations are only compared with immediate release formulations. The formulation according to the present invention addresses all the problems of a sustained release formulation by releasing a steady and accurately predictable flow of the opioid as clearly supported by the dissolution profiles shown herein.

The term "opioid" as used herein denotes a group of active substances that are, to a varying degree, opium- or morphine-like in their properties. The term includes natural and synthetic opioids as well as active metabolites such as, e.g. morphine 6-glucuronide, morphine 3-glucuronide, and mixtures thereof. Pharmaceutically acceptable salts, complexes, solvates and anhydrates thereof, and mixtures thereof are also within the definition of opioids.

In those cases, where the active substance is dispersed in the matrix, it is present in any of its crystalline, polymorphous or amorphous forms or mixtures thereof.

In specific embodiments, the active substance may at least partially be present in solid form in the dispersion, i.e. some of the active substance may be dissolved in the polymer (such as, e.g., polyethylene oxide) provided that at least a part is still present on solid form.

In the pharmaceutical technology (and in the present context), the term "solid dispersion" also embraces semi-solid dispersions. By the term is understood the finely dispersed distribution of one or more solids, e.g. an active substance like morphine, in an inert solid or semi-solid carrier. The active substance may be present in molecular dispersed form, i.e. as a solid solution, in fine crystalline dispersed form, in a glassy amorphous phase or dispersed as a fine amorphous powder. Eutectic mixtures, i.e. crystalline structures of active substances and carriers are also encompassed in the definition of "solid dispersions". Normally, the mean particle size is used to classify dispersed system. A colloidal dispersion is when the dispersed phase has a particle size between about 1 and about 1000 nm and a coarsely dispersion has a mean particle size of at least about 1000 nm and a molecular dispersion has a particle size below about 1 nm. Combinations between the various states are very likely and the most dominating character can be determined by X-ray diffraction spectra or differential thermoanalysis.

In specific aspects of the present invention some of the active substance may be present in a molecular dispersion such as, e.g., in the form of a solid or semi-solid solution.

In a preferred aspect of the invention, a composition comprises morphine that at least partially is present in amorphous form with a mean particle size of at least about 0.01 μm such as, e.g., from about 0.01 μm to about 500 μm, from about 0.05 μm to about 500 μm, from about 0.1 μm to about 500 μm, from about 0.5 μm to about 500 μm, about 1 μm to about 500 μm, typically from about 0.5 μm to about 300 μm, more typically from about 1 μm to about 200 μm, especially from about 1 μm to about 100 μm.

In general, the opioids are readily absorbed from the gastrointestinal tract after oral administration. Many opioids like e.g. morphine are subject to a first-pass metabolism in the liver. The half-life of morphine is about 1.5 to 2 hours, but morphine is metabolised to active metabolites, which have a longer half-life. The average duration of action of a single dose of 10 mg of e.g. oral morphine is about 4-5 hours (given as a plain tablet composition).

The dosage of the opioid(s) contained in a controlled release composition according to the invention depends on the particular opioid in question. With respect to morphine an amount corresponding to from about 5 to about 800 mg of morphine sulfate is suitable. Alternatively, the dosage form (i.e. the composition) may contain a molar equivalent amount of another morphine salt (i.e. the hydrochloride etc.).

Examples of opioids suitable for use in a composition according to the present invention are:

Alfentanil, allylprodine, alphaprodine, aniloridine, benzylmorphine, bezitramide, buprenorphine, butophanol, clonitazene, codeine, cyclazocine, desomorphine, dextromoramide, dezocine, diapromide, dihydrocodeine, dihydromorphine, dimenoxadol, dimephetanol, dimethylthiambutene, dioxaphetyl butyrate, dipipanone, eptazocine, ethoheptazine, ethylmethylthiambutene, ethylmorphine, etonitazene, fentanyl, heroin, hydrocodone, hydromorphone, hydroxypethidine, isomethadone, dextropropoxyphene, ketobemidone, levallorphan, levorphanol, levophenacylmorphan, lofentanil, meperidine, meptazinol, metazocine, methadone, metopon, morphine, morphine 6-glucuronide, morphine 3-glucuronide, myrophine, nalbuphine, narccine, nicomorphine, norlevorphanol, normethadone, nalorphine, normorphine, norpipanone, opium, oxycodone, oxymorphone, papaveretum, pentazocine, phenadoxone, phenomorphan, phenazocine, phenoperidine, piminodine, piritramide, propheptazine, promedol, properidine, propiram, propoxyphene, sufentanil, tilidine, tramadol, and pharmaceutically acceptable salts, complexes, solvates or anhydrates thereof, and mixtures thereof.

Preferred embodiments of the invention are compositions containing an opioid selected from the group consisting of morphine oxycodone, oxymorphone, hydrocodone, hydromorphone and dihydromorphine.

The term "pharmaceutically acceptable salts" of an opiod includes alkali metal salts such as, e.g., sodium or potassium salts, alkaline earth metal salts such as, e.g., calcium and magnesium salts, and salts with organic or inorganic acid like e.g. hydrochloric acid, hydrobromic acid, nitric acid, sulfuric acid, phosphoric acid, citric acid, formic acid, maleic acid, succinic acid, tartaric acid, methansulphonic acid, toluenesulphonic acid etc.

The term "solvates" includes hydrates or solvates wherein other solvates than water are involved such as, e.g., organic solvents like chloroform and the like.

Furthermore, the opioid such as morphine may be in any of its crystalline, polymorphous or amorphous forms.

The present inventors have applied a novel method for controlling the release of an active substance from a pharmaceutical composition. The method involves controlling the release of at least one therapeutically, prophylactically and/or diagnostically active substance into an aqueous medium by erosion of at least one surface of a pharmaceutical composition comprising i) a matrix composition comprising a) polymer or a mixture of polymers, b) an active substance and, optionally, c) one or more pharmaceutically acceptable excipients, and
ii) a coating having at least one opening exposing at the one surface of said matrix, the coating comprising
    a) a first cellulose derivative which has thermoplastic properties and which is substantially insoluble in the aqueous medium in which the composition is to be used,
and at least one of
    b) a second cellulose derivative which is soluble or dispersible in water,
    c) a plasticizer, and
    d) a filler,
the method comprising adjusting the concentration and/or the nature of the ingredients making up the matrix composition in such a manner that the diffusion rate of the aqueous medium into the matrix composition corresponds to about 100%±30% such as, e.g. about 100%±25%, about 100%±20%, about 100%±15% or about 100%±10% or about 100% of the dissolution rate of the matrix composition so as to obtain a zero order release of at least about 60% w/w such as, e.g. at least about 65% w/w at least about 70% w/w, at least about 75% w/w, at least about 80% w/w, at least about 85% w/w, at least about 90% w/w, at least about 95% w/w or at least about 97 or 98% w/w of the active substance from the pharmaceutical composition when subject to an in vitro dissolution test as described herein.

Accordingly, the present invention relates to a pharmaceutical composition for controlled release of at least one opioid into an aqueous medium by erosion of at least one surface of the composition, the composition comprising
    i) a matrix composition comprising a) a polymer or a mixture of polymers, b) an active substance and, optionally, c) one or more pharmaceutically acceptable excipients, and
    ii) a coating having at least one opening exposing at the one surface of said matrix, the coating comprising
        a) a first cellulose derivative which has thermoplastic properties and which is substantially insoluble in the aqueous medium in which the composition is to be used,
    and at least one of
        b) a second cellulose derivative which is soluble or dispersible in water,
        c) a plasticizer, and
        d) a filler,
    wherein the matrix composition has a conus-like shape so that the surface area exposed to the aqueous medium increases at least during initial erosion of the matrix composition, and
    the dissolution of the opioid—when tested in a Dissolution Test as described herein with or without application of sinkers—results in a zero order release of at least 80% of the opioid contained in the composition.

Due to the shape and the release mechanism, a composition according to the invention has suitable therapeutic properties in the treatment of diseases or conditions, wherein an opioid is prescribed (cf. the Examples herein relating to clinical studies)

Details concerning the method and the pharmaceutical compositions are described herein.

In a specific embodiment of the invention the polymer mentioned under a) is a substantially water soluble or crystalline polymer or a mixture of substantially water soluble and/or crystalline polymers.

Controlled Release

During the last decades many different systems for modifying the release of an active drug substance from a pharmaceutical composition have been developed. Most of them aim at obtaining a zero or a first order release rate of the active substance from the composition. Zero order release rate (i.e. constant release of the active substance with time) seems to be very difficult to obtain from a pharmaceutical composition. The present invention is based on a polymeric matrix composition, which is construed to deliver the active substance in a zero order release manner. The present invention is a further development based on the Applicant's previously described drug delivery systems, see e.g. EP-B-0 406 315, EP-B-0 493 513, EP-B-0 740 310 and WO 99/51208 the disclosure of which is hereby incorporated by reference.

In particular, it has surprisingly been found that it is possible to obtain zero order release from a polymeric matrix composition without any content of a water dispersible or water soluble surface active agent or a mixture of such surface active agents which has at least one domain which is compatible with the polymer in the polymer matrix composition and at least one other domain which is substantially lipophilic and which has a melting point that is lower than the polymer used in the polymeric matrix composition. The presence of such a substance (e.g. like PEG 400 monostearate or PEG 2000 monostearate) has been contemplated to function as a so-called repair medium. Such a repair medium has a substantially hydrophilic domain, which gives it affinity to the (crystalline) polymeric phase, thereby filling in domains between grains and cracks in the polymer matrix and reducing the water affinity of these domains and in the polymer matrix itself. Water diffusion in the interface between the polymer crystals is thereby substantially eliminated, thus substantially limiting diffusion of water into the composition to the surface layer of the matrix, so that erosion of the composition is predominantly effected by the dissolving action of the aqueous phase on a surface or surfaces of the composition exposed to the aqueous medium. In other words a repair medium seems to prevent the diffusion of water in the polymer matrix composition.

However, in certain cases, the present inventors have observed that inclusion of a water soluble surface active agent may have a negative impact on the mobility and/or stability of a composition. However, it seems as if the problems arise when the concentration of the surface active agent is relatively high and/or when the surface active agent has a HLB value of less than 16.

The present inventors have found that it is possible to obtain a zero order release from a polymer matrix composition although water may be able to diffuse into the matrix. When water diffuse into the polymer matrix composition a resulting boundary layer (or swelling layer) can be formed at the surface of the matrix composition, which is exposed to the aqueous medium. In general the diffusion of an active substance through such a boundary layer is important for the release of an active substance and, accordingly, the thickness of the boundary layer is important for the release rate. However, the present inventors have found that it is possible to eliminate or substantially eliminate the impact of the boundary layer on the release rate of the active substance from a polymer matrix composition by ensuring that the thickness of the boundary layer is relatively small and/or that the release of the active substance from a polymer matrix composition is governed by erosion of the composition and the diffusion of the active substance through the boundary layer, if any, has no or only a small impact on the overall release rate.

The present inventors have found that when water is allowed to diffuse into a polymer matrix composition zero order release is obtained when the release rate is governed or controlled by erosion of a constant surface area per time unit. In order to ensure that the erosion of the polymer matrix composition is the predominant release mechanism, the inventors have found that it is necessary to provide a polymer matrix composition which has properties that ensures that the diffusion rate of water into the polymer matrix composition substantially corresponds to the dissolution rate of the polymer matrix composition into the aqueous medium. Thus, by adjusting the nature and amount of constituents contained in the polymer matrix composition along this line the present inventors have obtained polymer matrix compositions, which release the active substance by a zero order release mechanism. The compositions employed are coated in such a manner that at least one surface is exposed to the aqueous medium and this surface has a substantially constant or controlled surface area during erosion. In the present context controlled surface area relates to a predetermined surface area typically predicted from the shape of the coat of the unit dosage system. It may have a simple uniform cylindrical shape or the cylindrical form can have one or more tapered ends in order to decrease (or increase) the initial release period.

As it appears from the above, the invention relates specifically to pharmaceutical compositions comprising an opioid as an active substance and wherein the above-mentioned principle has been applied.

Besides providing a pharmaceutical composition, the present invention also employs a method for controlling the release of at least one opioid into an aqueous medium by erosion of at least one surface of a pharmaceutical composition comprising
i) a matrix composition comprising a) polymer or a mixture of polymers, b) an opioid and, optionally, c) one or more pharmaceutically acceptable excipients, and
ii) a coating having at least one opening exposing at the one surface of said matrix, the coating comprising
    a) a first cellulose derivative which has thermoplastic properties and which is substantially insoluble in the aqueous medium in which the composition is to be used,
and at least one of
    b) a second cellulose derivative which is soluble or dispersible in water,
    c) a plasticizer, and
    d) a filler,
the method comprising adjusting the concentration and/or the nature of the ingredients making up the matrix composition in such a manner that the diffusion rate of the aqueous medium into the matrix composition corresponds to about 100%±30% such as, e.g. about 100%±25%, about 100%±20%, about 100%±15% or about 100%±10% or about 100% of the dissolution rate of the matrix composition so as to obtain a zero order release of at least about 60% w/w such as, e.g. at least about 65% w/w at least about 70% w/w, at least about 75% w/w, at least about 80% w/w, at least about 85% w/w, at least about 90% w/w, at least about 95% w/w or at least about 97 or 98% w/w of the active substance from the pharmaceutical composition when subject to an in vitro dissolution test as described herein.

As mentioned above, in a specific embodiment of the invention, the polymer a) is a substantially water soluble or crystalline polymer or a mixture of substantially water soluble and/or crystalline polymers.

By use of such a method it is possible already during the developmental work to test various polymer matrix compositions with respect to diffusion rate of water into the composition and to dissolution rate of the polymer matrix composition in an aqueous medium. Based on such results adjustment of e.g. the concentration and/or nature of the individual constituents in the composition may be performed until the diffusion rate balance the dissolution rate. In such a manner, a relatively simple instrument has been provided in order to ensure a zero order release rate from the final composition.

In another aspect, the invention relates to a pharmaceutical composition for controlled release of at least one opioid into an aqueous medium by erosion of at least one surface of the composition, the composition comprising
i) a matrix composition comprising a) a polymer or polymers, b) an opioid and, optionally, c) one or more pharmaceutically acceptable excipients, and
ii) a coating having at least one opening exposing at the one surface of said matrix, the coating comprising
    a) a first cellulose derivative which has thermoplastic properties and which is substantially insoluble in the aqueous medium in which the composition is to be used,
and at least one of
    b) a second cellulose derivative which is soluble or dispersible in water,
    c) a plasticizer, and
    d) a filler,
    wherein the matrix composition has a conus-like shape so that the surface area exposed to the aqueous medium increases at least during initial erosion of the matrix composition, and
the dissolution of the opioid—when tested in a Dissolution Test as described herein with or without application of sinkers—results in a zero order release of at least 80% of the opioid contained in the composition In the above-mentioned composition the concentration and/or the nature of the ingredients making up the matrix composition have been adjusted in such a manner that the diffusion rate of the aqueous medium into the matrix composition corresponds to about 100%±30% such as, e.g. about 100%±25%, about 100%±20%, about 100%±15% or about 100%±10% or 100% of the dissolution rate of the matrix composition so as to obtain a zero order release of at least about 60% w/w such as, e.g. at least about 65% w/w at least about 70% w/w, at least about 75% w/w, at least about 80% w/w, at least about 85% w/w, at least about 90% w/w, at least about 95% w/w or at least about 97 or 98% w/w of the active substance from the pharmaceutical composition when subject to an in vitro dissolution test as described herein.

Shape

The geometric form of the composition is very important for the obtainment of the above-mentioned controlled zero order. Thus, in one embodiment of the invention, the pharmaceutical composition has a geometric shape, which enables a substantially constant surface area to become exposed during erosion of the matrix.

However, in order to achieve a higher plasma concentration 5-10 hours after administration the clinical studies reported herein have demonstrated that a shape is suitable that exposes an increasing surface area at least during the initial erosion of the matrix such as e.g. during the 0.5 hour, during the first hour, during the first 2 hours, during the first 3 hours, during the first 5 hours or during the first 6 hours and then, if desired, exposes a constant surface area. Examples of such shapes are given in FIG. 1B and are herein denoted "conus shape".

In an specific embodiment, the increase in surface area relates to an increase in diameter of the surface area of at least one exposed surface area upon erosion of that surface, and the ratio between the largest and smallest diameter is decreasing from about 2.5 to 1 during the erosion, such as from about 2 to 1, such as from as from about 1.8 to 1, such as from about 1.6 to 1, such as from as from about 1.5 to 1, such as from about 1.4 to 1 such as from about 1.3 to 1, such as from about 1.2 to 1.

It is clear that the time during the erosion where the ratios between the largest and smallest diameter are decreasing is dependent on the length of the conus in the matrix composition. For a shorter duration of decreased release, the conus may be present in 5% to 25% of the total length of the matrix composition and for a longer decrease in 30% to 50% of the total length when a constant increase in release is desired during the full release period. In some cases, the conus end of the matrix composition may erode at slightly slower rate due to less erosion forces present within the narrower opening of the coat at the end of the composition comprising the smallest exposed surface. In other words, the cone need not be of a 50% length in order to obtain a constant increasing release during the total release period.

Another embodiment of the invention is where the ratio between the areas of the two exposed surfaces is substantial constant during erosion, in other words, where a conus shape is present in both ends of the matrix composition. In such cases the increase in surface area during erosion may be 50%, such as 100%, such as 150%, such as 200%, such as 250%, e.g. 300% or as much as 400% compared to the exposed surface area present before erosion of said surfaces.

Without limiting the invention hereto, specific examples of compositions with different shapes and sizes are shown in the tables below. Table A demonstrates the specific dimensions of compositions according to the invention, wherein one end of the tubular shape has a cone configuration and dimensions according to FIG. 1B and as follows:

TABLE A (confer FIG. 1B)

| D mm | B mm | A mm | C mm | Volume $mm^2$ | Cone Shape |
|---|---|---|---|---|---|
| D 9.00 | B 4.89 | A 3.00 | C 3.00 | 150.00 | 1 |
| D 10.00 | B 4.63 | A 3.00 | C 3.50 | 150.00 | 2 |
| D 10.00 | B 4.63 | A 3.50 | C 4.85 | 150.00 | 3 |
| D 11.00 | B 4.29 | A 3.50 | C 3.50 | 150.00 | 4 |
| D 9.00 | B 4.81 | A 3.50 | C 3.00 | 150.00 | 5 |

Other specific shapes in accordance with FIG. 1B are:

| Batch | Length [mm] | Diameter [mm] | Vol [$mm^3$] |
|---|---|---|---|
| 01-0034-042 | 7.5 | 5.05 | 150 |
| 01-0035-042 | 6.0 | 5.64 | 150 |
| 01-0043-042 | 9.0 | 4.6 | 150 |

The following table describes compositions having a cylindrical form and oval openings in both ends

| Batch | Length [mm] | Vol [$mm^3$] | Largest/shortest diameter [mm] | |
|---|---|---|---|---|
| 01-0075-042 | 6.0 | 150 | 8.74 | 3.64 |
| 01-0076-042 | 7.5 | 150 | 7.82 | 3.21 |

The coated compositions obtained were open at two opposite ends.

The area for an open end is calculated as the volume/length of the cylindrical formulations.

As demonstrated in the Examples herein, the present inventors have found that—by using the technology described herein—it is possible to achieve a zero order release during release of at least 80% of the opioid present in the composition even if the surface area is not constant during the whole release period.

The combination of a specific shape and the zero order release for most of the opioid contained in the composition is especially suitable in those situations where it is desired to delay the appearance of the peak concentration of opioid after oral administration and at the same time it is desired to obtain a prolonged therapeutic effect.

In Vivo Behaviour

The present inventors have performed a number of clinical studies with compositions containing morphine (as an example of an opioid) in order to demonstrate the usefulness of the present technology. From these examples it appears that the combination of the two parameters mentioned above, namely the shape of the composition and the zero order release rate during at least most of the release period is essential for obtaining the desired delay in peak concentration and a prolonged effect.

As demonstrated herein, specific embodiments of the invention are compositions wherein the plasma concentration after oral administration is maintained at a therapeutically effective level for a prolonged time period and at the same time the peak concentration is decreased (compared to e.g. a plain tablet composition) in order to avoid side effects that are related to high plasma concentrations. Accordingly, specific compositions according to the invention are compositions i) wherein the mean plasma concentration 8 hours after oral administration to at least 6 healthy adult humans is at least 40% of the mean maximal concentration obtained by the dose, such as, e.g., at least 50% or at least 60% of the mean maximal concentration, ii) wherein the mean plasma concentration 10 hours after oral administration to at least 6 healthy adult humans is at least 35% of the mean maximal concentration obtained by the dose, such as, e.g., at least 40% or at least 50% of the mean maximal concentration, and/or iii) wherein the mean plasma concentration 12 hours after oral administration to at least 6 healthy adult humans is at least 25% of the mean maximal concentration obtained by the dose, such as, e.g., at least 30%, at least 35% at least 40% or at least about 45% of the mean maximal concentration.

A pharmaceutical composition according to the invention is intended administration once or twice daily. In a specific embodiment, the composition is intended for administration once daily.

Further embodiments of the invention includes pharmaceutical compositions, i) wherein the mean plasma concentration after oral administration of a single dose to at least 6 healthy adult humans is at least 33% of the mean maximal concentration for at least 15 hours such as, e.g., for at least 17 hours, for at least 19 hours or for at least 20 hours.

ii) wherein the mean plasma concentration after oral administration of a single dose to at least 6 healthy adult humans is at least 50% of the mean maximal concentration for at least 6 hours such as, e.g., for at least 8 hours, for at least 9 hours, for at least 10 hours or for at least 11 hours, iii) wherein the mean plasma concentration after oral administration of a single dose to at least 6 healthy adult humans is at least 75% of the mean maximal concentration for at least 3 hours such as, e.g., for at least 3.3 hours, for at least 3.5 hours, for at least 3.7 hours or for at least 3.9 hours, and/or iv) wherein the mean plasma concentration 12 hours after oral administration of a single dose is at least 20% such as, e.g., at least 25% or at least 30% of the mean maximal concentration, and/or the mean plasma concentration 18 hours after oral administration is at least 20% such as, e.g., at least 25%, at least 30% or at least 35% of the mean maximal concentration, and/or the mean plasma concentration 24 hours after oral administration is at least 20% such as, e.g., at least 25% or at least about 30% of the mean maximal concentration.

In Vitro Behaviour

An important method for testing whether a pharmaceutical composition releases the opioid by a zero order release mechanism is by subjecting the composition to a dissolution test e.g. in accordance with pharmacopoeia standards. The present inventors have found that release patterns as those described below are suitable in order to obtain the desired therapeutic effect.

In specific aspects, the invention provides a composition i) wherein about 50% w/w of the opioid is released from the composition within 3-5 hours as measured by the dissolution test described herein, ii) wherein about 75% w/w of the opioid is released from the composition within 4-10 hours as measured by the dissolution test described herein, iii) wherein the composition—when tested in an in vitro dissolution system according to USP (paddle, 50 rpm, buffer pH 6.8 without sinkers)—releases at least about 80% w/w of the total amount of the opioid in a time period of from about 5 to about 10 hours such as, e.g., from about 6 to about 9 hours such as e.g from about 7 to 8 hours or about 7.5 hours after start of the test, iv) wherein the composition—when tested in an in vitro dissolution system according to USP (paddle, 50 rpm, buffer pH 6.8 with sinkers)—releases at least about 80% w/w of the total amount of the opioid in a time period of from about 4 to about 9 hours such as, e.g., from about 5 to about 8 hours such as e.g from about 6 to 7 hours or about 6 hours after start of the test, v) wherein the composition—when tested in an in vitro dissolution system according to USP (paddle, 50 rpm, buffer pH 6.8)—releases the opioid so that when 30% of the time to release at least about 80% w/w of the total amount of the opioid is reached—then from about 10% to about 50% such as, e.g., from about 15% to about 40% w/w, from about 20% to about 30% or about 23-27% w/w is released, vi) wherein the composition—when tested in an in vitro dissolution system according to USP (paddle, 50 rpm, buffer pH 6.8)—releases the opioid so that when 50% of the time to release at least about 80% w/w of the total amount of the opioid is reached—then from about 20% to about 60% w/w such as, e.g., from about 30% to about 50% w/w or about 42-47% w/w is released, vii) wherein the composition—when tested in an in vitro dissolution system according to USP (paddle, 50 rpm, buffer pH 6.8)—releases the opioid so that when 60% of the time to release at least about 80% w/w of the total amount of the opioid is reached—then from about 30% to about 80% w/w such as, e.g., from about 40% to about 70% w/w, from about 50 to about 60% or about 52-58% w/w is released, and/or viii) wherein the composition—when tested in an in vitro dissolution system according to USP (paddle, 50 rpm, buffer pH 6.8)—releases the opioid in the following manner:

within the first 2 hours after start of the test from about 0 to about 30% w/w of the opioid is released, within the first 5 hours after start of the test from about 25% to about 80% w/w of the opioid is released, within the first 7 hours after start of the test from about 40% to about 100% w/w of the opioid is released.

In an especially interesting embodiment a composition according to the invention has a dissolution pattern that resembles that of FIG. 21 herein, the composition being tested under similar conditions.

In another embodiment, a composition according to the present invention is a composition, wherein the release rate measured from the release curve as the time where from 0% to 40% is released is the same or slower as the rate measured for the release from 40% to 80% of the total release.

As mentioned before, in a specific embodiment, the polymer a) is a substantially water soluble or crystalline polymer or a mixture of substantially water soluble and/or crystalline polymers.

Matrix Composition

The pharmaceutical composition according to the invention comprises a matrix composition comprising a) a polymer or a mixture of polymers,
b) an opioid and, optionally,
c) one or more pharmaceutically acceptable excipients.

In a specific embodiment, the polymer is a substantially water soluble or crystalline polymer or a mixture of substantially water soluble and/or crystalline polymers.

Polymers

Suitable polymers for use according to the invention typically comprises a polyglycol, e.g. in the form of a homopolymer and/or a copolymer. In a specific embodiment the polymer is substantially water soluble or crystalline polymer or a mixture of substantially water soluble and/or crystalline polymers. Suitable polymers for use in a composition according to the invention are polyethylene oxides and/or block copolymers of ethylene oxide and propylene oxide. Polyethylene oxides which are suitable for use in the matrix composition are those having a molecular weight of from about 20,000 daltons, such as, e.g., from about 20,000 to about 700,000 daltons, from about 20,000 to about 600,000 daltons, from about 35,000 to about 500,000 daltons, from about 35,000 to about 400,000 daltons, from about 35,000 to about 300,000 daltons, from about 50,000 to about 300,000 daltons, such as, e.g. about 35,000 daltons, about 50,000 daltons, about 75,000 daltons, about 100,000 daltons, about 150,000 daltons, about 200,000 daltons, about 250,000 daltons, about 300,000 daltons or about 400,000 daltons.

A particular suitable polyethylene oxide is one, which in itself has a suitable balance between the diffusion rate of water into the polymer and a dissolution rate of the polymer. Suitable examples are polyethylene oxides having a molecular weight of about 35,000 daltons, about 50,000 daltons, about 100,000 daltons, about 200,000 daltons, about 300,000 daltons and about 400,000 daltons.

Poloxamers are copolymers or block copolymers and are a range of non-ionic surfactants of ethylene oxide (EO) and propylene oxide (PO). The composition can be a PO block flanked by polyethylene oxide chain, generating two primary functional hydroxyls or a reversed structure, where a central EO block is sandwiched between a polypropylene glycol group, resulting in an overtone of secondary hydroxyl end groups.

In chemical abstracts Dial EO/PO block copolymers are described under the scientific name—hydroxy-hydroxypoly(oxyethylene)poly(oxypropylene)-poly(oxyethylene)-block copolymer in combination with the CAS register number.

Examples of specific block-copolymers suitable for use in a composition of the invention are:

Poloxamer 101, Poloxamer 105, Poloxamer 108, Poloxamer 123, Poloxamer 124, Poloxamer 181, Poloxamer 182, Poloxamer 184, Poloxamer 185, Poloxamer 188, Poloxamer 217, Poloxamer 231, Poloxamer 234, Poloxamer 235, Poloxamer 237, Poloxamer 238, Poloxamer 282, Poloxamer 284, Poloxamer 288, Poloxamer 331, Poloxamer 333, Poloxamer 334, Poloxamer 335, Poloxamer 338, Poloxamer 401, Poloxamer 402, Poloxamer 403, Poloxamer 407.

Poloxamers are sold under the trademark Pluronic® or Lutrol®.

In specific embodiments a suitable poloxamer for use in a composition of the invention has a HLB value of at least about 18 such as, e.g., at least about 20. The mean molecular weight of a suitable poloxamer is typically at least about 2,000. The concentration of the poloxamer in the composition may typically be from about 0% to about 95% w/w such as, e.g., from about 10% to about 90% w/w, from about 10% to about 80% w/w, from about 10% to about 70% w/w, from about 10% to about 60%, from about 10% to about 50%, from about 15% to about 50% w/w, from about 15% to about 45% w/w, from about 15% to about 40% w/w, from about 20% to about 40% w/w, from about 20% to about 35% w/w or from about 20% to about 30% w/w.

Typical block copolymers of ethylene oxide and propylene oxide have a molecular weight of from about 2,000 daltons, typically about 3,000 to about 30,000 daltons such as, e.g. from about 4,000 to about 15,000 daltons.

Polyethylene glycols (which when the molecular weight is above about 20,000 is denoted polyethylene oxides) are mixtures of condensation polymers of ethylene glycol.

Mixtures of PEO with different average molecular weights can be used in order to obtain a PEO with a desirable average molecular weight. It is important to note that in such cases it is necessary to use the PEO, which have MW closest to the desired molecular weight. The individual amount of the two PEO necessary to obtain a PEO with a desired MW can be calculated from the hydroxyl number and the equation given above.

The polymer may have a melting point, which is above the body temperature of the human or animal in which the composition is to be used. Thus, the polymer(s) employed in the matrix composition will suitably have a melting point of about 20-120° C. such as, e.g. from about 30 to about 100° C. or from about 40 to about 80° C.

Alternatively to a polymer of a polyglycol type as described above other polymers may be suitable for use in the matrix composition a). Thus, in other embodiments of the invention, the polymer is selected from one or more of the following polymers: water soluble natural polymers such as glucomannan, galactan, glucan, polygalacturonic acid, polyxylane, polygalactomannans, rhanogalacturonan, polyxyloglycan, arabinogalactan, and starch; water soluble polymers such as PVA, PVB, PVP, methocel, Eudragit L methyl ester and PHPV; biodegradable polymers such as PHA, and PLA; hydrogels, such as olyacrylic amid, and dextran; copolymers such as polylactic acid with polyglycolic acid; and others such as alginate and pectins including low methylated or methoxylated pectins.

The concentration of the polymers in the composition is typically from about 5 to about 99.9% w/w such as from about 10 to about 95% w/w, from about 15% to about 90% w/w, such as from 20 to 85%, such as from 30% to 85% from about 30 to about 99% w/w such as, e.g., from about 35 to about 95% w/w, from about 35 to about 90% w/w, from about 35 to about 85% w/w, from about 35 to about 80% w/w, from about 40 to about 75% w/w, from about 45 to about 70% w/w, from about 45 to about 65% w/w. from about 55 to about 85% w/w or from about 60 to about 85% w/w.

The one or more polymer are typically present in a composition of the invention in a concentration amount of from 5 to 99.9% such as from 10 to 95% such as from 15% to 90%, such as from 20 to 85%, such as from 30% to 85% calculated as w/w % of the matrix composition Opioids A composition according to the invention contains one or more opioids in the matrix. In the present context, the term "opioid" includes substances that specifically interact with opioid receptors as well as substances that have opioid-like effects. Examples of opioids relevant in the present context are given herein before. As it appears from the examples herein, a specific opioid of interest is morphine.

A pharmaceutical composition of the invention is designed to release the active substance in a controlled manner such as by a zero order release mechanism. Accordingly, the composition is also suitable for a controlled release of an active substance. In the present context the term "controlled release" is used to designate a release a desired rate during a predetermined release period. Terms like "modified", "delayed", "sustained", "prolonged", "extended" etc. release are in the present context synonyms to the term "controlled release".

In an embodiment of the invention, the active substance is a pharmaceutically active powder. The powder typically has a particle size of from about 0.1 µm to about 500 µm, typically from about 0.5 µm to about 300 µm, more typically from about 1 µm to about 200 µm, especially from about 5 µm to about 100 µm.

A pharmaceutical composition according to the invention is—due to the possibility of designing the composition in such a manner that i) a zero order release is obtained and ii) a controlled release during a predetermined time period is obtained—suitable for use for water soluble as well as slightly soluble or insoluble opioids. To the class of opioids belong water-soluble as well as less water-soluble substances. A composition according to the invention can also be applied when the at least one opioid has a solubility of at the most about 3 mg/ml such as, e.g. at the most about 1 mg/ml, at the most about 0.1 mg/ml, at the most about 0.05 mg/ml such as, e.g. at the most about 0.001 mg/ml in water at ambient temperature and/or a prolonged release of the active substance is desired in order to obtain i) a prolonged residence time within the body after administration, ii) a reduced peak plasma concentration in order to avoid peak related side effects, iii) reduced frequency of administration in order e.g. to obtain a better patient compliance, etc.

To this end it seems that substantially hydrophobic active substances tend to result in a decrease in the erosion rate of the matrix composition. Substantially hydrophilic or water-soluble active substances seem to have the opposite effect, i.e. they tend to result in a faster erosion of the matrix.

The at least one opioid will suitably be present in an amount of up to about 80%, typically up to about 70%, up to about 60% or up to about 50%, such as, e.g., from 0.1% to 80%, such as from 0.25% to 75%, such as from 0.5% to 60%, such as from 0.75% to 50%, such as from 1% to 40%, such as from 1.5% to 35%, such as from 1.75% to 30%, from 2% to 25%, from 5% to 20%, from 10% to 20% by weight of the matrix composition. An active substance content of about 60-80% is contemplated to be the maximum content, which still allows for a sufficient content of the polymer and, when relevant, the pharmaceutically acceptable excipient in the composition. The active substance may, on the other hand, be present in the composition in much smaller amounts, depending on the nature and potency of the active substance in question.

Preferred dosage forms are compositions comprising 15 mg, 20 mg, 30 mg, 40 mg, 60 mg, 80 mg, 90 mg 100 mg, 120 mg, 130 mg 150 mg, 160 mg, 180 mg 200 mg 250 mg or 300 mg of morphine sulphate or an equivalently effective opioid. Converting dosages between opioids are available in the literature.

Further Therapeutically and/or Prophylactically Active Substances

The method for controlling the release of an active system as disclosed herein can also be applied to other active substances than opioids. Thus besides an opioid, a pharmaceutical composition according to the invention may comprise one or more active substances, i.e. substances, which are therapeutically, prophylactically, diagnostically and/or biologically active substance. The term "active substance" as used herein broadly includes any compound, or mixture thereof, that can be delivered from the composition to produce a beneficial result. The active and beneficial agents include pesticides, herbicides, germicides, biocides, algicides, rodenticides, fungicides, insecticides, antioxidants, plant hormone promoters, plant growth inhibitors, preservatives, disinfectants, sterilization agents, catalysts, chemical reactants, fermentation agents, food supplements, nutrients, cosmetics, therapeutically active substances (drugs), vitamins, sex sterilants, fertility inhibitors, fertility promoters, air purifiers, microorganism attenuators, ecological agents and other agents that benefit the environment in which they are used.

In the present context the term "drug substance" includes any physiologically or pharmacologically active substance that produces a localized or systemic effect in animals, in particular in mammals, including humans and primates. Other animals include domestic household, sport or farm animals such as sheep, goats, cattle, horses and pigs, laboratory animals such as mice, rats and guinea pigs, fishes, avians, reptiles and zoo animals. The term "therapeutically, prophylactically and/or diagnostically active substance" includes the term drug substance within its meaning.

Examples of such substances are hypnotics, sedatives, tranquilizers, anti-convulsants, muscle relaxants, analgesics, anti-inflammatory, anaesthetics, anti-spasmodics, anti-ulcer agents, anti-parasitics, anti-microbiais, anti-fungal, cardiovascular agents, diuretics, cytostatics, anti-neoplastic agents, anti-viral agents, anti-glaucoma agents, anti-depressants, sympathomimetics, hypoglycaemics, diagnostic agents, anti-cough, physic energizers, anti-parkinson agents, local anesthetics, muscle contractants, anti-malarials, hormonal agents, contraceptives, anorexic, anti-arthritic, anti-diabetic, anti-hypertensive, anti-pyretic, anti-cholingergic, bronchodilator, central nervous system, inotropic, vasodilator, vasoconstrictor, decongestant, hematine, iron salts and complexes, electrolyte supplement, germicidal, parasympatholytic, parasympathethomimetic, antiemetic, psychostimulant, vitamin, beta-blockers, H-2 blocker, beta-2 agonist, counterirritants, coagulating modifying agents, stimulants, anti-hormones, drug-antagonists, lipid-regulating agents, uricosurics, cardiac glycosides, ergots and derivatives thereof, expectorants, muscle-relaxants, anti-histamines, purgatives, contrastmaterials, radiopharmaceuticals, imaging agents, anti-allergic agents.

The active substance can be in various forms, such as uncharged or charged molecules, molecular complexes, crystalline forms, amorphous form, polymorphous form, solvates, anhydrates, pharmacologically acceptable salts such as a hydrochloride, hydrobromide, sulfate, laurylate, palmitate, phosphate, nitrite, nitrate, borate, acetate, maleate, tartrate, oleate, and salicylate. For acidic active substance, salts of metals, amines amino acids or organic cations, quaternary ammoniums, can be used. Derivatives of active substances such as esters, ethers and amides which have solubility characteristics suitable for use herein can be used alone or mixed with other drugs. After release of the derivative from the drug delivery system it may be converted by enzymes, hydrolysed by body pH or other metabolic processes to the parent drug or to another biologically active form.

Pharmaceutically Acceptable Excipients
Diffusion and Dissolution Adjusters

As already discussed above, it is important that a composition according to the invention releases at least most of the active substance by a zero order release mechanism. One aspect of research about controlled-release delivery systems involves designing a system, which produces steady-state plasma drug levels. The release of active substance from such systems is also referred to as zero-order drug release kinetics. To meet this objective, numerous design variations have been attempted, and their major controlling mechanisms include diffusion/dissolution.

The release rate of a dissolved or dispersed active substance from a polymeric matrix composition introduced in a specific environment, strongly depends on the nature of the diffusion and sorption processes involving the polymer/environment system and the polymer/active substance system.

The active substance release data may be analyzed using Eq. 1 and Eq. 2 where $M_t/M_\infty$ is the fractional drug release, t is the release time, k is a kinetic constant characteristics of the drug/polymer system, $C_d$ is the tracer loading concentration and n is an exponent which characterizes the mechanism of release of the tracers.

$$\frac{M_t}{M_\infty} = k \cdot t^n \quad \text{(Eq. 1)}$$

$$\frac{dM_t}{A \cdot dt} = n \cdot C_d \cdot k \cdot t^{n-1} \quad \text{(Eq. 2)}$$

Clearly, a desirable mechanism for many applications is that which leads to n=1. This characterizes zero-order behaviour. The table below summarizes the general dependence of n on the diffusion mechanism.

| Diffusinal release solute release Exponent (n) | Overall Solute diffusion mechanism | time dependence of rate ($dM_t/d_t$) |
|---|---|---|
| 0.5 | Fickian diffusion | $t^{-0.5}$ |
| 0.5 < n < 1.0 | Anomalous (non Fickian) diffusion | $t^{n-1}$ |
| 1.0 independent) release | Case II Transport | Zero-order (time |
| n > 1.0 | Super Case II transport | $t^{n-1}$ |

In the case of PEO matrices, the solubility of the polymer can alter the characteristics of the penetrated layer, leading to different behaviours in systems presenting different dissolution features. To control the release of the active agent, there should be a balance between diffusion of the active agent and solubilization of the polymer matrix. The diffusivity of the drug through the matrix, the swelling of the polymer, and its solubilization rate may be biased by changing the molecular weight of the polymer or blending polymer fractions with different molecular weights.

In the following is given examples on suitable excipients that may be added in order to adjust the balance between diffusion and dissolution so as to obtain zero order release rate. The pharmaceutically acceptable excipients suitable for establishing the above-mentioned desired balance, are in the present context also denoted DDAs (Diffusion and Dissolution Adjusters).

Thus, the matrix composition may also comprise one or more pharmaceutically acceptable excipients (DDAs). The function of the at least one pharmaceutically acceptable excipient is to establish the desired balance between on the one hand the diffusion rate of water into the matrix composition and on the other hand the dissolution rate of the matrix composition in an aqueous medium such as, e.g., water. As explained above, a zero order release rate is obtained if that the diffusion rate of the aqueous medium into the matrix composition corresponds to about 100%±30% such as, e.g. about 100%±25%, about 100%±20%, about 100%±15% or about 100%±10% or about 100% of the dissolution rate of the matrix composition. By the term "zero order release" is meant that the release takes place so as to obtain a zero order release of at least about 60% w/w such as, e.g. at least about 65% w/w, at least about 70% w/w, at least about 75% w/w, at least about 80% w/w, at least about 85% w/w, at least about 90% w/w, at least about 95% w/w or at least about 97 or 98% w/w of the active substance from the pharmaceutical composition when subject to an in vitro dissolution test as described herein.

In general a test for diffusion of water into the matrix composition and a test for the dissolution of the matrix composition in an aqueous medium are performed using a matrix composition having the desired shape and being prepared analogous to the matrix composition in the final composition. This means that when the final composition is prepared by e.g. injection moulding then the matrix composition to be tested with respect to diffusion and dissolution behaviour is also prepared by injection moulding.

There may be cases where it is not necessary to adjust the matrix composition by adding a pharmaceutically acceptable excipient. Such cases are e.g. when the polymer employed in itself has the desired properties with respect to diffusion of water and dissolution of polymer.

In the experimental section herein examples are given showing that it has been possible to obtain the desired zero order release when a pharmaceutically acceptable excipients has been incorporated into the matrix composition.

Without being bound by any theory it is contemplated that in those cases where a slightly or insoluble opioid is employed then it may be necessary to circumvent the effect from the active substance (with respect to diffusion and/or dissolution of the matrix composition) by adding a very soluble pharmaceutically acceptable excipient. Accordingly, it is contemplated that when the at least one opioid has a solubility of at the most about 3 mg/ml such as, e.g. at the most about 1 mg/ml, at the most about 0.1 mg/ml, at the most about 0.05 mg/ml such as, e.g. at the most about 0.001 mg/ml in water at ambient temperature then the pharmaceutically acceptable excipient, if present, typically has a solubility of at least 1 mg/ml such as, e.g. at least about 3 mg/ml, at least about 5 mg/ml, at least about 10 mg/ml, at least about 25 mg/ml or at least about 50 mg/ml in water at ambient temperature.

Vice versa, it is contemplated that in those cases where a very soluble opioid is employed then it may be necessary to circumvent the effect from the active substance (with respect to diffusion and/or dissolution of the matrix composition) by adding a slightly or insoluble pharmaceutically acceptable excipient. Accordingly, it is contemplated that when the at least one therapeutically, prophylactically and/or diagnostically active substance has a solubility of at least about 3 mg/ml such as, e.g., at least about 5 mg/ml, at least about 10 mg/ml, at least about 20 mg/ml, at least about 50 mg/ml or at least about 100 mg/ml in water at ambient temperature, then the pharmaceutically acceptable excipients typically has a solubility of at the most about 3 mg/ml such as, e.g., at the most about 1 mg/ml, at the most about 0.1 mg/ml, at the most about 0.05 mg/ml such as, e.g. at the most about 0.001 mg/ml in water at ambient temperature.

There may situations, however, where it also may be suitable to incorporate water-soluble substances (and/or water-insoluble substances) as DDA's irrespective of the solubility of the active substance.

Furthermore, in those cases where the active substance employed has a low solubility in acidic medium, it is contemplated that an inorganic or organic base or substance having an alkaline reaction in aqueous environment is employed as a DDA.

Analogous, in those cases where the active substance employed has a low solubility in alkaline medium, it is contemplated that an inorganic or organic acid or substance having an acidic reaction in aqueous environment is employed as a DDA.

However, other factors than the solubility in water play a role in the erosion process and therefore there may be situations where such factors dominate the solubility factor and then the above-given combinations may be of minor importance.

Suitable pharmaceutically acceptable excipients (DDAs) may be selected from the group consisting of inorganic acids, inorganic bases, inorganic salts, organic acids or bases and pharmaceutically acceptable salts thereof, saccharides, oligosaccharides, polysaccharides, and cellulose and cellulose derivatives.

Alternatively or additionally, a suitable pharmaceutically acceptable excipient is a mono-, di-, oligo, polycarboxylic acid or amino acids such as, e.g. acetic acid, succinic acid, citric acid, tartaric acid, acrylic acid, benzoic acid, malic acid, maleic acid, sorbic acid etc., aspartic acid, glutamic acid etc.

Examples of suitable organic acids include acetic acid/ethanoic acid, adipic acid, angelic acid, ascorbic acid/vitamin C, carbamic acid, cinnamic acid, citramalic acid, formic acid, fumaric acid, gallic acid, gentisic acid, glutaconic acid, glutaric acid, glyceric acid, glycolic acid, glyoxylic acid, lactic acid, levulinic acid, malonic acid, mandelic acid, oxalic acid, oxamic acid, pimelic acid, and pyruvic acid.

Examples of suitable inorganic acids include pyrophosphoric, glycerophosphoric, phosphoric such as ortho and meta phosphoric, boric acid, hydrochloric acid, and sulfuric acid.

Examples of suitable inorganic compounds include aluminium.

Examples of organic bases are p-nitrophenol, succinimide, benzenesulfonamide, 2-hydroxy-2cyclohexenone, imidazole, pyrrole, diethanolamine, ethyleneamine, tris (hydroxymethyl)aminomethane, hydroxylamine and derivates of amines, sodium citrate, aniline, hydrazine.

Examples of inorganic bases include aluminium oxide such as, e.g., aluminium oxide trihydrate, alumina, sodium hydroxide, potassium hydroxide, calcium carbonate, ammonium carbonate, ammonium hydroxide, KOH and the like.

Suitable pharmaceutically acceptable salts of an organic acid is e.g. an alkali metal salt or an alkaline earth metal salt such as, e.g. sodium phosphate, sodium dihydrogenphosphate, disodium hydrogenphosphate etc., potassium phosphate, potassium dihydrogenphosphate, potassium hydrogenphosphate etc., calcium phosphate, dicalcium phosphate etc., sodium sulfate, potassium sulfate, calcium sulfate, sodium carbonate, sodium hydrogencarbonate, potassium carbonate, potassium hydrogencarbonate, calcium carbonate, magnesium carbonate etc., sodium acetate, potassium acetate, calcium acetate, sodium succinate, potassium succinate, calcium succinate, sodium citrate, potassium citrate, calcium citrate, sodium tartrate, potassium tartrate, calcium tartrate etc.

A suitable inorganic salt for use in a matrix composition of the invention is sodium chloride, potassium chloride, calcium chloride, magnesium chloride etc.

Examples of such excipients are glucose and other monosaccharides, ribose, arabinose, xylose, lyxose, allose, altrose, inosito, glucose, sorbitol, mannose, gulose, idose, galactose, talose, mannitol, fructose, lactose, sucrose, and other disaccharides, dextrin, dextran or other polysaccharides, amylose, xylan, cellulose and cellulose derivatives such as, e.g. microcrystalline cellulose, methyl cellulose, ethyl cellulose, ethylhydroxyethyl cellulose, ethylmethylcellulose, hydroxyethylcellulose, hydroxyethylmethyl cellulose, carboxymethyl cellulose, hydroxypropyl cellulose, hydroxymethylpropyl cellulose, hydroxypropylmethyl cellulose, amylopectin, pectin, starch, sodium starch etc., kaolin, bentonit, acacia, alginic add, sodium alginate, calcium alginate, gelatin, dextrose, molasses, extract of Irish moss, panwar gum, ghatti gum, mucilage of isapol husk, veegum, glycollate, magnesium stearate, calcium stearate, stearic acid, talc, titanium dioxide, silicium dioxide, clays, croscarmellose, gums, agar etc.

Other Ingredients in the Matrix Composition

The matrix composition may also contain other excipients as well, e.g. in order to improve the technical properties of the matrix composition so that it may be easier to produce or in order to improve the stability of the composition.

A suitable pharmaceutically acceptable excipient for use in a matrix composition of the invention may be selected from the group consisting of fillers, diluents, disintegrants, glidants, pH-adjusting agents, viscosity adjusting agents, solubility increasing or decreasing agents, osmotically active agents and solvents.

Suitable excipients include conventional tablet or capsule excipients. These excipients may be, for example, diluents such as dicalcium phosphate, calcium sulfate, lactose or sucrose or other disaccharides, cellulose, cellulose derivatives, kaolin, mannitol, dry starch, glucose or other monosaccharides, dextrin or other polysaccharides, sorbitol, inositol or mixtures thereof; binders such as acacia, sodium alginate, starch, gelatin, saccharides (including glucose, sucrose, dextrose and lactose), molasses, extract of Irish moss, panwar gum, ghatti gum, mucilage of isapol husk, carboxymethylcellulose, methylcellulose, veegum, larch arabolactan, polyethylene glycols, ethylcellulose, water, alcohols, waxes, polyvinylpyrrolidone such as, e.g., PVP K90 (may be used to improve mixing of the polymer with the other ingredients) or mixtures thereof; lubricants such as talc, magnesium stearate, calcium stearate, staeric acid, hydrogenated vegetable oils, sodium benzoate, sodium chloride, leucine, carbowax 4000, magnesium lauryl sulfate, colloidal silicon dioxide and mixtures thereof, disintegrants such as starches, clays, cellulose derivatives including crosscarmellose, gums, aligns, various combinations of hydrogencarbonates with weak acids (e.g. sodium hydrogencarbonate/tartaric acid or citric acid) crosprovidone, sodium starch glycolate, agar, cation exchange resins, citrus pulp, veegum HV, natural sponge, bentonite or mixtures thereof; volatile solvents such as alcohols, including aqueous alcohols, petroleum benzine, acetone, ether or mixtures thereof; plasticizers such as sorbitol and glycerine; and others such as cocoa butter, polyethylene glycols or polyethylene oxides, e.g. with a molecular weight of about 1,000-500,000 daltons, typically about 1,000-100,000 daltons, more typically 1,000-50,000 daltons, especially about 1,000-10,000 daltons, in particular about 1,500-5,000 daltons, and mixtures thereof, hydrogenated vegetable oils, glycerinated gelatin or mixtures thereof.

The matrix composition may in addition include a cellulose derivative, e.g. a cellulose derivative selected from the group consisting of methylcellulose, carboxymethylcellulose and salts thereof, microcrystalline cellulose, ethylhydroxyethylcellulose, ethylmethylcellulose, hydroxyethylcellulose, hydroxyethylmethylcellulose, hydroxypropylcellulose, hydroxypropylmethylcellulose, hydroxymethylcellulose and hydroxymethylpropylcellulose. Of these cellulose derivatives, hydroxypropylmethylcellulose and methylcellulose are preferred for incorporation in the matrix composition.

Furthermore, the matrix composition may comprise one or more agents selected from the group consisting of sweetening agents, flavouring agents and colouring agents, in order to provide an elegant and palatable preparation. Examples of colouring agents are water soluble FD&C dyes and mixtures thereof with corresponding lakes and direct compression sugars such as Di-Pac from Amstar. In addition, coloured dye migration inhibitors such as tragacanth, acacia or attapulgite talc may be added. Specific examples include Calcium carbonate, Chromium-cobalt-aluminium oxide, ferric ferrocyanide, Ferric oxide, Iron ammonium citrate, Iron (III) oxide hydrated, Iron oxides, Magnesium carbonate, Titanium dioxide.

Examples of suitable fillers are also dextrin, sucralfate, calcium hydroxyl-apatite, calcium phosphates and fatty acid salts such as magnesium stearate.

The filler may be added in an amount so that the combination of the filler and the active substance comprises up to about 60%, typically up to about 50%, by weight of the first composition.

In order to soften the carrier system, a plasticziser may be incorporated in the composition. A suitable plasticizer is selected from the group consisting of phosphate esters; phthalate esters; amides; mineral oils; fatty acids and esters; fatty alcohols, vegetable oils and hydrogenated vegetable oils including acetylated hydrogenated cottonseed glyceride and acetylated hydrogenated soybean oil glycerides; acetyl tributyl citrate, acetyl triethyl citrate, Castor oil, diacetylated monoglycerides, dipropylene glycol salicylate glycerin, glyceryl cocoate, mono- and di-acetylated monoglycerides, nitrobenzene, carbon disulfide, fl-naphtyl salicylate, phthalyl glycolate, diocyl phthalate; sorbitol, sorbitol glyceryl tricitrate; sucrose octaacetate; a-tocopheryl polyethylene glycol succinate, phosphate esters; phthalate esters; amides; mineral oils; fatty acids and esters; fatty alcohols; and vegetable oils, fatty alcohols including cetostearyl alcohol, cetyl alcohol, stearyl alcohol, oleyl alcohol and myristyl alcohol; methyl abietate, acetyl tributyl citrate, acetyl triethyl citrate, diisooctyl adipate, amyl oleate, butyl ricinoleate, benzyl benzoate, butyl and glycol esters of fatty acids, butyl diglycol carbonate, butyl oleate, butyl stearate, di(beta-methoxyethyl) adipate, dibutyl sebacate, dibutyl tartrate, diisobutyl adipate, dihexyl adipate, triethylene glycol di(beta-ethyl butyrate), polyethylene glycol di(2-ethyl hexoate), diethylene glycol monolaurate, monomeric polyethylene ester, hydrogenated methyl ester of rosin, methoxyethyl oleate, butoxyethyl stearate, butyl phthalyl butyl glycolate, glycerol tributyrate, triethylene glycol dipelargonate, beta-(p-tert-amyl phenoxy)ethanol, beta(p-tert-butytphenoxy)ethanol, beta-(p-tertbutytphenoxyethyl)acetate, bis(beta-p-tert-buthylphenoxydiethyl)ether, camphor, Cumar W-1, Cumar MH-1, Cumar V-1, diamyl phthalate, (diamylphenoxy) ethanol, diphenyl oxide, technical hydroabietyl alcohol, beckolin, benzene hexahydrochlonde, Clorafin 40, Piccolastic A-5, Piccalastic A-25, Flexol B-400, Glycerol alfa-methyl alfaphenyl ether, chlorinated naphthalene, HB-40, monoamylphthalate. Nevillac 10 o-nitrodiphenyl and Paracril 26.

Preferred anti-oxidative agents include TPG e.g. in the form of TPGS due to surfactant properties, BHA, BHT, t-butyl hydroquinone, calcium ascorbate, gallic acid, hydroquinone, maltol, octyl gallate, sodium bisulfate, sodium metabisulfite, tocopherol and derivates thereof, citric acid, tartaric acid, and ascorbic acid. Other antioxidants include trivalent phosphorous like e.g phosphite, phenolic antioxidants, hydroxylamines, lactones such as substituted benzofuranones. Hindered phenols, thiosynergists and/or hindered amines are useful for the long-term stability for polymers, whereas the following antioxidants are suitable for use also in situation where the active substance is subject to oxidation: acids (ascorbic acid, erythorbic acid, etidronic acid, gallic acid, hypophosphorous acid, nordihydroguairetic acid, propionic acid etc.), phenols (e.g. BHA, BHT, t-butyl hydroquinone, dodecyl gallate, octyl gallate, 1,3,5-trihydroxybenzene), organic and inorganic salts (calcium ascorbate, sodium ascorbate, sodium bisulphite, sodium metabisulfite, sodium sulfite, potassium bisulphite, potassium metabisulphite), esteres (calcium ascorbate, dilauryl thiodipropionate, dimyristyl thiodipropionate, distearyl thiodipropionate), pyranon (maltol), and vitamin E (tocopherol, D-α-tocopherol, DL-α-tocopherol, tocopheryl acetate, d-α-tocopheryl acetate, dl-α-tocopheryl acetate. However, other anti-oxidative agents known in the art may be used according to the present invention.

pH Dependant Release

In some situations it may be convenient that the composition releases the active substance in a pH dependant manner. As described in e.g. WO 99/51208 a pH dependant release can be obtained by inclusion of a so-called release rate modifier. The release rate modifier is preferably selected from materials conventionally used in the pharmaceutical industry to produce enteric coatings. A number of different types of compounds suitable for use as enteric coatings are known in the art; see e.g. *Remington's Pharmaceutical Sciences,* 18th Edition, 1990. Release modifiers may in particular be selected from one of three general classes, namely cellulose derivatives, methacrylic acid polymers and modified gelatine compounds. Preferred release modifiers include cellulose acetate phthalate, polyvinyl acetate phthalate, hydroxypropyl methylcellulose phthalate and hydroxypropyl methylcellulose acetate succinate, as well as methacrylic acid copolymers. Modified gelatine compounds include gelatine treated with e.g. formaldehyde or glutaraldehyde.

Examples of commercially available polymers suitable as release modifiers are EUDRAGIT® L and EUDRAGIT® S, available from Röhm GmbH, Germany, and enteric coating agents available from Shin-Etsu Chemical Co., Japan. The release modifier will typically be present in the composition in an amount of about 0.1-10%, based on the weight of the matrix, preferably about 0.5-4%, e.g. about 1-3%, such as about 1.5-2.0%. If desired, a suitable mixture of more than one release modifier may be used in order to obtain a desired release profile in any given composition.

The release modifier enables a difference in release of the active substance/erosion of the matrix dependant on pH.

Coating

The pharmaceutical composition may thus have the shape of a cylindrical rod e.g. having one or two conical shaped ends, which is provided with a coating, which is substantially insoluble in and impermeable to fluids such as body fluids during the intended release period, the coating having an opening at one or both ends. Polymers useful as coatings are preferably those, which are possible to process by extrusion, solution or in the form of a dispersion. Most preferred are those, which are available in a food grade or a pharmaceutical grade quality. Examples of such polymers are cellulose acetate, polyamide, polyethylene, polyethylene terephthalate, polypropylenem polyurethane, polyvinyl acetate, polyvinyl chloride, silicone rubber, latex, polyhydroxybutyrate, polyhydroxyvalerate, teflon, polylactic acid or polyglycolic acid and copolymers thereof, copolymers such as ethylene vinyl acetate (EVA), styrene-butadienestyrene (SBS) and styrene-isoprene-styrene (SIS).

The coating may also be a coating, which is substantially soluble in and permeable to fluids such as body fluids during the intended release period provided that the coating dissolves so much slower than the matrix composition that the coating remains intact until the matrix has eroded and released the active substance. Examples of suitable polymers include polyols as described herein.

The coating may further comprise any of the above-mentioned matrix materials in a form, which erodes at a substantially slower rate than the rest of the matrix. The coating may thus comprise a matrix of one or more substantially water soluble crystalline polymers and, optionally, a non-ionic emulsifier, the coating being one which is eroded in the aqueous phase at a substantially slower rate than the matrix composition comprising the active substance, whereby a substantially constant area of the matrix composition comprising the active substance is exposed during erosion of the matrix composition, and whereby the coating is substantially eroded upon erosion of the matrix composition comprising the active substance. Such a coating will be designed so that its longitudinal erosion rate is substantially the same as the longitudinal erosion rate of the matrix, whereby the matrix and the coating will erode longitudinally towards the centre of the composition at substantially the same rate. Thus, when the matrix composition has been completely eroded by the aqueous medium, the coating will also be substantially completely eroded. A matrix composition having such a coating has the obvious advantage of being completely biodegraded upon release of the active substance. Such a coating will typically be a combination of a polyethylene glycol and a mixture of, for example, polyethylene glycol 400 monostearate or another non-ionic emulsifier, and may also include a filler. The content of the mixture of non-ionic emulsifiers and the filler in the coating will be determined in each particular case according to the characteristics, e.g. erosion rate and size, of the matrix comprising the active substance.

In an embodiment of the invention, the coating is one, which disintegrates or crumbles after erosion of the matrix. A coating of this type will remain intact as long as it is supported by the matrix containing the active substance, but it lacks the ability to remain intact after erosion of the matrix, because it then disintegrates or crumbles, so that it will not remain in e.g. a human or animal for any significant amount of time after the complete erosion of the matrix and the release of the active substance.

The coating may also be an enteric coating employing methacrylates, a co-polymer of methacrylate-galactomannan etc.

In an interesting embodiment, the controlled release composition of the invention further comprises a coating having at least one opening exposing at least one surface of the matrix, the coating being one which crumbles and/or erodes upon exposure to the aqueous medium at a rate which is equal to or slower than the rate at which the matrix erodes in the aqueous medium, allowing exposure of said surface of the matrix to the aqueous medium to be controlled. Coatings of this type are described in WO 95/22962, to which reference is made and which is incorporated herein by reference. These coatings comprise:

(a) a first cellulose derivative which has thermoplastic properties and which is substantially insoluble in the aqueous medium in which the composition is to be used, e.g. an ethylcellulose such as ethylcellulose having an ethoxyl content in the range of 44.5-52.5%, or cellulose acetate, cellulose propionate or cellulose nitrate;

and at least one of:

(b) a second cellulose derivative which is soluble or dispersible in water, e.g. a cellulose derivative selected from the group consisting of methylcellulose, carboxymethylcellulose and salts thereof, cellulose acetate phthalate, microcrystalline cellulose, ethylhydroxyethylcellulose, ethylmethylcellulose, hydroxyethylcellulose, hydroxyethylmethylcellulose, hydroxypropylcellulose, hydroxypropylmethylcellulose, hydroxymethylcellulose and hydroxymethylpropylcellulose;

(c) a plasticizer, e.g. selected from the group consisting of phosphate esters; phthalate esters; amides; mineral oils; fatty acids and esters thereof with polyethylene glycol, glycerin or sugars; fatty alcohols and ethers thereof with polyethylene glycol, glycerin or sugars; and vegetable oils; or a non-ionic surfactant; and (d) a filler, e.g. selected from conventional tablet or capsule excipients such as diluents, binders, lubricants and disintegrants.

The first cellulose derivative (a) such as, e.g., ethylcellulose is typically contained in the coating in a concentration of from about 10 to about 99% w/w such as, e.g., from about 20 to about 95% w/w, from about 30 to about 90% w/w, from about 40 to about 90% w/w, from about 45 to about 90% w/w, from about 50 to about 85% w/w or from about 50 to about 80% w/w.

The use of a plasticizer will often be desirable in order to improve the processability of the ethylcellulose or the first cellulose derivative. The plasticizer may also be a non-ionic surfactant, e.g. a non-ionic surfactant selected from the group consisting of diacetylated monoglycerides, diethylene glycol monostearate, ethylene glycol monostearate, glyceryl monooleate, glyceryl monostearate, propylene glycol monostearate, macrogol esters, macrogol stearate 400, macrogol stearate 2000, polyoxyethylene 50 stearate, macrogol ethers, cetomacrogol 1000, lauromacrogols, nonoxinols, octocinols, tyloxapol, poloxamers, polyvinyl alcohols, polysorbate 20, polysorbate 40, polysorbate 60, polysorbate 65, polysorbate 80, polysorbate 85, sorbitan monolaurate, sorbitan monooleate, sorbitan monopalmitate, sorbitan monostearate, sorbitan sesquioleate, sorbitan trioleate, sorbitan tristearate and sucrose esters; nitrobenzene, carbon disulfide, β-naphtyl salicylate, phthalyl glycolate, dioctyl phthalate.

Other suitable plasticizers appear from EP-B-0 746 310 to which reference is made.

Pharmaceutical Composition

As mentioned above a pharmaceutical composition according to the invention is a coated matrix composition from which the active substance is released by a zero order release mechanism.

A composition according to the invention containing a drug substance is typically for oral administration and may be in the form of a tablet or a capsule or in the form of a multiple unit dosage form. Due to the possibility of controlling the release rate of the active substance the composition may be adapted for oral administration 1-6 times a day, normally 1-4 times daily such as 1-3 times, 1-2 times or 1 times daily. The technology may also provide compositions for administration only once or twice daily. In the present context the term "once daily" is intended to mean that it is only necessary to administer the pharmaceutical composition once a day in order to obtain a suitable therapeutic and/or prophylactic response; however, any administration may comprise co-administration of more than one dosage unit, such as, e.g. 2-4 dosage units if the amount of active substance required may not be formulated in only one composition or if a composition of a smaller size is preferred.

The dosage of the active substance depends on the particular substance, the age, weight condition etc. of the human or animal that will be treated with the composition etc. All such factors are well known to a person skilled in the art.

The controlled release of the active substance is caused by erosion at a substantially constant rate of a surface or surfaces of the composition The rate at which the active substance is released from the matrix is a predetermined rate, i.e. a rate, which is controllable over a certain period of time. The release rate required in each particular instance may inter alia depend on the amount of active substance to be released for it to exert the desired effect, as well as on the overall dosage of the active substance contained in the matrix. The substance of which the matrix is composed and the distribution of the active substance in the matrix may therefore be selected according to one or more of these criteria to ensure the desired level of release of the active substance.

Due to the controlled release of the active substance obtainable from the pharmaceutical composition of the invention, it is possible to obtain a substantially constant rate of release of the active substance over a specific period of time, corresponding to the dosage necessary for the treatment in question, so that adherence to a strict dosage regimen, e.g. requiring administration of a drug at set intervals up to several times a day, may be dispensed with.

Furthermore, it is possible to include two or more different active substances in the pharmaceutical composition of the invention, and the two or more different active substances may be adapted to be released at different concentrations and/or intervals, thus making it easier for patients to follow a prescribed regimen.

An additional advantage of a pharmaceutical composition of the invention, compared to other known controlled release compositions, is that it may be produced by relatively simple and inexpensive methods.

Furthermore, a pharmaceutical composition according to the invention allows for the incorporation of high concentrations of the active substance relative to the size of the delivery system. This is obviously a great advantage, notably when the composition is to be used for the delivery of a therapeutically, prophylactically and/or diagnostically active substance, since it allows for the delivery of the required amount of the active substance without the size of the composition being unnecessarily large. In addition, sparingly soluble or non-soluble active substances may be readily incorporated into a composition of the invention. A composition of the invention may thus be used for the delivery of, for example, sparingly soluble or non-soluble pharmaceutical powders which can otherwise be difficult to administer.

As mentioned above, the release of the opioid from the pharmaceutical composition corresponds to a substantially zero order release determined by in vitro dissolution test according to USP with or without application of sinkers. The substantially zero order release is obtained in a time period of at least 1 hours such as, e.g. at least 2 hours, at least 3 hours, at least 4 hours or at least 5 hours, or in a time period of at least 5 hours such as, e.g. at least 6 hours, at least 7 hours, at least 8 hours, at least 9 hours or at least 10 hours.

Morphine Compositions

In the experimental section herein examples are given on suitable morphine containing compositions, which are based on the concept described herein.

In an embodiment the invention provides
a pharmaceutical composition for controlled release of morphine or a pharmaceutically acceptable salt or metabolite thereof into an aqueous medium by erosion of at least one surface of the composition, the composition comprising
i) a matrix composition comprising a) polymer or a mixture of polymers, b) morphine or a pharmaceutically acceptable salt or metabolite thereof and, optionally, c) one or more pharmaceutically acceptable excipients, and
ii) a coating having at least one opening exposing at the one surface of said matrix, the coating comprising
    a) a first cellulose derivative which has thermoplastic properties and which is substantially insoluble in the aqueous medium in which the composition is to be used,
and at least one of
    b) a second cellulose derivative which is soluble or dispersible in water,
    c) a plasticizer, and
    d) a filler,
wherein the matrix composition has a conus-like shape so that the surface area exposed to the aqueous medium increases at least during initial erosion of the matrix composition, and the dissolution of the opioid—when tested in a Dissolution Test as described herein with with or without application of sinkers—results in a zero order release of at least 80% of the opioid contained in the composition.

Especially suitable polymers are those of the polyol type described herein such as, e.g. polyethylene glycol, a polyethylene oxide and/or a block copolymer of ethylene oxide and propylene oxide. The polymers have a molecular weight of from about 20,000 daltons, such as, e.g., from about 20,000 to about 700,000 daltons, from about 20,000 to about 600,000 daltons, from about 35,000 to about 500,000 daltons, from about 35,000 to about 400,000 daltons, from about 35,000 to about 300,000 daltons, from about 50,000 to about 300,000 daltons, such as, e.g. about 35,000 daltons, about 50,000 daltons, about 75,000 daltons, about 100,000 daltons, about 150,000 daltons, about 200,000 daltons, about 250,000 daltons, about 300,000 daltons or about 400,000 daltons.

From the examples it is seem that employment of PEO 200,000 leads to a suitable composition.

Suitable pharmaceutically acceptable excipients are also described herein such as, e.g. inorganic acids, inorganic bases, inorganic salts, organic acids or bases and pharmaceutically acceptable salts thereof, saccharides, oligosaccharides, polysaccharides, and cellulose and cellulose derivatives. The organic acid may be a mono-, di-, oligo or polycarboxylic acid such as, e.g. acetic acid, succinic acid, citric acid, tartaric acid, acrylic acid, benzoic acid, malic acid, maleic acid etc.

From the examples it is seem that employment of mannitol or a base like aluminium oxide leads to a suitable composition.

Accordingly, in a specific embodiment the invention relates to a pharmaceutical composition in which the matrix composition comprises morphine, PEO 200,000 and mannitol and/or aluminium oxide. Preferred embodiments appear from the examples, however the excipients are generally used in concentrations from 0-60%, such as, e.g., from about 0 to about 50%, from about 0 to about 40%, from about 0.5 to about 30%, such as from 0.2 to 15%, preferable from 0.5% to 10%. The actual amount preferred in the composition for optimizing the desired function of the excipients depends on the properties of the individual excipients.

In a specific embodiment, a composition according to the invention is in the form of a single unit dose as opposed to a multiple unit composition. However, as described below it is also possible to provide a multiple unit composition.

Multiple Units Composition

The pharmaceutical composition according to the invention may furthermore be used in the preparation of a multiple units pharmaceutical composition, e.g. in the form of a capsule or tablet. A multiple units pharmaceutical composition is a composition, which comprises a multiplicity of individual units in such a form that the individual units will be made available upon disintegration of the composition, typically a capsule or tablet, in the stomach of humans or animals ingesting said composition. Thus, in this case, at least some of the individual units in said multiple units pharmaceutical composition will consist of the composition of the invention, the individual units being of a size, which allows them to be incorporated into such a composition.

Preparation

The delivery system as well as the first composition of the invention may be produced by various methods which are either known per se in the pharmaceutical industry or which, for example, are used in the production of polymer-based materials, depending upon the desired embodiment and the materials employed in the composition in question. As mentioned above, one advantage of the composition according to the invention is that it may be produced by methods, which are relatively simple and inexpensive.

A pharmaceutical composition may be produced by, for example, co-extrusion of the coating with the matrix composition and the active substance, extrusion and dip coating, injection moulding and dip coating, or by extrusion or injection moulding and solvent coating by spraying or dipping.

For further details reference is made to the experimental section herein.

Method for Controlling the Release

As mentioned above the interaction of controlling the release of the active ingredient in light of the desired plasma concentration and the given pharmacokinetic properties of the drug is the most important factor for optimizing the clinical use of a drug. It is clear from the clinical results and the interaction with the highly controllable release demonstrated herein that superior formulations may be achieved with the present technology.

The in vivo control may easily be described by the % of maximal concentration at different time points after dosing in a single dose study. By linking the concentration at specific time points relative to the maximal concentration, situations where high late concentrations is predominantly a function of elimination from a high peak concentration are excluded.

As clearly appears from the above results, the formulation according to the present invention demonstrates a plasma curve capable of resulting in a substantial constant steady state curve after multiple dosing. This is demonstrated by the fact that the product according to the present invention demonstrates a maximum concentration which is approximately half 55% of the reference product (Study 3). The time where the concentrations is at least half the maximal concentration ($C \geq 50\%$) is 80% longer by the product according to the invention as demonstrated in Study 2 and in addition, the time where the concentrations is at least 75% of the maximal value is 92% of the time obtained with the reference product. From Study 3 it is seen that the time where the concentration is at least 50% of the maximal concentration is more than 100% longer for the composition according to the present invention.

It is clear from these values that the release from the product according to the present invention is not only very much controlled in vitro as demonstrated by a zero order release, but also demonstrates a high degree of control in vivo.

In addition the concentration by the end of the dosing interval corresponding to hour 12 for a twice daily product is actually 15% higher than for the reference product in the present study. It appears that the formulation will also be suitable for a once daily administration as the plasma concentration at hour 24 is about half of the maximal concentration whereas the reference product at hour 24 demonstrates a concentration less than 15% of its maximal concentration.

Accordingly, the present invention provide a product capable for obtaining a stable plasma concentration as demonstrated by single dose pharmacokinetic parameters where the concentration 8 hours after dosing is at least 40% of the maximal concentration obtained by the dose, such as at least 50% and more preferred at least 60% of the maximal concentration.

In a further aspect, the present invention provides a formulation wherein the concentration 10 hours after dosing is at least 40% of the maximal concentration obtained by the dose, such as at least 50% and more preferred at least 60% of the maximal concentration.

In a still further aspect, the present invention provides a formulation wherein the concentration 12 hours after dosing is at least 20% of the maximal concentration obtained by the dose, such as at least 30% and more preferred at least 35% and more preferred about 40% and still more preferred at least 40% of the maximal concentration.

For a once daily product where a substantial plasma concentration is needed throughout the dosing interval, it is important that the single dose pharmacokinetic parameters demonstrate a high level of control of release from the dosage form as proved with the present invention.

Accordingly a once daily formulation is also disclosed herein. Such formulation of the present invention is one where the plasma concentration is at least 50% of the maximal concentration for at least 6 hours, preferable at least 8 hours, more preferred for at least 9 hours and still more preferred for at least 10 hours. In a further preferred formulation, a concentration of at least 20% such as at least 25% and more preferred at least 30% is present at hour 12 after dosing. For a still more preferred once daily formulation, the concentration is at least 20% such as at least 25% and more preferred least 30% such as at least 35% of the maximal concentration at hour 18 after dosing and still more preferred a concentration of at least 20% such as at least 25% such as about 30% of the maximal concentration is present at hour 24 after dosing of a single dose.

It is contemplated that the high concentrations described herein by the late hours 8 to 24 by a single dose is not a result of a simple delay of release from the formulation, but obtained with a formulation wherein the maximal concentration is reached within hour 1 to 10, such as within hour 1.5 to 9, more preferred within hour 2 to 8 and still more preferred within hour 1.5 to 7, such as within hour 2 to 6 and even more preferred within hour 2.5 to from the dosing time point in order to provide the patient with a sufficient pain relief and at the same time avoiding a high absorption rate resulting in a peak like plasma concentration curve.

As mentioned above, the invention also relates to a method for controlling the release of an opioid from a pharmaceutical composition. To this end all details and particulars described above under the composition aspect applies mutatis mutandi to the method aspect and to other aspects of the invention.

The invention is further illustrated in the following figures and non-limiting examples.

FIG. 1A is a plug holder suitable for use when determining diffusion and dissolution rate. A stopper on the right seals the plug holder, and the swelling layer is formed on the left side on the plug.

FIG. 1B is a suitable conical shape for an opioid composition. Suitable values are e.g. $a=3$ mm, $b=4.5$ mm, $c=1.5$ mm and $d=9$ mm; $a=3$ mm, $b=4.6$ mm, $c=2$ mm and $d=9$ mm; $a=2.3$ mm, $b=5.3$ mm, $c=1.5$ mm and $d=7.5$ mm; or $a=3.4$ mm, $b=5.1$ mm, $c=2$ mm and $d=7.5$ mm

FIG. 3 (1A, 1B, 2A and 2B) shows the dissolution profiles from the compositions of Example 2.

Figure 7:
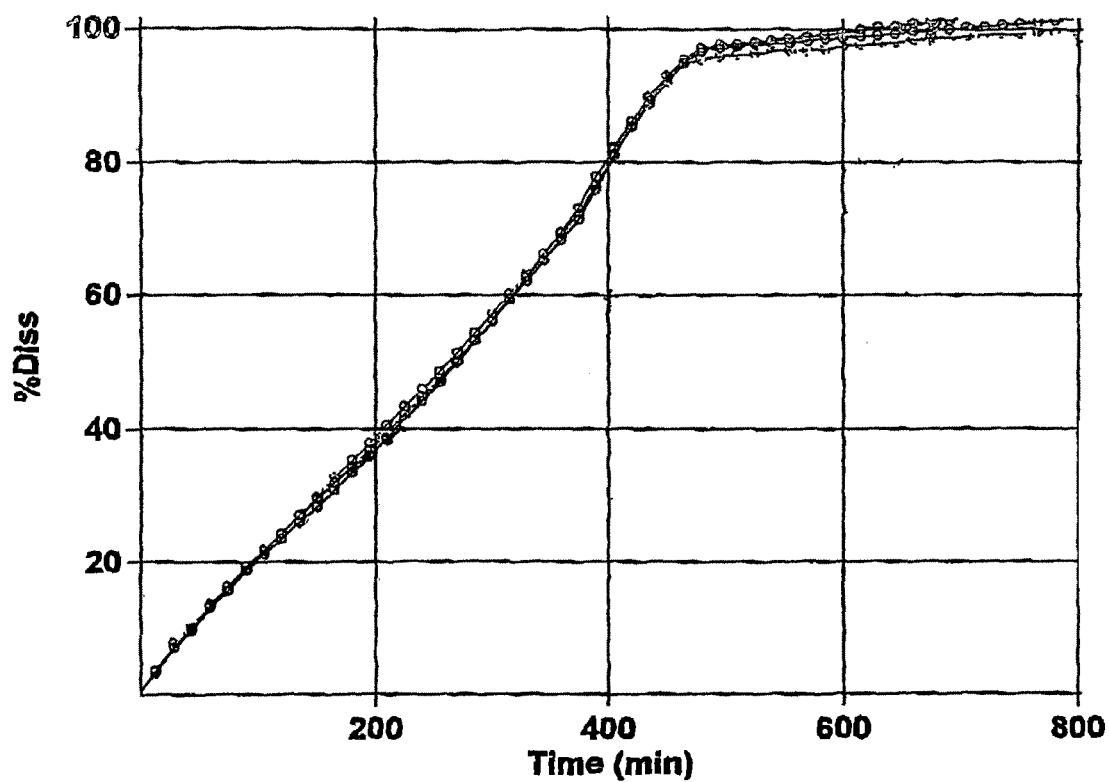

FIG. 7 shows a dissolution curve of batch 03-0005-66 basket method, rpm 100, buffer pH 6.8, the formulation being a cone 1 according to table A. The dissolution time is 473 minutes for the two upper curves.

The dissolution curve demonstrates an increase in release at the time corresponding to the time where the erosion has passed the cone area (2 formulations did not move regularly and were disregarded; the same applies to several of the other dissolution diagrams).

Figure 8:
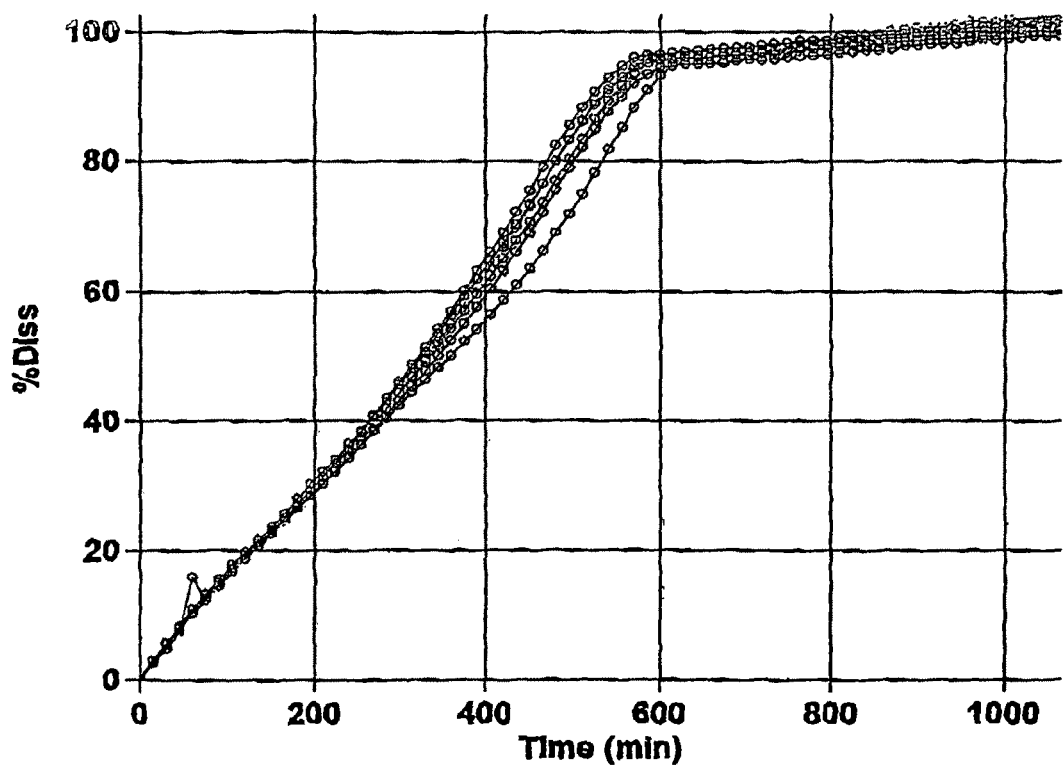

FIG. 8 shows the same formulation as in FIG. 7, however the dissolution is the paddle method, rpm 100, same medium buffer pH 6.8. The dissolution time is 578 minutes.

Figure 9:
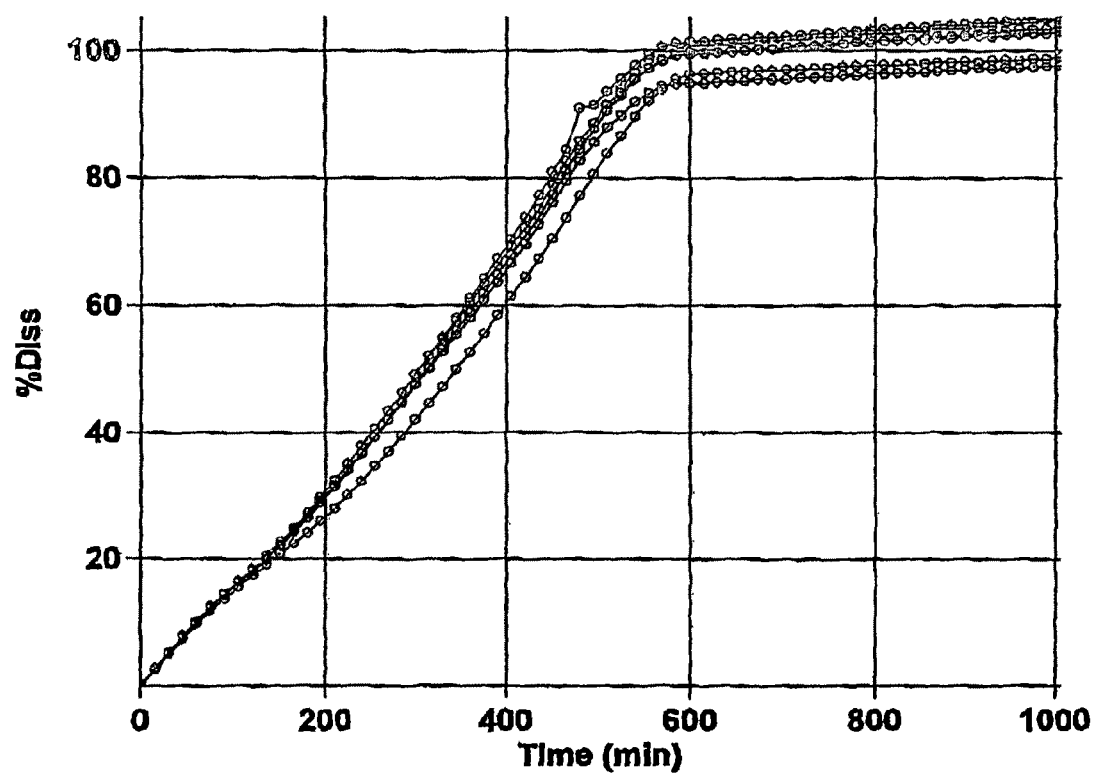

FIG. 9 shows the same as FIG. 8 except that the rotation speed is 50 rpm. The dissolution time is 573 minutes.

Figure 10:
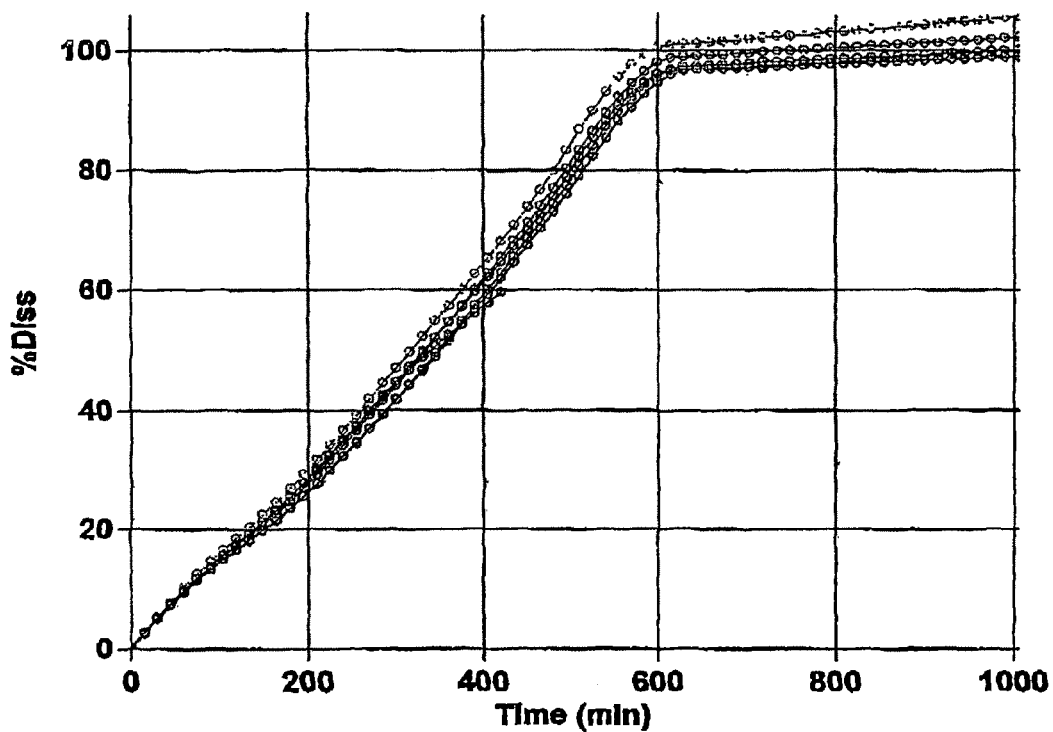

FIG. 10 shows a dissolution curve of batch 03-0003-66 paddle method, rpm 50, medium buffer pH 6.8, the formulation is a cone 2 according to table A. The dissolution time is 594 minutes.

Figure 11:
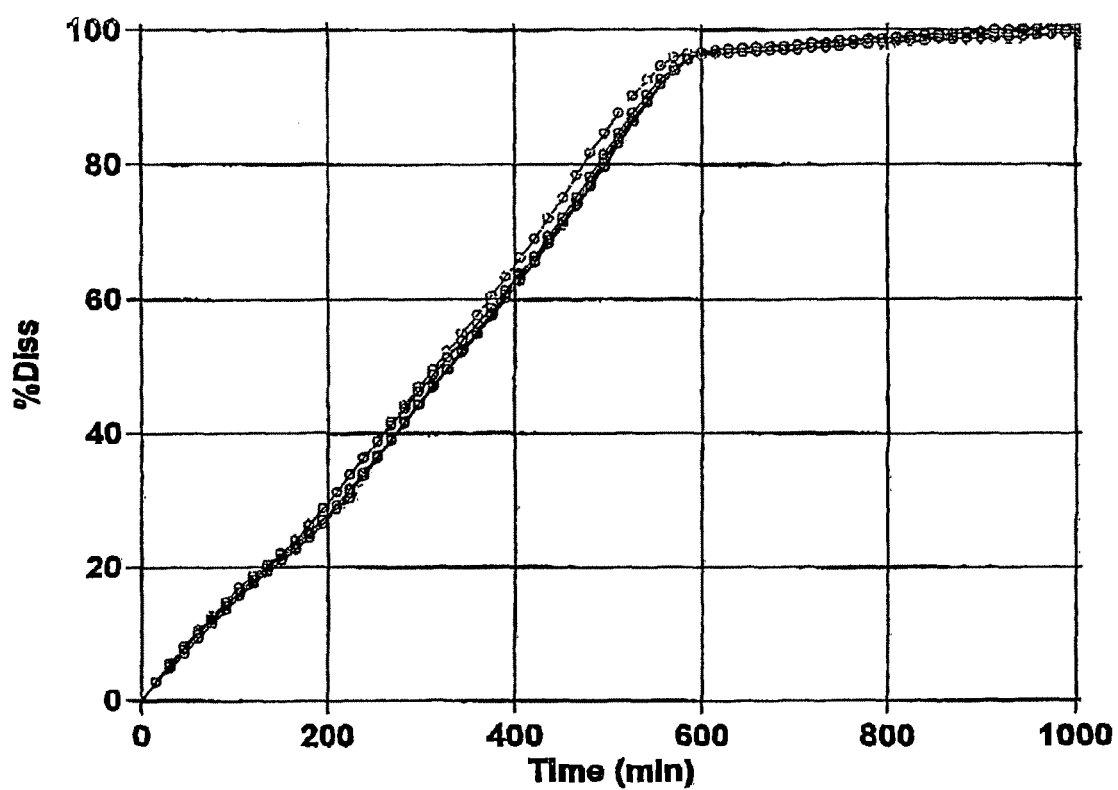

FIG. 11 shows a dissolution curve of batch 03-0003-66 paddle method, rpm 50, medium buffer pH 6.8, the formulation being a cone 3 according to table A. The dissolution time is 582 minutes.

Figure 12:
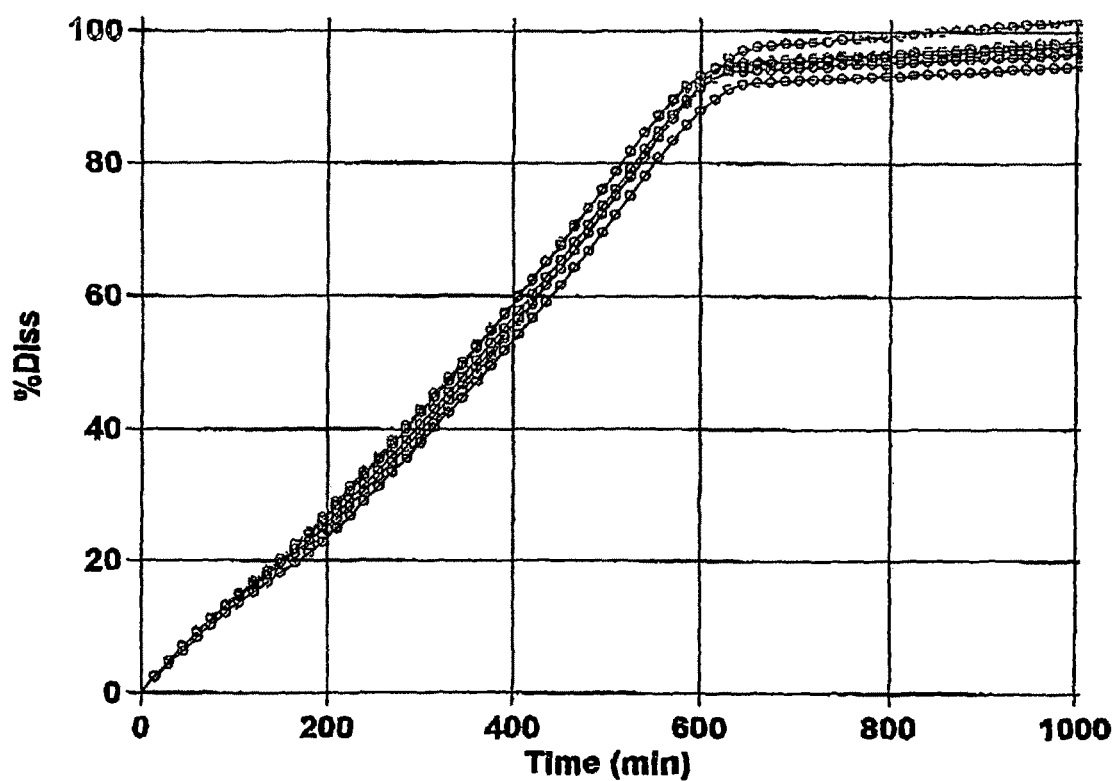

FIG. 12 shows a dissolution curve of batch 03-0003-66 paddle method, rpm 50, medium buffer pH 6.8, the formulation being a cone 4 according to table A. The dissolution time is 613 minutes.

Figure 13:
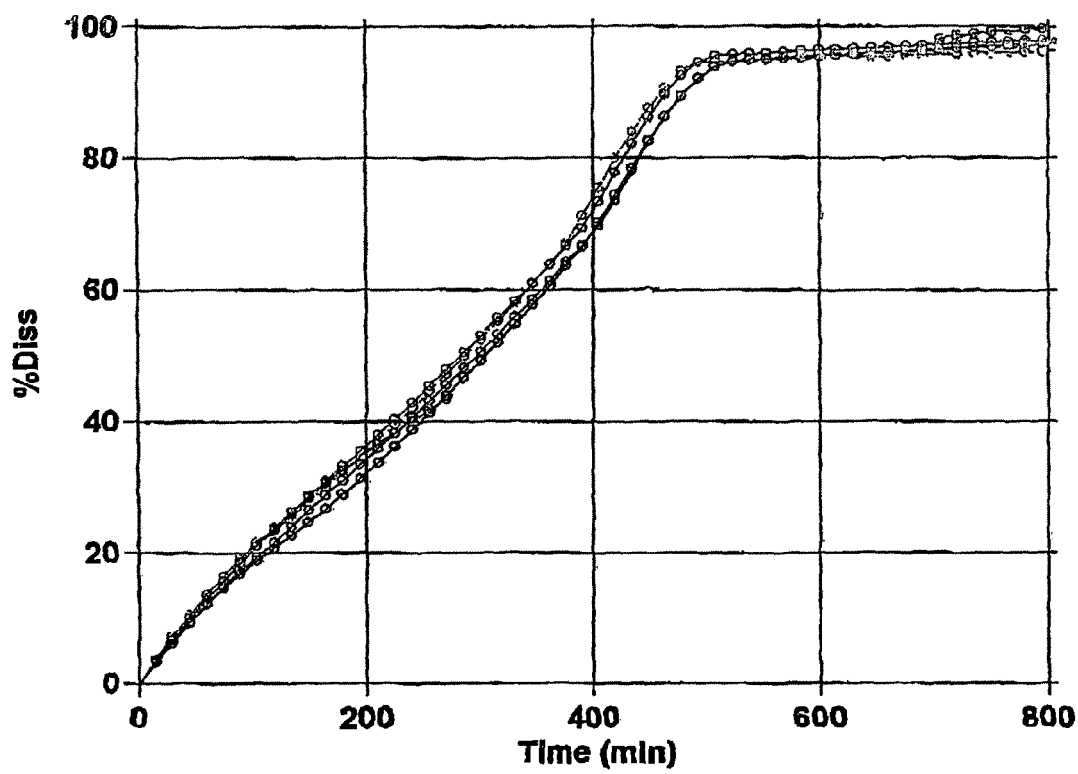

FIG. 13 shows a dissolution curve of batch 03-0025-66 basket method, rpm 100, medium buffer pH 6.8, the formulation being a cone 1 according to table A. The dissolution time is 495 minutes.

Figure 14:
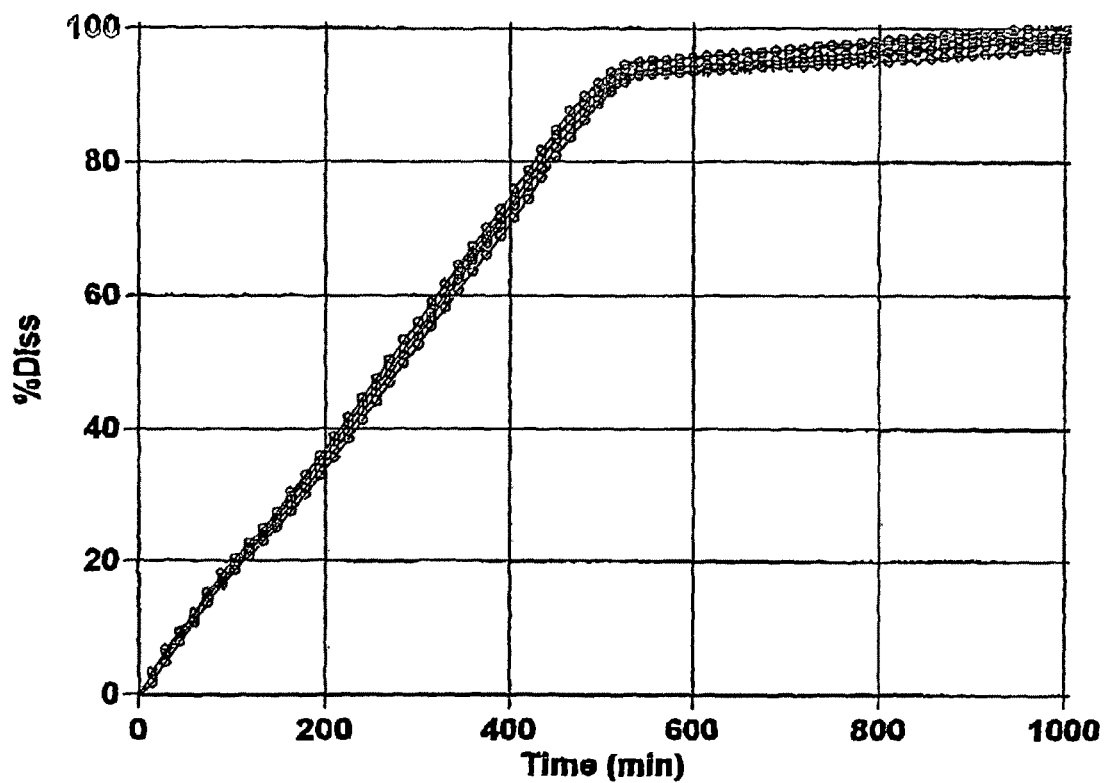

FIG. 14 shows a dissolution curve of batch 03-0026-66 paddle method, rpm 50, medium buffer pH 6.8, the formulation is a 9 mm long without cone and 150 mm$^2$. The dissolution time is 534 minutes.

Figure 15:
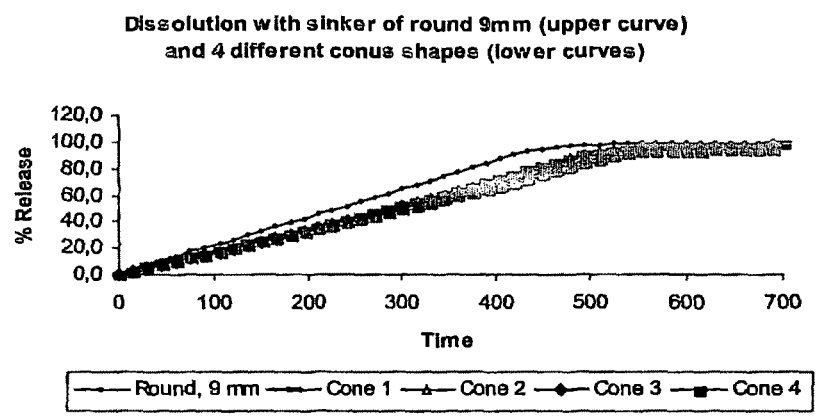

FIG. 15 shows dissolution curves for cones 1-4 together with a 9 mm round formulation by use of sinkers in the dissolution test, such as use of CAPWHT-02, a spiral coated sinker 0.900.37 inch capacity. The sinker is locked to the formulation by use of a wire. 50 rpm and buffer pH 6.8

Figure 16:
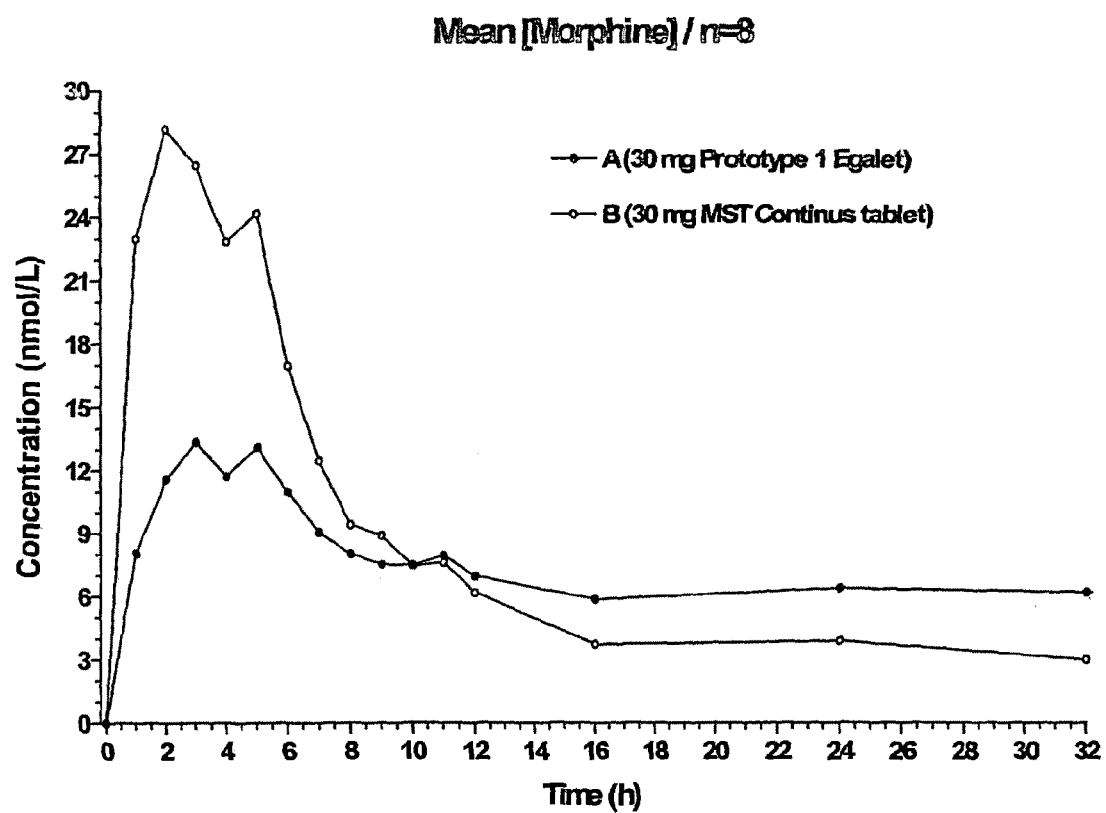

FIG. 16 shows a linear XY plot of mean plasma Morphine concentration versus time curves for Study 2 following a single dose of 1×30 mg Morphine Sulphate Egalet (Test Formulation (A), Batch 03-0005-066, shape Cone 1), or a single dose of 1×30 mg MST Continus tablet (Reference Formulation (B))/Napp, Ireland) in each study period (n=8).

Figure 17:
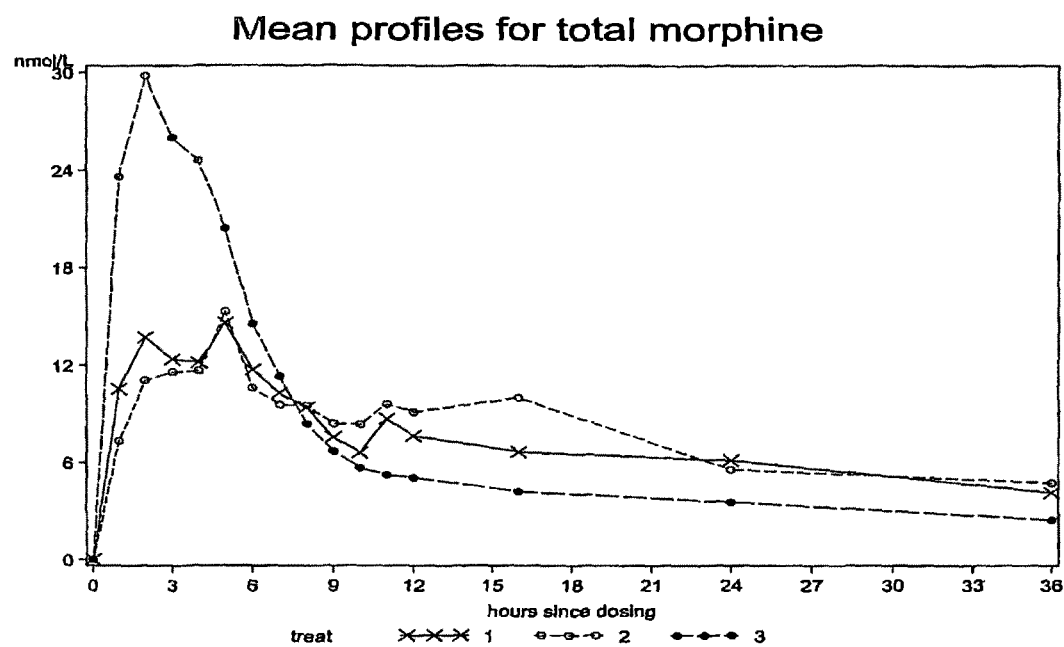

FIG. 17 shows a linear XY plot of mean plasma Morphine concentrations versus time curves for Study 3 following a single dose of 1×30 mg Morphine Sulphate Egalet® controlled release Test Formulation (A), Batch 03-0062-066, shape Cone 5 fed and fasted), or a single dose of 1×30 mg MST Continus® tablet (Reference Formulation (B)).

Figure 18:
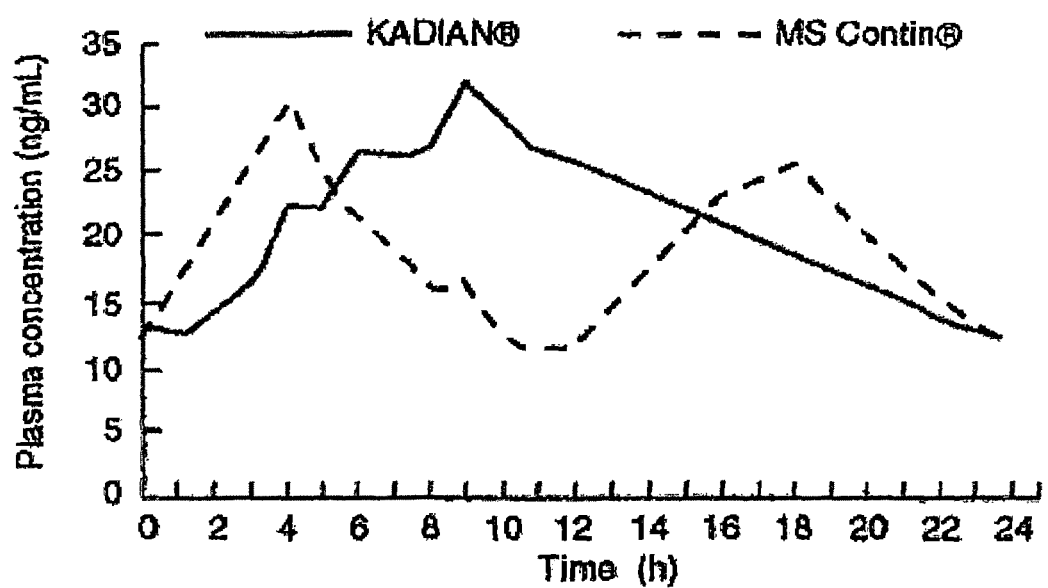

FIG. 18 shows dose normalized mean steady plasma morphine concentration from commercial available Kadian® (once a day) and an equivalent dose of a 12-hour, controlled-release morphine tablet given twice a day. Plasma concentrations are normalized to 100 mg every 24 hours, (n=24). The source of the curve is the label from the Kadian® commercial product.

Figure 19:
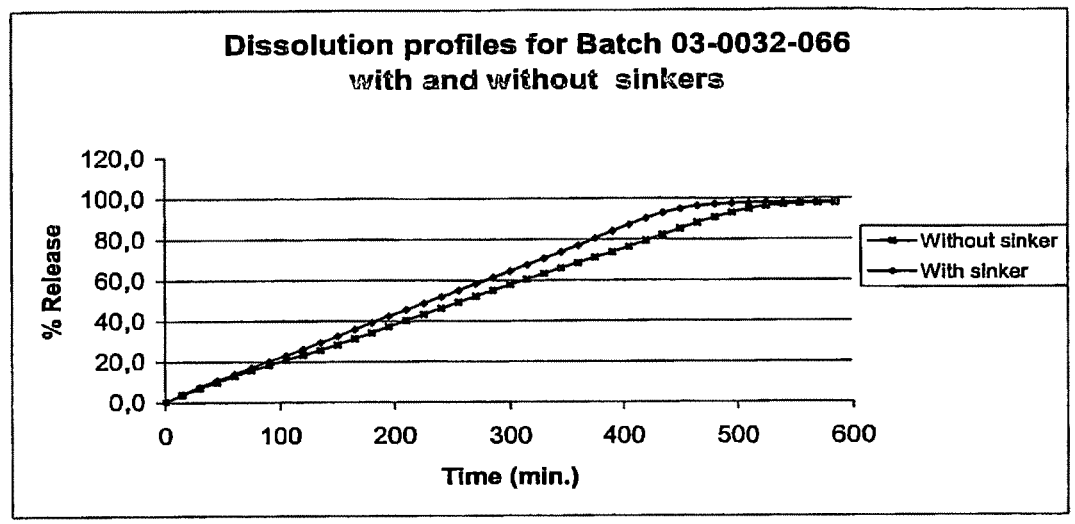

FIG. 19 shows a dissolution profile 50 rpm, buffer pH 6.8 for a Batch similar to the one of FIG. 15, a round formulation 9 mm without cone. The sinker is a CAPWHT-02.

Figure 20:
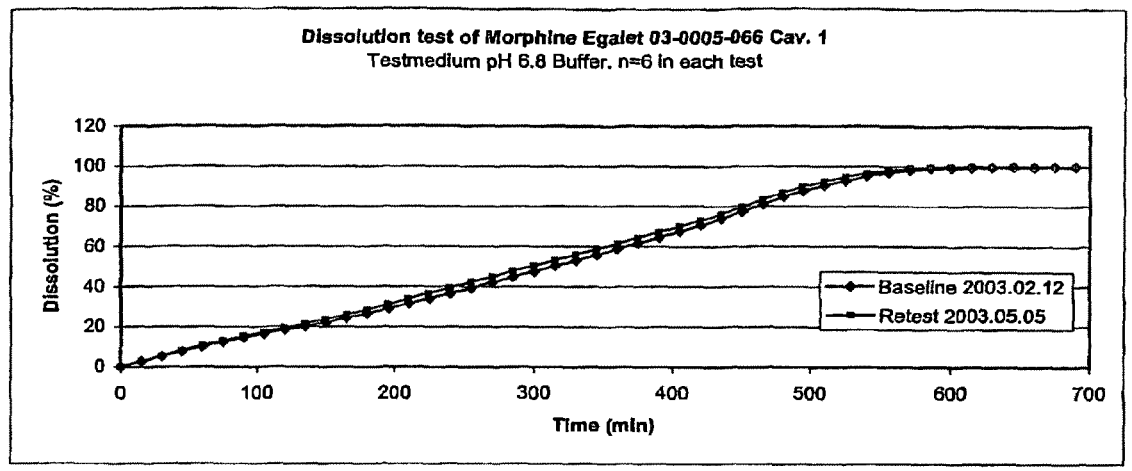

FIG. 20 shows dissolution from baseline and 3-month stability of the batch used in clinical Study 2, 03-0005-066 Cav. 1. From the baseline curve the following release rates are identified: % released; Time in min; release rate in min/%: 21%; 135 min; rate=6,428571—42%; 255 min; rate=6,071429—62%; 375 min; rate 0 6,048387—81%; 465 min; rate=5,740741. Total release 570 minutes, corresponding to 9.5 hours (dissolution without use of sinkers).

Figure 21:
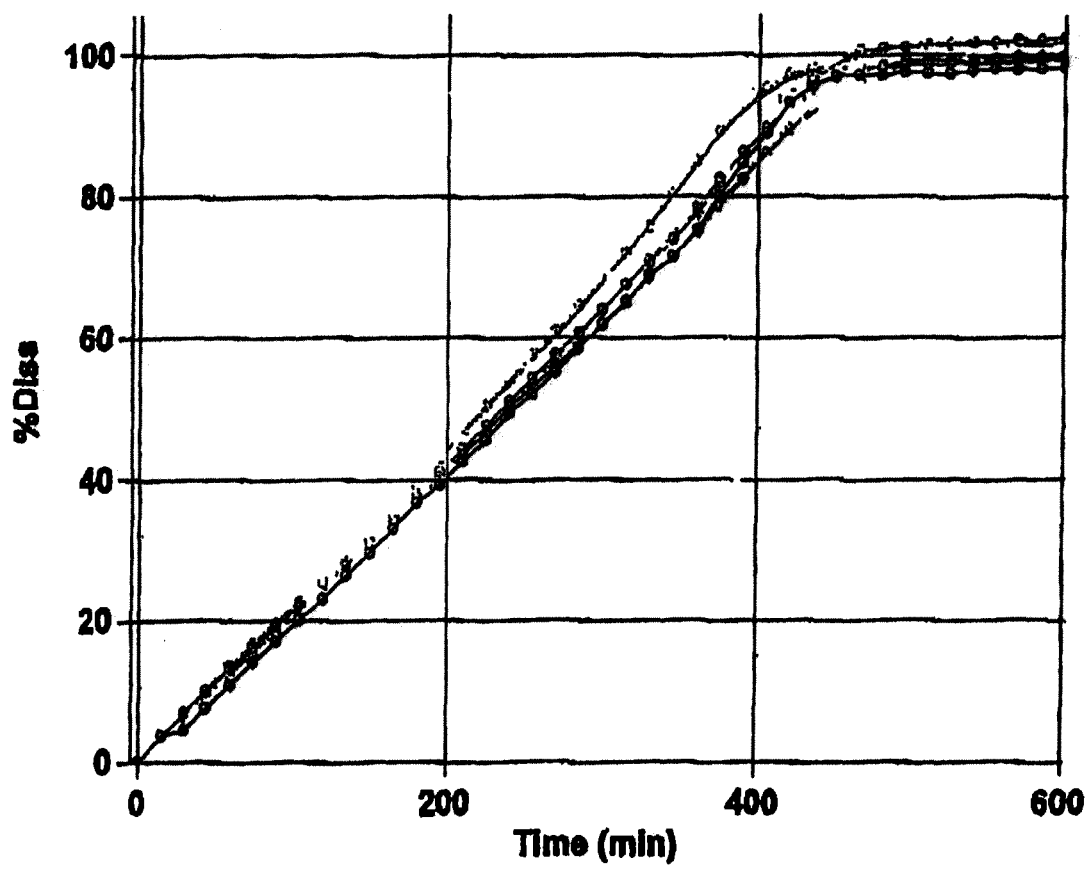

FIG. 21 shows the dissolution for Batch 03-0067-066 (conus 5) similar to Batch 03-0062-066 (study 3) with sinkers CAPWHT-02; Mean time dissolution (100%) is 458 min corresponding to 7.6 hours.

METHODS

Diffusion/Dissolution Studies
Method for Determination of Dissolution Rate of the Matrix A composition according to the invention has properties that ensure that the diffusion rate of water into the polymer matrix substantially corresponds to the dissolution rate of the polymer matrix composition into the aqueous medium. In the following is given a simple method to test these conditions.

The polymers that are suitable for use according to the present invention and which are sufficiently hydrophilic are water-soluble. When contacted with water, a sharp advancing waterfront divides the intact and not penetrated matrix from a swollen front. Under stationary conditions, a constant thickness surface layer is formed by the swollen polymer and by a high concentration of polymer in solution.

In fact, once the hydrodynamic external conditions are defined, a stationary state is reached where the rate of penetration of the moving boundary equals the rate of removal of the polymer at the external surface.

The time lapse until the quasi-stationary state is reached is called swelling time. At steady state, the dissolution rate is constant and can be defined equally by either the velocity of the retracting front of the polymer or the velocity of the front separating the pure penetrate and the liquid dissolving sub-layer. Thus, both fronts are synchronized.

When the dissolution rate equals the penetration rate (i.e. the diffusion rate) a constant thickness surface layer should be observed. The dissolving layer evolution during water conditioning should reflect the different dissolution characteristics of the materials employed. The surface layer thickness is measured as a function of time.

In order to measure the diffusion rates of water, samples may be prepared in the form of plugs fitting to the sample holder (e.g. 2 mm, 4 mm, 6 mm, 7.5 mm and 12 mm long and preferable with the same shape and volume as the desired dosage unit). The sample holder is prepared by translucent glass in a tubular shape and with noticeable marks indicated with a specific distance.

The test proceeds as follows: Place 1 plug incorporated into the glass tube in a vessel—optionally with a water soluble dye (e.g. $Cu^{2+}$)—and the plug/glass tube is placed in a dissolution apparatus e.g. according to monograph: USP 24, page 1941-1950, which is hereby incorporated by reference (see FIG. 1A). By employment of the USP method it is possible to determine the diffusion rate as well as the dissolution rate in the same experiment. The copper ions are blue-colored so they are visually detectable and due to the metric scale on the tube, the diffusion rate can be calculated (unit is length/time). The dissolution rate is determined by determining the amount of substance (e.g. active substance) released and at the same time determining the length of the matrix composition that has been eroded. Thus, the dissolution rate is also in length/time units. As the dissolution profile easily can be obtained from the data measured, a simple means for the determination of whether the release follows zero order is to investigate the dissolution profile and see whether linearity is present.

Agitation is provided, and the length of the front of matrix is measured at desired time intervals as a function of time. The measurement may be a simple visual identification of the marks on the glass tube. For comparative test, the same set of test conditions is used.

When the dissolution rate equals the penetration rate a constant thickness surface layer is observed. The different dissolving layers in different matrices obtained during the water contact, reflect the different dissolution characteristics of the matrix. The thickness of the surface layer as a function of time is then compared. The specific aqueous medium may be selected individually.

Dissolution Test

Dissolution tests were performed in accordance with the USP 24, NF 19, (711), Dissolution, Apparatus 2 equipped with a paddle. The dissolution medium was 0.1 N hydrochloric acid during the first 120 min, which was then substituted with a buffer solution pH 6.8. The volume of the dissolution medium was 1000 ml and the rotation speed of the paddle was 120 rpm during the first 120 min and then 50 rpm. Samples were withdrawn at suitable time intervals and analysed for content of opioid by means of UV spectrometry at a wavelength of 284 nm.

EXAMPLES

A general method for the preparation of a controlled release composition is described below.
Preparation of the Matrix Composition An accurate amount of the polymer (i.e. in the examples below: the polyethylene oxide) is loaded into a MTI mixer followed by an accurate amount of the active substance and of the pharmaceutically acceptable excipients(s), if any. The mixing is performed at 2000/1800 rpm and at a time period of from 8 min to 20 min. At the start of the mixing the temperature is about 19° C. and the final temperature of the mixture is about 40-48° C. The mixture is then allowed to cool to room temperature and is ready to be fed into an injection moulding machine.

When TPGS is included in the composition, TPGS and PEO are premixed by adding melted TPGS to PEO followed by mixing in a mortar with piston and gambling cards.

Preparation of the Coating Composition

The coating composition was prepared by first adding the ethylcellulose then cetostearyl alcohol, and finally the titanium dioxide to an MTI-Mixer at a temperature about 21° C. After mixing for nearly 9 min at 1000 rpm (I: 0.9 A) the mixer was stopped (temperature about 46° C.) and the adhered material manually incorporated into the mixture. The mixture was left to cool for about 10 minutes. The mixing is then finalized with a short high-speed mix in order to minimize lumps formation. The mixture was then allowed to cool to room temperature, after which it had a suitable consistency for being fed into an injection moulding machine.

Example of Coat Composition

| | | BATCH: 58-014-01-013 | | | |
|---|---|---|---|---|---|
| % | Batch | Material | amount (g) | Weight (g) | step |
| 79 | 991207-A | Ethocel | 632 | 632 | 1 |
| 20 | 990426-B | Cetylstearyl Alcohol | 160 | 160.1 | 2 |
| 1 | 97051301 | TiO$_2$ | 8 | 8.0 | 3 |
| 100 | | total | 800 | 800.1 | |

The final dosage units may be prepared according to two different methods. In one method, the coat and the matrix moulded individually followed by a manually incorporation of the moulded matrix plug into the moulded coat. The moulding machine used is an Arburg Allrounder 220 S 250/60.

In the second method, the coat and matrix are moulded in one process where the coat is moulded in a first step and the matrix is moulded directly into the coat in a second step. The moulding machine used is Arburg Allrounder 420 V 800-60135.

Examples

Example 1

Preparation of a Morphine Containing Controlled Release Composition According to the Invention A composition (batch No. 01-0112-066) according to the invention was prepared from the following ingredients:

| Matrix | |
|---|---|
| Polyethylene oxide 200,000 | 83.5% w/w |
| Morphine sulfate | 16.5% w/w |

The coating and the matrix were prepared as described above. The composition was 9 mm long and had elliptic formed surfaces.

The composition was subjected to the dissolution test described above. The following results were obtained:

| Time (hours) | % w/w release morphine sulfate from the composition |
|---|---|
| 1 | 19.48 |
| 2 | 33.64 |
| 3 | 44.22 |
| 4 | 55.59 |
| 5 | 70.11 |
| 6 | 80.70 |
| 7 | 91.30 |
| 8 | 96.65 |

Figure 2:
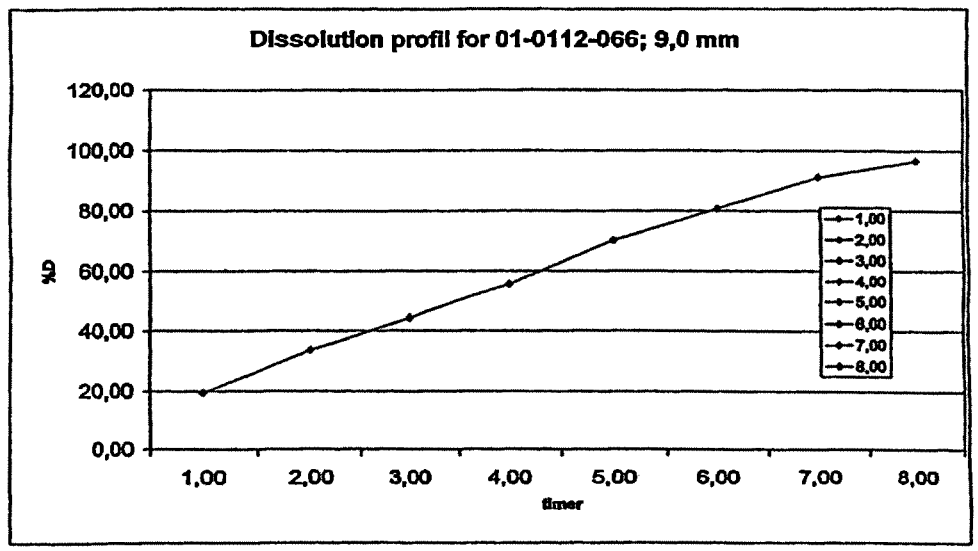
FIG. 2 is the dissolution profile from the composition of Example 1.

The result is also shown in FIG. 2 and the release corresponds to a zero order release.

Example 2

Preparation of Morphine-Containing Compositions According to the Invention

In the table below is given details on the composition of 4 different morphine compositions. The content of morphine sulphate in all compositions corresponds to 30 mg morphine sulphate. The volumes of the different compositions were the same, whereas the diameter of the open-end surfaces varies.

| | | Composition (% w/w) | | | | |
|---|---|---|---|---|---|---|
| No. | Length/mm | PEO 200.000 | Morphine Sulphate | TPGS | AlO$_2$, 3H$_2$O | Mannitol |
| 1B | 7.5; Ellipse$^a$ | 76.5 | 18.7 | 2.5 | 2.3 | |
| 2B | 12; round$^b$ | 68.7 | 18.7 | 2.6 | | 10.0 |
| 2A | 9; round$^c$ | 69.9 | 17.5 | 2.6 | | 10.0 |
| 1A | 9; round$^d$ | 77.3 | 17.9 | 2.5 | 2.4 | |

$^a$150 mm$^3$/20 mm$^2$
$^b$137 mm$^3$/diameter 5 mm
$^c$150 mm$^3$/16.67 mm$^2$
$^d$150 mm$^3$/16.67 mm$^2$ Accordingly, interesting embodiments according to the invention are compositions comprising
  i) Morphine (e.g. as morphine sulphate) 10-30% w/w such as, e.g., from 15 to 25% w/w or from 15 to 20% w/w,
  ii) PEO 200,000 50-90% w/w such as, e.g., from about 60 to about 85% w/w, from about 70 to about 85% w/w or from about 75 to about 80% w/w,
  iii) TPGS 0-5% w/w such as, e.g., from about 1.5 to about 3% w/w,
  iv) Aluminium oxide 0-5% w/w such as, e.g. from about 2 to about 3% w/w, and
  v) Mannitol 0-20% w/w such as, e.g., from about 5 to about 15% w/w.

All compositions demonstrated 6 months accelerated stability at 40° C./75% RH and 12 months stability at 25° C./75% RH. In all compositions each single impurity is below 0.1% w/w.

In the following is given the data for the dissolution profiles of each composition:
Composition 2A (See FIG. 3-2A):

| Time/h | % active substance dissolved | |
|---|---|---|
| 0.0 | −0.36 | |
| 1.0 | 23.45 | 20.0 |
| 2.0 | 41.3 | 35.2 |

-continued

| Time/h | % active substance dissolved | |
|---|---|---|
| 3.0 | 59.5 | 50.7 |
| 4.0 | 75.93 | 64.7 |
| 5.0 | 90.83 | 77.4 |
| 6.0 | 107.34 | 91.5 |
| 6.5 | 113.26 | 96.6 |
| 7.0 | 116.67 | 99.4 |
| 7.5 | 117.24 | 100 |
| 8.0 | 117.28 | 100 |

Composition 2B (See FIG. 3-2B)

| Time/h | % active substance dissolved | |
|---|---|---|
| 0.0 | −0.48 | |
| 1.0 | 19.22 | 16.9 |
| 2.0 | 34.44 | 30.0 |
| 3.0 | 44.3 | 39.0 |
| 4.0 | 55.52 | 48.8 |
| 5.0 | 66.13 | 58.2 |
| 6.0 | 76.93 | 67.7 |
| 7.0 | 87.19 | 76.7 |
| 8.0 | 98.11 | 86.3 |
| 9.0 | 109.04 | 96.0 |
| 9.5 | 111.26 | 97.8 |
| 10.0 | 112.63 | 99.1 |
| 10.5 | 113.48 | 100 |
| 11.0 | 113.66 | 100 |

Composition 1B (See FIG. 3-1B)

| Time/h | % active substance dissolved | |
|---|---|---|
| 0.0 | −0.47 | |
| 1.0 | 30.15 | 23.7 |
| 2.0 | 55.72 | 43.9 |
| 3.0 | 77.54 | 61.1 |
| 4.0 | 97.55 | 76.8 |
| 5.0 | 117.57 | 92.6 |
| 5.5 | 124.77 | 98.2 |
| 6.0 | 126.89 | 100 |
| 6.5 | 126.93 | 100 |

Composition 1A (See FIG. 3-1A)

| Time/h | % active substance dissolved | |
|---|---|---|
| 0.0 | −0.423 | |
| 1.0 | 23.17 | 19.3 |
| 2.0 | 40.47 | 33.8 |
| 3.0 | 53.27 | 44.4 |
| 4.0 | 67.13 | 56.0 |
| 5.0 | 80.67 | 67.3 |
| 6.0 | 101.23 | 84.4 |
| 7.0 | 108.16 | 90.2 |
| 7.5 | 114.53 | 95.6 |
| 8.0 | 119.78 | 100 |

The results show that the use of mannitol or aluminiumoxide as a DDA leads to the desired zero order release of morphine sulphate from a composition according to the invention.

The above-mentioned compositions were subject to a clinical study. The clinical study is reported in the following example.

Example 3

A Single Dose, Randomized, Cross-Over, Pharmacokinetic Pilot Study on Four Different Morphine Compositions According to the Invention The objectives were to study the pharmacokinetics of morphine after administration of four different morphine compositions according to the invention. The compositions had different shape and size and the DDAs employed in order to enable a zero order dissolution profile were different (mannitol and aluminium oxide, respectively).

16 healthy male volunteers aged 20 to 40 who had given their written informed consent were included in the study.

The volunteers were screened up to three weeks prior to baseline. The first treatment was administered at the baseline visit and second treatment was administered after 2 weeks of wash out. Follow-up visits took place 30 days after the second study period.

The compositions tested were those described in Example 2 above. The dose given corresponds to 30 mg morphine sulphate.

Figure 4:
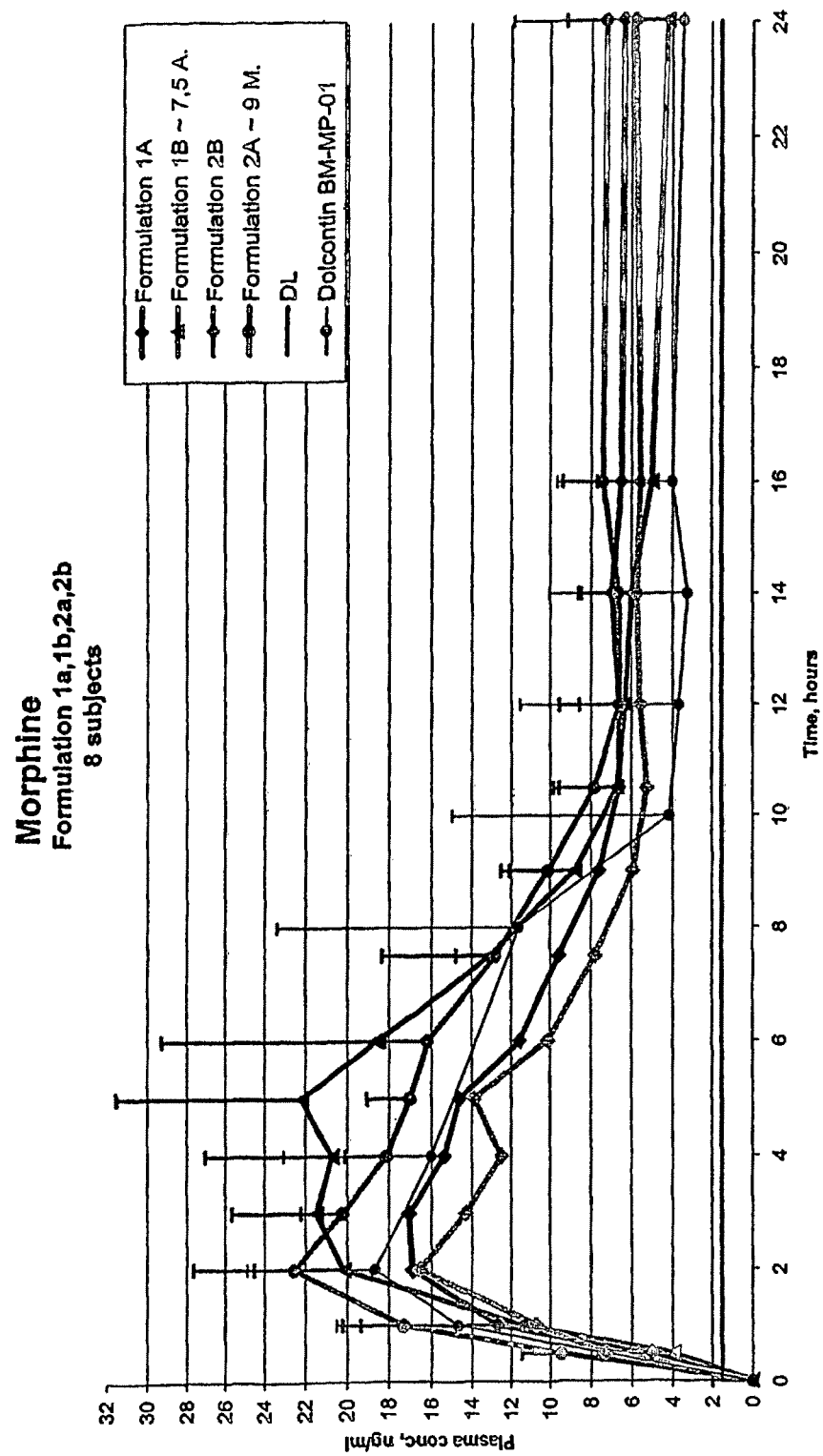
FIG. 4 shows the plasma concentration vs. time profile for the clinical study on healthy volunteers reported in Example 3.

The results of the study are shown in FIG. 4. In FIG. 4 is also included data for a comparative composition, Dolcontin. The results indicate that the shape as well as the size of the composition is important.

Figure 5:
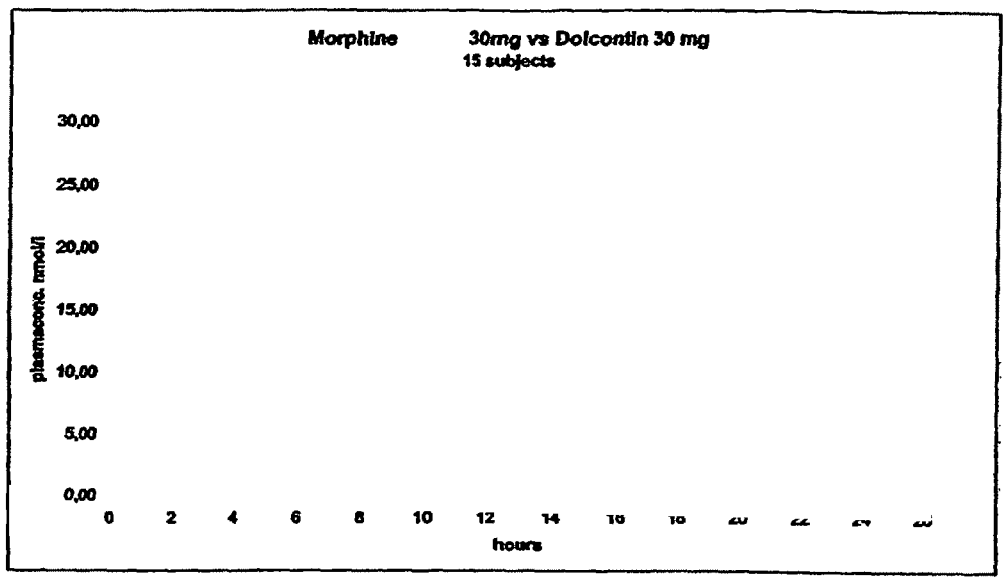
FIG. 5 shows the plasma concentration vs. time profile for the clinical study in phase II reported in Example 3.
Figure 6:
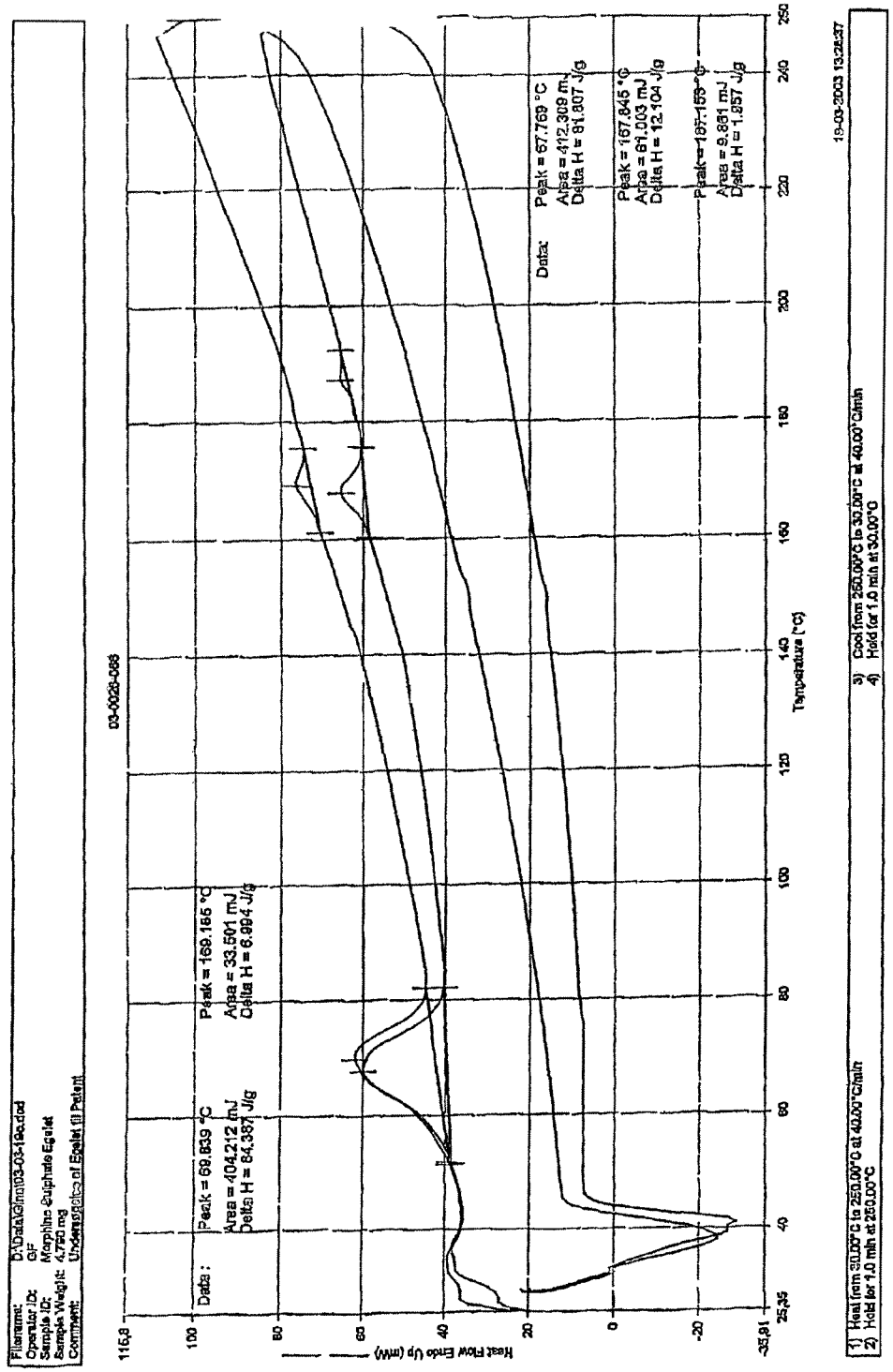
FIG. 6 shows a differential scanning calorimetric diagram of a controlled release product according to the invention comprising 17.5% morphine sulphate. The diagram demonstrated that no crystalline morphine is detected by the method.

Another clinical study has also been performed as a phase II, open, prospective, controlled study in patients with chronic pain. The study included 13 patients with chronic pain for any reason judged by the investigator as stable and in need of opioids analgesics. A composition according to the invention was tested and compared with a commercially available morphine containing composition, Dolcontin. The total morphine sulphate released from the composition according to the invention was about 20 mg (the dosage in Dolcontin was 30 mg). Although there was a difference in the amount administered, it was evident from the study that the therapeutic effect of a composition according to the invention was not different from Dolcontin, i.e. a reduction is the overall dose may be reduced by the use a zero order release composition. Moreover, the adverse effects reported were less compared to the Dolcontin composition, most likely due to the smaller amount of morphine sulphate administered. Another interesting feature is that during the study rescue medication was allowed and there was no difference in the intake of rescue medicine of patients administered with Dolcontin or with a composition according to the invention. FIG. 5 shows the plasma concentration versus time profiles from the study.

Example 4

A composition (batch No.: 03-0003-066) according to the invention was prepared from the following ingredients.

| Matrix | % w/w |
|---|---|
| PEO 200,000 LF | 69.90% |
| Morphine Sulphate Pentahydrate | 17.5% |
| Mannitol | 10% |
| TPGS | 2.6% |

Example 5

A composition (batch No.: 03-0004-066) according to the invention was prepared from the following ingredients.

| Matrix | % w/w |
| --- | --- |
| PEO 200,000 LF | 84.70% |
| Mannitol | 12.1% |
| TPGS | 3.2% |

Example 6

A composition (batch No.: 03-0005-066) according to the invention was prepared from the following ingredients.

| Matrix | % w/w |
| --- | --- |
| PEO 200,000 LF | 69.90% |
| Morphine Sulphate Pentahydrate | 17.5% |
| Mannitol | 10% |
| TPGS | 2.6% |

Example 7

A composition (batch No.: 03-0007-066) according to the invention was prepared from the following ingredients.

| Matrix | % w/w |
| --- | --- |
| PEO 200,000 LF | 69.90% |
| Morphine Sulphate Pentahydrate | 17.5% |
| Mannitol | 10% |
| TPGS | 2.6% |

Example 8

A composition (batch No.: 03-0008-066) according to the invention was prepared from the following ingredients.

| Matrix | % w/w |
| --- | --- |
| PEO 200,000 LF | 69.90% |
| Morphine Sulphate Pentahydrate | 17.5% |
| Mannitol | 10% |
| TPGS | 2.6% |

Example 9

A composition (batch No.: 03-0023-066) according to the invention was prepared from the following ingredients.

| Matrix | % w/w |
| --- | --- |
| PEO 200000 NF | 69.90% |
| Morphine Sulphate Pentahydrate | 17.5% |
| Mannitol | 10% |
| TPGS | 2.6% |

Example 10

A composition (batch No.: 03-0024-066) according to the invention was prepared from the following ingredients.

| Matrix | % w/w |
| --- | --- |
| PEO 200,000 NF | 69.90% |
| Morphine Sulphate Pentahydrate | 17.5% |
| Mannitol | 10% |
| TPGS | 2.6% |

Example 11

A composition (batch No.: 03-0025-066) according to the invention was prepared from the following ingredients.

| Matrix | % w/w |
| --- | --- |
| PEO 200,000 NF | 69.90% |
| Morphine Sulphate Pentahydrate | 17.5% |
| Mannitol | 10% |
| TPGS | 2.6% |

Example 12

A composition (batch No.: 03-0026-066) according to the invention was prepared from the following ingredients.

| Matrix | % w/w |
| --- | --- |
| PEO 200,000 NF | 69.90% |
| Morphine Sulphate Pentahydrate | 17.5% |
| Mannitol | 10% |
| TPGS | 2.6% |

The shape of the composition was 9 mm without cone.

Example 13

Four different designs have been tested in order to increase the rate of dissolution in the later hours compared to the initial hours in order to counteract the very fast and rapid absorption of morphine in patients and thereby decrease the initial peak in morphine concentration. The compositions tested were those from Examples 4, 6, 11 and 12. Cone 1 is tested in a similar PK pilot clinical trial as described above.

Table A demonstrates the specific dimensions of the formulation according to the inventions wherein one end of the tubular shape has a cone configuration and dimensions according to FIG. 1B and as follows:

TABLE A (confer FIG. 1B)

| D mm | B mm | A mm | C mm | Volume mm$^2$ | Cone Shape |
| --- | --- | --- | --- | --- | --- |
| D 9.00 | B 4.89 | A 3.00 | C 3.00 | 150.00 | 1 |
| D 10.00 | B 4.63 | A 3.00 | C 3.50 | 150.00 | 2 |
| D 10.00 | B 4.63 | A 3.50 | C 4.85 | 150.00 | 3 |
| D 11.00 | B 4.29 | A 3.50 | C 3.50 | 150.00 | 4 |
| D 9.00 | B 4.81 | A 3.50 | C 3.00 | 150.00 | 5 |

The corresponding dissolution curves for cones 1-4 appear from FIGS. 7-13. FIG. 15 shows corresponding dissolution curves for cones 1-4 together with a 9 mm round formulation by use of sinkers in the dissolution test.

Example 14

Clinical Study 2

Objective: To compare the pharmacokinetic profile of Morphine Sulphate Egalet® 30 mg with that of a reference product, MST Continus® 30 mg tablets, in healthy male volunteers Study design: A single-dose, randomised, crossover study in healthy male volunteers.

Test drug Morphine Sulphate Egalet® 30 mg controlled release formulation, 1×30 mg, Batch 03-0005-066 (Example 6, Conus 1). Reference drug: MST Continus® 30 mg tablet 1×30 mg, Batch 110881. Test for content of test and reference drug after finalizing clinical study and study report demonstrated that the content of the test drug was 12% lower than the reference drug. The result is not corrected for that difference in Table B.

Statistical Methods:

Descriptive statistics as follows were calculated for each variable: arithmetic mean (Mean), geometric mean (GeoM), standard deviation (SD), coefficient of variation (CV), absolute minimum (Min), maximum (Max) and median (Med). The pharmokinetic profiles of the test and reference formulations were compared through a comparison of descriptive statistics. Data is presented with 90% CI and intra-individual CV.

TABLE B

Results: Morphine
Pharmacokinetics:
Table 1: Summary statistics Test A v Reference B

| Variable | Arith. Mean | | Std. Dev. | | Range | |
|---|---|---|---|---|---|---|
| | Test | Ref | Test | Ref | Test | Ref |
| $AUC_{0-\infty}$ | 434.27 | 333.90 | 238.07 | 173.15 | 173.59-799.13 | 160.41-641.08 |
| $AUC_{0-12}$ (nmol/L · h) | 111.94 | 189.26 | 75.58 | 110.72 | 60.63-289.82 | 93.22-416.11 |
| $AUC_{0-24}$ (nmol/L · h) | 185.90 | 238.72 | 111.31 | 127.43 | 101.35-441.54 | 121.94-486.81 |
| $AUC_{0-32}$ (nmol/L · h) | 236.01 | 265.94 | 137.81 | 136.83 | 131.43-542.66 | 142.39-531.92 |
| $C_{max}$ (nmol/L) | 15.90 | 32.45 | 8.31 | 19.67 | 8.44-33.70 | 14.40-71.80 |
| $C_{12h}$ (nmol/L) | 6.95 | 6.16 | 5.33 | 3.94 | 3.26-19.30 | 2.12-12.70 |
| $C_{av(0-12)}$ (nmol/L) | 9.33 | 15.77 | 6.30 | 9.23 | 5.05-24.15 | 7.77-34.68 |
| $t_{max}$ (nmol/L) | 3.50 | 2.13 | 1.31 | 1.36 | 2.0-5.0 | 1.0-5.0 |
| C ≥ 50% | 10.60 | 5.84 | 4.50 | 2.33 | 5.97-19.80 | 3.14-10.29 |
| C ≥ 75% | 2.67 | 3.18 | 1.02 | 1.72 | 1.68-4.72 | 1.09-5.42 |
| $t_{1/2}$ (h) | 28.38 | 17.78 | 13.98 | 11.68 | 8.71-49.56 | 6.88-38.40 |
| MRT (h) | 42.07 | 20.82 | 18.70 | 10.70 | 17.56-71.64 | 9.78-39.01 |
| $K_{el}$ ($h^{-1}$) | 0.0319 | 0.0543 | 0.0209 | 0.0292 | 0.0140-0.0796 | 0.0181-0.1007 |
| % Residual | 42.71 | 19.04 | 16.10 | 12.91 | 13.30-63.98 | 4.02-37.94 |

TABLE 2

Confidence limits, point estimates and CV Test A v Reference B

| Variable | Geom. Mean | | Point Estimate | 90% Confidence Limits | Intra-Subject CV | Inter-Subject CV |
|---|---|---|---|---|---|---|
| | Test | Ref | | | | |
| $AUC_{0-\infty}$ | 380.01 | 300.16 | 126.60% | 100.14%-160.07% | 24.50% | 54.07% |
| $AUC_{0-12}$ (nmol/L · h) | 97.52 | 166.57 | 58.54% | 52.03%-65.87% | 12.18% | 66.34% |
| $AUC_{0-24}$ (nmol/L · h) | 165.63 | 213.74 | 77.49% | 68.30%-87.92% | 13.05% | 55.94% |
| $AUC_{0-32}$ (nmol/L · h) | 210.26 | 240.11 | 87.57% | 79.39%-96.59% | 10.12% | 53.22% |

TABLE 2-continued

Confidence limits, point estimates and CV Test A v Reference B

| Variable | Geom. Mean Test | Geom. Mean Ref | Point Estimate | 90% Confidence Limits | Intra-Subject CV | Inter-Subject CV |
|---|---|---|---|---|---|---|
| $C_{max}$ (nmol/L) | 14.39 | 28.38 | 50.71% | 42.34%-60.74% | 18.73% | 69.94% |
| $C_{12h}$ (nmol/L) | 5.82 | 5.04 | 115.64% | 82.40%-162.29% | 35.97% | 69.36% |
| $C_{av(0-12)}$ (nmol/L) | 8.12 | 13.88 | 58.52% | 52.02%-65.84% | 12.18% | 66.35% |
| $t_{max}$ (nmol/L) | 3.28 | 1.82 | +1.25 h (158.82%) | -0.5 h to +3.0 h (76.47%-241.18%) | — | 52.29% |
| $C \geq 50\%$ | 9.87 | 5.47 | 180.48% | 108.31%-300.76% | 56.41% | 51.65% |
| $C \geq 75\%$ | 2.52 | 2.71 | 92.90% | 55.90%-154.38% | 56.07% | 47.52% |
| $t_{1/2}$ (h) | 25.14 | 14.90 | 168.81% | 96.48%-295.36% | 62.70% | 58.92% |
| MRT (h) | 38.50 | 18.74 | 205.46% | 132.35%-318.96% | 47.69% | 58.38% |
| $K_{el}$ (h$^{-1}$) | 0.0276 | 0.0465 | 59.24% | 33.86%-103.65% | 62.70% | 62.90% |

Safety: Six mild adverse events were recorded in three volunteers. Three AEs were possibly or probably related to the study medication and of these 3 AEs, 1 probably and 1 possible was related to the reference MST Continus formulation and 1 possible AE was related to the test product.

The mean plasma curves from Study 2 are shown in FIG. 16.

Example 15

In order to further improve the plasma profile obtained in Study 2, a geometric amendment was made to the shape of the formulation. The amendment aimed at a decrease in the initial release from the formulation as the in vitro absorption rate of morphine is very rapid in the stomach and upper intestinal tract. Accordingly, from the information from the dissolution profile and the corresponding in vivo plasma concentration of the formulation observed in Study 2 it appeared desirable to decrease initial release and increase release by the end of the release period. This was obtained by tailoring the geometry by decreasing the longest diameter from 4.89 to 4.81 mm and increasing the smallest diameter from 3 to 3.5 mm. The length of the cone was kept on 3 mm, and the total length of the formulation was kept on 9 mm. A matrix similar to the one of Batch 03-0005-066 was used.

Example 16

Clinical Study 3

Objective: To compare the pharmacokinetic profile of Morphine Sulphate Egalet® 30 mg in fasted and fed state with that of a reference product, MST Continus® 30 mg tablets, in healthy volunteers Study design: A single-dose, randomised, two treatment, three-period cross-over pharmacokinetic study in healthy male volunteers.

Test drug Morphine Sulphate Egalet® 30 mg controlled release formulation, 1×30 mg, Batch 03-0062-066.

Reference drug: MST Continus® 30 mg film coated tablet 1×30 mg,

The results obtained are shown in the following tables

| Study 3 | Concmax: |
|---|---|
| Egalet (30 mg) fasted data for 0-36 hours: nmol/L minutes | Mean 18.31125 Std Deviation 9.56966 Median 17.00000 Variance 91.57841 Geomean = exp(2.81505161) = 16.69 |
| Tmax: | AUCM |
| Mean 226.0417 Std Deviation 139.71228 Median 180.0000 Variance 19520 | Mean 13792170 Std Deviation 5910802 Median 12418610 Variance 3.49376E13 Geomean = exp(16.3723464) = 12894353 |
| AUCT: | MRT |
| Mean 15537.12 Std Deviation 6425 Geomean = exp(9.58681953) = 14571 | Mean 888.1877 Std Deviation 77.52388 Median 888.9335 Variance 6010 Geomean = exp(6.78552683) = 885 |

| Study 3 | AUCt |
|---|---|
| Egalet (30 mg) fed: data for 0-36 hours: nmol/L minutes | Mean 16197.57 Std Deviation 7188 Median 13545.78 Variance 51671134 Geomean = exp(9.61546345) = 14994 |
| Concmax | MRT |
| Mean 17.89167 Std Deviation 7.52664 Median 15.60000 Variance 56.65036 Geomean = exp(2.80673198) = 16.6 | Mean 877.8806 Std Deviation 64.15725 Median 874.8590 Variance 4116 Geomean = exp(6.77499572) = 876 |

-continued

| AUCM | Tmax |
|---|---|
| Mean 14279619.2 | Mean 335.2500 |
| Sum Observations 342710860 | Std Deviation 236.42762 |
| Geomean = exp(16.3904592) = 13129865 | Median 300.0000 |

| Study 3 | AUCt |
|---|---|
| MST Continus (30 mg): data for 0-36 hours: nmol/L minutes | Mean 15771.56 Std Deviation 5573 Median 13463.49 Variance 31058523 Geomean = exp(9.61720701) = 15021 |

| Concmax | Tmax |
|---|---|
| Mean 33.44167 Std Deviation 12.94009 Median 30.70000 Variance 167.44601 Geomean = exp(3.4451475) = 31.3 | Mean 130.0000 Std Deviation 52.08688 Median 120.0000 Variance 2713 |

| AUMC | MRT |
|---|---|
| Mean 9638437 Std Deviation 3586698 Median 8648532 Variance 1.28644E13 Geomean = exp(16.0333294) = 9187000 | Mean 615.6140 Std Deviation 71.48470 Median 630.5723 Variance 5110 Geomean = exp(6.41612235)) = 611 |

MP-EG-001: Total Morphine:
Summary of Duration in Minutes Above 33% of Cmax

| Egalet fasted | | | | | |
|---|---|---|---|---|---|
| Mean | Median | Lower Minimum | Upper Quartile | Quartile | Maximum |
| 1234.6 (20.6 h) | 1143.3 | 361.0 | 742.9 | 1800.7 | 2131.8 |

| Egalet fed | | | | | |
|---|---|---|---|---|---|
| Mean | Median | Lower Minimum | Upper Quartile | Quartile | Maximum |
| 1255.1 (20.9 h) | 1274.1 | 365.8 | 851.0 | 1661.9 | 2094.8 |

| MST Continus | | | | | |
|---|---|---|---|---|---|
| Mean | Median | Lower Minimum | Upper Quartile | Quartile | Maximum |
| 386.3 (6.4 h) | 396.8 | 261.3 | 340.7 | 423.4 | 478.9 |

| Study 3 Treatment | Conc Max from curve* h = 5 | Conc, h = 10 nmol/L | Conc, h = 12 nmol/L | Conc, h = 16 nmol/L | Conc, h = 24 nmol/L | Mean Cmax, nmol/L | Tmax, h |
|---|---|---|---|---|---|---|---|
| A; Test fasted | 14.43 | 6.48583 | 7.46125 | 6.60708 | 6.09333 | 18.31 | 3.8 |
| A; % of mean Cmax | | 35% | 41% | 36% | 33% | | |
| A; % of curve Cmax | | 45% | 52% | 46% | 42% | | |
| B; Test fed | 15.36 | 8.19958 | 8.92417 | 9.97750 | 5.50292 | 17.89167 | 5.6 |
| B; % of mean Cmax | | 46% | 50% | 56% | 31% | | |
| B; % of curve Cmax | | 53% | 58% | 56% | 36% | | |
| C; Reference MST Continus | | 5.71375 | 5.08292 | 4.19208 | 3.54261 | 30.70000 | 2.2 |
| C; % of mean Cmax | | 19% | 17% | 14% | 12% | | |

*for treatment A and B has been performed based on mean individual Cmax as well as for Cmax from values of mean curve (FIG. 17) for possible comparison with other treatments where mean Cmax is not available. It is noted that the values when compared with the curve Cmax is considerable higher than when compared with mean Cmax Summary of Duration in Minutes Above 50% of Cmax

| Egalet fasted | | | | | |
|---|---|---|---|---|---|
| Mean | Median | Lower Minimum | Upper Quartile | Quartile | Maximum |
| 551.4 (9.2 h) | 434.8 | 106.0 | 315.0 | 681.1 | 2111.3 |

| Egalet fed | | | | | |
|---|---|---|---|---|---|
| Mean | Median | Lower Minimum | Upper Quartile | Quartile | Maximum |
| 681.4 (11.3 h) | 617.8 | 233.9 | 370.5 | 946.5 | 1233.7 |

| MST Continus | | | | | |
|---|---|---|---|---|---|
| Mean | Median | Lower Minimum | Upper Quartile | Quartile | Maximum |
| 272.5 (4.5 h) | 274.4 | 136.8 | 241.0 | 301.8 | 404.4 |

Summary of Duration in Minutes Above 75% of Cmax

| Egalet fasted | | | | | |
|---|---|---|---|---|---|
| Mean | Median | Lower Minimum | Upper Quartile | Quartile | Maximum |
| 219.8 (3.6) | 159.0 | 47.3 | 92.2 | 227.6 | 1155.5 |

| Egalet fed | | | | | |
|---|---|---|---|---|---|
| Mean | Median | Lower Minimum | Upper Quartile | Quartile | Maximum |
| 236.1 (3.9 h) | 211.9 | 49.6 | 113.9 | 320.4 | 747.5 |

| MST Continus | | | | | |
|---|---|---|---|---|---|
| Mean | Median | Lower Minimum | Upper Quartile | Quartile | Maximum |
| 164.7 (2.7 h) | 174.8 | 64.4 | 109.9 | 212.6 | 282.3 |

The invention claimed is:

1. A controlled release oral pharmaceutical composition, comprising
   (i) an erodible matrix composition having a cylindrical shape having a long axis and a conus-shaped end portion having a largest diameter and a smallest diameter, wherein the conus-shaped end portion extends across from about 5% to about 50% of the long axis of the cylindrical shape and the ratio of the largest diameter to the smallest diameter of the conus-shaped end portion is from about 2.5 to 1 to about 1.2 to 1, wherein the matrix composition comprises:
      (a) a first polyethylene oxide having a molecular weight selected from the group consisting of about 100,000 daltons, about 150,000 daltons, about 200,000 daltons, about 250,000 daltons, about 300,000 daltons and about 400,000 daltons,
      (b) a therapeutically effective amount of an opioid or a pharmaceutically acceptable salt, complex, solvate or anhydrate thereof, or a mixture thereof and, optionally,
      (c) one or more pharmaceutically acceptable excipients, and
   (ii) a coating on the matrix composition, comprising
      (a) a material selected from the group consisting of cellulose acetate, polyamide, polyethylene, polyethylene terephthalate, polypropylenem polyurethane, polyvinyl acetate, polyvinyl chloride, silicone rubber, latex, polyhydroxybutyrate, polyhydroxyvalerate, teflon, polylactic acid or polyglycolic acid and copolymers thereof, ethylene vinyl acetate (EVA), styrene-butadienestyrene (SBS) and styrene-isoprene-styrene (SIS), and
      (b) a plasticizer,
   wherein the coating has at least one opening exposing a surface of the conus-shaped end portion of the matrix composition, thereby allowing controlled release of said opioid by erosion of said matrix surface, wherein the surface area exposed increases during erosion of the conus-shaped end portion,
   wherein the coating and the matrix composition are formed by injection molding,
   wherein the composition exhibits zero order release of at least 80% of the opioid contained in the composition, and
   wherein about 75% w/w of the opioid is released from the composition within 4-10 hours when subject to a dissolution test in accordance with USP 24, NF 19, (711), Dissolution, employing Apparatus 2 equipped with a paddle using 1000 mL of 0.1 N hydrochloric acid dissolution medium and a paddle rotation of 120 rpm for the first 120 minutes, and a buffer solution having a pH of 6.8 and a paddle rotation of 50 rpm thereafter.

2. The pharmaceutical composition of claim 1, wherein the opioid is selected from the group consisting of alfentanil, allylprodine, alphaprodine, aniloridine, benzylmorphine, bezitramide, buprenorphine, butophanol, clonitazene, codeine, cyclazocine, desomorphine, dextromoramide, dezocine, diapromide, dihydrocodeine, dihydromorphine, dimenoxadol, dimephetanol, dimethylthiambutene, dioxaphetyl butyrate, dipipanone, eptazocine, ethoheptazine, ethylmethylthiambutene, ethylmorphine, etonitazene, fentanyl, heroin, hydrocodone, hydromorphone, hydroxypethidine, isomethadone, dextropropoxyphene, ketobemidone, levallorphan, levorphanol, levophenacylmorphan, lofentanil, meperidine, meptazinol, metazocine, methadone, metopon, morphine, morphine 6-glucuronide, morphine 3-glucuronide, myrophine, nalbuphine, narccine, nicomorphine, norlevorphanol, normethadone, nalorphine, normorphine, norpipanone, opium, oxycodone, oxymorphone, papaveretum, pentazocine, phenadoxone, phenomorphan, phenazocine, phenoperidine, piminodine, piritramide, propheptazine, promedol, properidine, propiram, propoxyphene, sufentanil, tilidine, tramadol, and pharmaceutically acceptable salts, complexes, solvates or anhydrates thereof, and mixtures thereof.

3. The pharmaceutical composition according to claim 1, wherein the opioid is selected from the group consisting of morphine, oxycodone, oxymorphone, hydrocodone, hydromorphine, dihydromorphine, and pharmaceutically acceptable salts, complexes, solvates or anhydrates thereof, and mixtures thereof.

4. The pharmaceutical composition according to claim 1, wherein the opioid is selected from the group consisting of hydrocodone, and pharmaceutically acceptable salts, complexes, solvates or anhydrates thereof and mixtures thereof.

5. The pharmaceutical composition according to claim 1, wherein the opioid is selected from the group consisting of oxycodone, and pharmaceutically acceptable salts, complexes, solvates or anhydrates thereof and mixtures thereof.

6. The pharmaceutical composition of claim 1, wherein the opioid is selected from the group consisting of morphine, morphine 6-glucuronide, morphine 3-glucuronide, and pharmaceutically acceptable salts, complexes, solvates or anhydrates thereof and mixtures thereof.

7. The pharmaceutical composition of claim 1, wherein the erodible matrix composition does not comprise polyethylene glycol 2000 monostearate or polyethylene glycol 400 monostearate.

8. The pharmaceutical composition of claim 1, wherein the matrix composition comprises from about 10 to about 60% w/w/of the opioid.

9. The pharmaceutical composition of claim 1, wherein the coating is substantially insoluble in and impermeable to aqueous media.

10. The pharmaceutical composition according to claim 1, wherein, in the aqueous medium in which the composition is to be used, the coating does not completely crumble or erode before the matrix has completely eroded.

11. The pharmaceutical composition of claim 1, wherein the coating comprises polylactic acid.

12. The pharmaceutical composition of claim 11, wherein the plasticizer of the coating comprises polyethylene oxide.

13. The pharmaceutical composition of claim 1, wherein the ratio of the largest diameter to the smallest diameter of the conus-shaped end portion is about 1.2 to 1.

14. The pharmaceutical composition of claim 1, wherein the cones-shaped end portion extends across about 5% of the long axis of the cylindrical shape of the matrix composition.

15. The pharmaceutical composition according to claim 1, wherein the matrix composition further comprises a block copolymer of ethylene oxide and propylene oxide having a molecular weight of from about 4,000 to about 30,000 daltons.

16. The pharmaceutical composition according to claim 1, wherein the matrix composition further comprises a poloxamer.

17. The pharmaceutical composition according to claim 1, wherein the matrix composition further comprises a second polyethylene oxide having a different molecular weight than the first polyethylene oxide, wherein the average molecular weight of the polyethylene oxides in the matrix composition is selected from the group consisting of about 150,000 daltons, about 200,000 daltons, about 250,000 daltons, and about 300,000 daltons.

18. The pharmaceutical composition according to claim 1, wherein the matrix composition further comprises a second polyethylene oxide having a different molecular weight than the first polyethylene oxide, wherein the molecular weight of the second polyethylene oxide in the matrix composition is selected from the group consisting of about 100,000 daltons, about 150,000 daltons, about 200,000 daltons, about 250,000 daltons, about 300,000 daltons, and about 400,000 daltons.

19. The pharmaceutical composition according to claim 1, wherein the matrix composition further comprising an antioxidant selected from the group consisting of TPG, TPGS, BHA, BHT, t-butyl hydroquinone, calcium ascorbate, gallic acid, hydroquinone, maltol, octyl gallate, sodium bisulfite, sodium metabisulfite, tocopherol and derivates thereof, citric acid, tartaric acid, and ascorbic acid.

20. The pharmaceutical composition of claim 1, wherein the matrix composition further comprises a cellulose derivative selected from the group consisting of microcrystalline cellulose, methylcellulose, ethylcellulose, carboxymethylcellulose, ethylhydroxyethylcellulose, ethylmethylcellulose, hydroxyethylcellulose, hydroxyethylmethylcellulose, hydroxypropylcellulose, hydroxypropylmethylcellulose, hydroxymethylcellulose and hydroxymethylpropylcellulose.

21. The pharmaceutical composition according to claim 1, wherein the matrix composition further comprises a release modifier selected from the group consisting of cellulose acetate phthalate, polyvinyl acetate phthalate, hydroxypropyl methylcellulose phthalate, hydroxypropyl methylcellulose acetate succinate, and methacrylic acid copolymers.

22. The pharmaceutical composition of claim 1, wherein the matrix composition further comprises a pharmaceutically acceptable excipient selected from the group consisting of mannitol, xylitol, sorbitol and inositol.

23. The pharmaceutical composition according to claim 1, formulated for once-daily administration.

24. The pharmaceutical composition according to claim 1, formulated for twice-daily administration.

* * * * *